US009642847B2

(12) United States Patent
Chan et al.

(10) Patent No.: US 9,642,847 B2
(45) Date of Patent: *May 9, 2017

(54) COMBINATIONAL COMPOSITIONS AND METHODS FOR TREATMENT OF CANCER

(71) Applicants: ArQule, Inc., Burlington, MA (US); Kyowa Hakko Kirin Co., Ltd., Tokyo (JP)

(72) Inventors: Thomas C. K. Chan, Winchester, MA (US); Dennis S. France, Winchester, MA (US); Kenichi Ishii, Shizuoka (JP); Paolo Pucci, Westport, CT (US)

(73) Assignee: ArQule, Inc., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/807,939

(22) Filed: Jul. 24, 2015

(65) Prior Publication Data
US 2015/0328208 A1 Nov. 19, 2015

Related U.S. Application Data

(63) Continuation of application No. 12/704,361, filed on Feb. 11, 2010, now abandoned.

(60) Provisional application No. 61/152,138, filed on Feb. 12, 2009, provisional application No. 61/170,471, filed on Apr. 17, 2009.

(51) Int. Cl.
*A61K 31/4745* (2006.01)
*A61K 31/517* (2006.01)
*A61K 45/06* (2006.01)

(52) U.S. Cl.
CPC ........ *A61K 31/4745* (2013.01); *A61K 31/517* (2013.01); *A61K 45/06* (2013.01)

(58) Field of Classification Search
CPC .......................... A61K 31/4745; A61K 31/517
See application file for complete search history.

(56) References Cited

U.S. PATENT DOCUMENTS

| | | | |
|---|---|---|---|
| 4,522,811 A | 6/1985 | Eppstein et al. | |
| 7,713,969 B2 | 5/2010 | Li et al. | |
| 8,216,571 B2 | 7/2012 | Ramachandra et al. | |
| 8,304,425 B2 | 11/2012 | Wang et al. | |
| 8,575,191 B2 | 11/2013 | Chen et al. | |
| 8,580,764 B2 * | 11/2013 | Abbadessa ............ | A61K 31/437 514/220 |
| 8,754,078 B2 * | 6/2014 | Li ........................ | C07D 471/06 514/110 |
| 2006/0223760 A1 | 10/2006 | Li et al. | |
| 2010/0221251 A1 | 9/2010 | Li et al. | |
| 2011/0104256 A1 | 5/2011 | Wang et al. | |
| 2012/0004191 A1 | 1/2012 | Abbadessa et al. | |
| 2012/0052062 A1 | 3/2012 | Chen et al. | |

FOREIGN PATENT DOCUMENTS

| | | |
|---|---|---|
| WO | WO-2006086484 A1 | 8/2006 |
| WO | WO-2008127710 A2 | 10/2008 |
| WO | WO-2009002806 A1 | 12/2008 |
| WO | WO-2010093789 A2 | 8/2010 |

OTHER PUBLICATIONS

Arora et al. The Journal of Pharmacology and Experimental Therapeutics, 2006, vol. 316, No. 3, pp. 971-979.
Registry Data for Tivantinib (Registry No. 905854-02-6; Accessed Apr. 19, 2012).
Laux et al. "Phase I Dose Escalation Trial (ARQ 197-11) Evaluating Combination of Selective c-Met Inhibitor ARQ 197 and Erlotinib." *J. Clin. Oncol.* 27.15S(2009). (Abstract #3549).
Schiller et al. "Results from ARQ 197-209: A Global Randomized Placebo-Controlled Phase II Clinical Trial of Erlotinib Plus ARQ 197 Versus Erlotinib Plus Placebo in Previously Treated Egfr Inhibito-Naive Patients with Locally Advanced or Metastatic Non-Small Cell Lung Cancer (NSCLC)." *J. Clin. Oncol.* 28.18S(2010). (Abstract #LBA7502).
Cappuzzo et al. "Epidermal Growth Factor Receptor Gene and Protein and Gefitinib Sensitivity in Non-Small-Cell Lung Cancer." *J. Natl. Cancer Inst.* 97.9(2005):643-655.
Cappuzzo et al. "Increased MET Gene Copy Number Negatively Affects Survival of Surgically Resected Non-Small-Cell Lung Cancer Patients." *J. Clin. Oncol.* 27.10(2009):1667-1674.
Cerqueira et al. "Understanding Ribonucleotide Reductase Inactivation by Gemcitabine." *Chem. Eur. J.* 13.30(2007):8507-8515.
Comoglio et al. "Drug Development of MET Inhibitors: Targeting Oncogene Addiction and Expedience." *Nat. Rev. Drug Disc.* 7.6(2008):504-516.
Go et al. "High MET Gene Copy Number Leads to Shorter Survival in Patients With Non-Small Cell Lung Cancer." *J. Thorac. Oncol.* 5.3(2010):305-313.
Jackman et al. "Impact of Epidermal Growth Factor Receptor and KRAS Mutations on Clinical Outcomes in Previously Untreated Non-Small Cell Lung Cancer Patients: Results of an Online Tumor Registry of Clinical Trials." *Clin. Cancer Res.* 15.16(2009):5267-5273.
Li et al. "An Improved Protocol for the Preparation of 3-Pyridyl-and Some Arylboronic Acids." *J. Org. Chem.* 67(2002):5394-5397.
Massarelli et al. "KRAS Mutation is an Important Predictor of Resistance to Therapy With Epidermal Growth Factor Receptor Tyrosine Kinase Inhibitors in Non-Small-Cell Lung Cancer." *Clin. Cancer Res.* 13.10(2007):2890-2896.
Pao et al. "EGF Receptor Gene Mutations are Common in Lung Cancers From "Never Smokers" and are Associated With Sensitivity of Tumors to Gefitinib and Erlotinib." *PNAS.* 101. 36(2004):13306-13311.

(Continued)

*Primary Examiner* — James D Anderson
(74) *Attorney, Agent, or Firm* — Cooley LLP; Matthew Pavao; Chen Chen

(57) ABSTRACT

The present invention provides methods of treating a cell proliferative disorder, such as a cancer, by administering to a subject in need thereof a therapeutically effective amount of a pyrroloquinolinyl-pyrrole-2,5-dione compound or a pyrroloquinolinyl-pyrrolidine-2,5-dione compound in combination with a therapeutically effective amount of a second anti-proliferative agent.

5 Claims, 14 Drawing Sheets

(56) References Cited

OTHER PUBLICATIONS

Rosell et al. "Screening for Epidermal Growth Factor Receptor Mutations in Lung Cancer." *N. Engl. J. Med.* 361.10(2009):958-967.
Shepherd et al. "Erlotinib in Previously Treated Non-Small-Cell Lung Cancer." *N. Engl. J. Med.* 353.2(2005):123-132.
Therasse et al. "New Guidelines to Evaluate the Response to Treatment in Solid Tumors." *J. Natl. Cancer Inst.* 92.3(2000):205-216.
Bardelli et al., "Gab1 coupling to the HGF/MET receptor multifunctional docking site requires binding of Grb2 and correlates with the transforming potential", *Oncogene*, 15:3103-3111 (1997).
Beviglia et al., "Expression of the c-Met/HGF Receptor in Human Breast Carcinoma: Correlation with Tumor Progression", *Int. J. Cancer*, 74:301-309 (1997).
Birchmeier et al., "Met, Metastasis, Motility and More", *Nature Rev.*, 4:915-925 (2003).
Chou, T. C., "The Median-Effect Principle and the Combination Index for Quantitation of Synergism and Antagonism", in *Synergism and Antagonism in Chemotherapy*, Eds., Chou & Rideout, Academic Press, Inc., San Diego, Ch. 2, pp. 61-102 (1991).
Cooper et al., "Molecular cloning of a new transforming gene from a chemically transformed human cell line", *Nature*, 311:29-33 (1984).
Danilkovitch-Miagkova et al., "Dysregulation of Met receptor tyrosine kinase activity in invasive tumors", *J. Clin. Invest.*, 109:863-867 (2002).
Hughes, D. L., "The Mitsunobu Reaction", in *Organic Reactions*, John Wiley & Sons, Inc., vol. 42, Ch. 2, pp. 335-395 (1992).
Li et al., "An Improved Protocol for the Preparation of 3-Pyridyl- and Some Arylboronic Acids", J. Org. Chem., 67:5394-5397 (2002).
Li et al., "Selective killing of cancer cells by β-lapachone: Direct checkpoint activation as a strategy against cancer", *Proc. Natl. Acad. Sci. U.S.A.*, 100(5):2674-2678 (2003).
Ma et al., "c-Met: Structure, functions and potential for therapeutic inhibitions", *Cancer Metast. Rev.*, 22:309-325 (2003).
Marson et al., "Highly efficient syntheses of 3-aryl-2-cycloalken-1-ones and an evaluation of their liquid crystalline properties", *Tetrahedron*, 59:4377-4381 (2003).
Mark et al., "Combination efficacy with MetMAb and erlotinib in NSCLC tumor model highlight therapeutic opportunities for c-Met inhibitors in combination with EGFR inhibitors", *99th AACR Annual Meeting*, 49:313-314 (Apr. 12-16, 2008) (Abstract Only).
Mitsunobu et al., "Stereospecific and Stereoselective Reactions. I. Preparation of Amines from Alcohols", *J. Am. Chem. Soc.*, 94:679-680 (1972).
Nakajima et al., "The Prognostic Significance of Amplification and Overexpression of c-met and c-erb B-2 in Human Gastric Carcinomas", *Cancer*, 85:1894-1902 (1999).
Puri et al., "Synergism of EGFR and c-Met pathways, cross-talk and inhibition, in non-small cell lung cancer", *J. Carcinogenesis*, 7:9 (2008).
Qian et al., "Met Protein Expression Level Correlates with Survival in Patients with Late-stage Nasopharyngeal Carcinoma", *Cancer Res.*, 62:589-596 (2002).
Qiao et al., "Constitutive Activation of Met Kinase in Non-Small-Cell Lung Carcinomas Correlates With Anchorage-Independent Cell Survival", *J. Cell. Biochem.*, 86:665-677 (2002).
Rosen et al., "A Phase 1 dose escalation study of ARQ 197, a selective inhibitor of the c-Met receptor in patients with metastatic solid tumors", *Eur. J. Cancer*, Suppl. 4:196 (Abstract Only).
Seiwert et al., "The MET receptor tyrosine kinase is a potential novel therapeutic target for head and neck squamous cell carcinoma", *Cancer Res*, 69(7):3021-3031 (2009).
Takayama et al., "Diverse tumorigenesis associated with aberrant development in mice overexpressing hepatocyte growth factor/scatter factor", *Proc. Natl. Acad. Sci. U.S.A.*, 94:701-706 (1997).
Takeuchi et al., "c-MET Expression Level in Primary Colon Cancer: A Predictor of Tumor Invasion and Lymph Node Metastases", *Clin. Cancer Res.*, 9:1480-1488 (2003).
Tang et al., "Dual MET-EGFR combinatorial inhibition against T790M-EGFR-mediated erlotinib-resistant lung cancer", *Br. J. Cancer*, 99:911-922 (2008).
Thurlimann et al., "Management of Primary Breast Cancer: An Update", *Onkologie*, 27:175-179 (2004).
Traxler et al., "Tyrosine Kinase Inhibitors: From Rational Design to Clinical Trials", *Med. Res. Rev.*, 21(6):499-512 (2001).
Weidner et al., "The Met Receptor Tyrosine Kinase Transduces Motility, Proliferation, and Morphogenic Signals of Scatter Factor/Hepatocyte Growth Factor in Epithelial Cells", *J. Cell Biol.*, 121(1):145-154 (1993).
Zhang et al., "Met decoys: Will cancer take the bait?", *Cancer Cell*, 6: 5-6 (2004).

* cited by examiner (±)-cis-3-(5,6-dihydro-4H-pyrrolo [3,2,1-ij] quinolin-1-yl)-4-(1H-indol-3-yl) pyrrolidine-2, 5-dione (±)-trans-3-(5,6-dihydro-4H-pyrrolo [3,2,1-ij] quinolin-1-yl)-4-(1H-indol-3-yl) pyrrolidine-2, 5-dione $$CI = \frac{C_A^{mix}}{C_A^0} + \frac{C_B^{mix}}{C_B^0}$$

COMBINATIONAL COMPOSITIONS AND METHODS FOR TREATMENT OF CANCER

CROSS-REFERENCE TO RELATED APPLICATIONS

This application is a continuation of U.S. application Ser. No. 12/704,361, filed Feb. 11, 2010, which claims the benefit of, and priority to, U.S. Provisional Application No. 61/152,138, filed Feb. 12, 2009 and U.S. Provisional Application No. 61/170,471, filed Apr. 17, 2009. The contents of each of these applications are incorporated herein by reference in their entirety.

BACKGROUND OF THE INVENTION

Cancer is the second leading cause of death in the United States, exceeded only by heart disease. (*Cancer Facts and Figures* 2004, American Cancer Society, Inc.) Despite recent advances in cancer diagnosis and treatment, surgery and radiotherapy may be curative if a cancer is found early, but current drug therapies for metastatic disease are mostly palliative and seldom offer a long-term cure. Even with new chemotherapies entering the market, the need continues for new drugs effective in monotherapy or in combination with existing agents as first line therapy, and as second and third line therapies in treatment of resistant tumors.

Cancer cells are by definition heterogeneous. For example, within a single tissue or cell type, multiple mutational 'mechanisms' may lead to the development of cancer. As such, heterogeneity frequently exists between cancer cells taken from tumors of the same tissue and same histiotype that have originated in different individuals. Frequently observed mutational 'mechanisms' associated with some cancers may differ between one tissue type and another (e.g., frequently observed mutational 'mechanisms' leading to colon cancer may differ from frequently observed 'mechanisms' leading to leukemias). It is therefore often difficult to predict whether a particular cancer will respond to a particular chemotherapeutic agent. (*Cancer Medicine,* 5th Edition, Bast et al. eds., B.C. Decker Inc., Hamilton, Ontario)

Breast cancer is the most frequently diagnosed non-skin cancer in women, and ranks second among cancer deaths in women, after lung cancer. (*Cancer Facts and Figures* 2004, American Cancer Society, Inc.) Current treatment options for breast cancer include surgery, radiotherapy, and chemotherapy/hormone therapy with agents such as tamoxifen, aromatase inhibitors, HERCEPTIN® (trastuzumab), TAXOL® (paclitaxel), cyclophosphamide, methotrexate, doxorubicin (Adriamycin®), and 5-fluorouracil (5-FU). Despite improvements in cancer diagnostics and therapeutics, breast cancer incidence rates have continued to increase since 1980. In 2004, about 215,000 new cases of breast cancer are expected in women, and about 1,450 new cases of breast cancer are expected in men. Id. Accordingly, new compounds and methods for treating breast cancer are needed.

Components of cellular signal transduction pathways that regulate the growth and differentiation of normal cells can, when dysregulated, lead to the development of cellular proliferative disorders and cancer. Mutations in cellular signaling proteins may cause such proteins to become expressed or activated at inappropriate levels or at inappropriate times during the cell cycle, which in turn may lead to uncontrolled cellular growth or changes in cell-cell attachment properties. For example, dysregulation of receptor tyrosine kinases by mutation, gene rearrangement, gene amplification, and overexpression of both receptor and ligand has been implicated in the development and progression of human cancers.

The c-Met receptor tyrosine kinase is the only known high-affinity receptor for hepatocyte growth factor (HGF), also known as scatter factor. Binding of HGF to the c-Met extracellular ligand-binding domain results in receptor multimerization and phosphorylation of multiple tyrosine residues in the intracellular portion of c-Met. Activation of c-Met results in the binding and phosphorylation of adaptor proteins such as Gab-1, Grb-2, Shc, and c-Cbl, and subsequent activation of signal transducers such as PI3K, PLC-γ, STATs, ERK1 and 2 and FAK. c-Met and HGF are dysregulated in human cancers, and may contribute to dysregulation of cell growth, tumor cell dissemination, and tumor invasion during disease progression and metastasis. (See, e.g., *Journal of Clinical Investigation* 109: 863-867 (2002) and *Cancer Cell* pp 5-6 Jul. 2004) c-Met and HGF are highly expressed relative to surrounding tissue in numerous cancers, and their expression correlates with poor patient prognosis. (See, e.g., *Journal of Cellular Biochemistry* 86: 665-677 (2002); *Int. J. Cancer (Pred. Oncol.)* 74: 301-309 (1997); *Clinical Cancer Research* 9: 1480-1488 (2003); and *Cancer Research* 62: 589-596 (2002)) Without intending to be bound by theory, c-Met and HGF may protect tumors against cell death induced by DNA damaging agents, and as such may contribute to chemoresistance and radioresistance of tumors. Without intending to be limited by any theory, inhibitors of c-Met may be useful as therapeutic agents in the treatment of proliferative disorders including breast cancer. (See, e.g., *Cancer and Metastasis Reviews* 22: 309-325 (2003))

The references cited herein are not admitted to be prior art to the claimed invention.

SUMMARY OF THE INVENTION

The present invention provides a method of treating a cell proliferative disorder, the method comprising administering to a subject in need thereof a therapeutically effective amount of a compound of formula III, IIIa, IVa, IVb, Va, or Vb, or a pharmaceutically acceptable salt thereof, or a prodrug or metabolite thereof, with one or more pharmaceutically acceptable carriers or excipients, alone, or in combination with a therapeutically effective amount of a second anti-proliferative agent, with one or more pharmaceutically acceptable carriers or excipients, wherein the cell proliferation disorder is treated.

The compound of formula III, IIIa, IVa, IVb, Va, or Vb can be (+)-cis-3-(5,6-dihydro-4H-pyrrolo[3,2,1-ij]quinolin-1-yl)-4-(1H-indol-3-yl) pyrrolidine-2,5-dione, (−)-cis-3-(5,6-dihydro-4H-pyrrolo[3,2,1-ij]quinolin-1-yl)-4-(1H-indol-3-yl) pyrrolidine-2,5-dione, (+)-trans-3-(5,6-dihydro-4H-pyrrolo[3,2,1-ij]quinolin-1-yl)-4-(1H-indol-3-yl) pyrrolidine-2,5-dione, or (−)-trans-3-(5,6-dihydro-4H-pyrrolo[3,2,1-ij]quinolin-1-yl)-4-(1H-indol-3-yl) pyrrolidine-2,5-dione. Preferably, the compound is (−)-trans-3-(5,6-dihydro-4H-pyrrolo[3,2,1-ij]quinolin-1-yl)-4-(1H-indol-3-yl) pyrrolidine-2,5-dione.

The second anti-proliferative agent can be a kinase inhibitor, an alkylating agent, an antibiotic, an anti-metabolite, a detoxifying agent, an interferon, a polyclonal or monoclonal antibody, a HER2 inhibitor, a histone deacetylase inhibitor, a hormone, a mitotic inhibitor, an MTOR inhibitor, a taxane or taxane derivative, an aromatase inhibitor, an anthracycline, a microtubule targeting drug, a topoisomerase poison drug, or a cytidine analogue drug. Preferably, the kinase inhibitor is serine/threonine kinase inhibitor or a tyrosine kinase inhibitor. Preferred kinase inhibitors include, but are not limited to, sorafenib, sunitinib, erlotinib, imatinib, and gefitinib. Preferred alkylating agents include, but are not limited to, cisplatin or carboplatin. Preferred anti-metabolites include, but are not limited to, gemcitabine, fluorouracil (5-FU), TS-1 or capecitabine. Preferred mitotic inhibitors include, but are not limited to, camptothecin or irinotecan. Preferred taxane or taxane derivatives include, but are not limited to, paclitaxel or docetaxel.

The cell proliferative disorder can be a precancerous condition or cancer. The cell proliferative disorder can be a hematologic tumor or malignancy, or a solid tumor (or tumors). The methods of treating cancer include a reduction in tumor size. Alternatively, or in addition, the cancer is metastatic cancer and this method of treatment includes inhibition of metastatic cancer cell invasion. The method can further include radiation therapy. The cancer can be lung cancer, small cell lung cancer, non-small cell lung cancer (NSCLC), colon cancer, breast cancer, pancreatic cancer, prostate cancer, renal cancer, cervical cancer, brain cancer, gastric/stomach cancer, uterine cancer, intestinal cancer, hepatic cancer, chronic myelogenous leukemia, melanoma, ovarian cancer, translocation-associated renal cell carcinoma (RCC), alveolar soft part sarcoma (ASPS), clear cell sarcoma (CCS), or hepatocellular carcinoma (HCC).

Cells with a proliferative disorder can contain DNA encoding c-Met. Alternatively, or in addition, cells with a proliferative disorder have a constitutively enhanced c-Met activity. Preferably, the cell proliferative disease is cancer, and particularly those cancers which express c-Met at high levels or express active c-Met. Thus, the present invention provides a method of treating cell proliferative disorders where the cells express c-Met at high levels or express active c-Met. The present invention further provides a method of treating a cell proliferative disorder comprising selectively modulating an activity of c-Met, without significantly inhibiting the activity of Protein Kinase C.

Preferably, the subject is a mammal More preferably, the subject is a human.

Preferably, the compound of formula III, IIIa, IVa, IVb, Va, or Vb of the methods described herein is (−)-trans-3-(5, 6-dihydro-4H-pyrrolo[3,2,1-ij]quinolin-1-yl)-4-(1H-indol-3-yl) pyrrolidine-2,5-dione and is administered at a dose of 360 mg, provided twice a day. Alternatively, the composition is administered at a maximal daily dose of 720 mg.

Preferably, the (−)-trans-3-(5,6-dihydro-4H-pyrrolo[3,2,1-ij]quinolin-1-yl)-4-(1H-indol-3-yl) pyrrolidine-2,5-dione and the second anti-proliferative agent are administered intravenously, orally or intraperitoneally. The second anti-proliferative agent can be administered simultaneously with, preceding administration of, or following administration of the composition comprising (−)-trans-3-(5,6-dihydro-4H-pyrrolo[3,2,1-ij]quinolin-1-yl)-4-(1H-indol-3-yl) pyrrolidine-2,5-dione. Preferably, the second anti-proliferative agent is administered within 24 hours after the composition comprising (−)-trans-3-(5,6-dihydro-4H-pyrrolo[3,2,1-ij]quinolin-1-yl)-4-(1H-indol-3-yl) pyrrolidine-2,5-dione is administered.

The present invention also provides a kit for the treatment of a cell proliferative disorder in a subject comprising separate vials containing a composition comprising (−)-trans-3-(5,6-dihydro-4H-pyrrolo[3,2,1-ij]quinolin-1-yl)-4-(1H-indol-3-yl) pyrrolidine-2,5-dione, or a pharmaceutically acceptable salt thereof, or a prodrug or metabolite thereof, and a second anti-proliferative agent, with instructions for administering said composition and second anti-proliferative agent.

Preferably, the subject is a mammal More preferably, the subject is a human.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTION OF THE FIGURES

FIG. 2, Panel A, shows the Combination Index (CI) calculation and FIG. 2, Panel B, shows an isobologram analysis graph.

DETAILED DESCRIPTION OF THE INVENTION

1. Methods of Treatment

Figure 1:
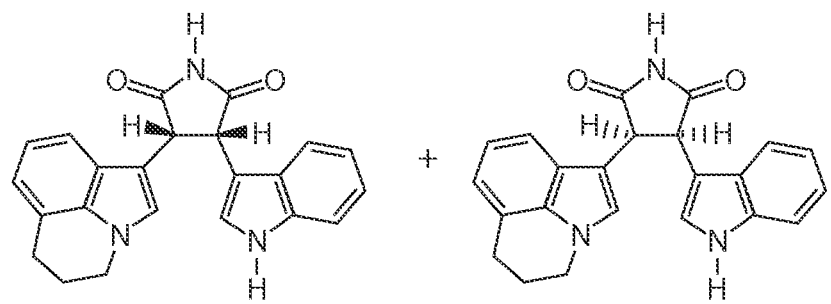
FIG. 1 sets forth the chemical structures of (±)-cis-3-(5,6-dihydro-4H-pyrrolo[3,2,1-ij]quinolin-1-yl)-4-(1H-indol-3-yl) pyrrolidine-2,5-dione and (±)-trans-3-(5,6-dihydro-4H-pyrrolo[3,2,1-ij]quinolin-1-yl)-4-(1H-indol-3-yl) pyrrolidine-2,5-dione.
Figure 1:
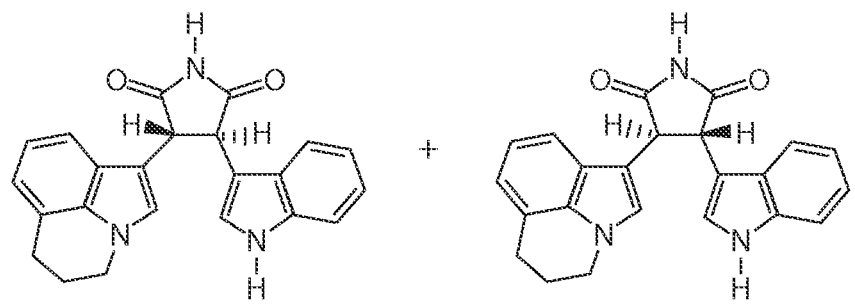

The present invention provides methods of treating a cell proliferative disorder, the method comprising administering to a subject in need thereof a therapeutically effective amount of a compound of formula III, IIIa, IVa, IVb, Va, or Vb, or a pharmaceutically acceptable salt thereof, or a prodrug or metabolite thereof, with one or more pharmaceutically acceptable carriers or excipients, alone, or in combination with a therapeutically effective amount of a second anti-proliferative agent, with one or more pharmaceutically acceptable carriers or excipients, wherein the cell proliferation disorder is treated.

The present invention provides a pharmaceutical composition for treating a cell proliferative disorder, comprising a combination of (a) a therapeutically effective amount of a compound of formula III, IIIa, IVa, IVb, Va, or Vb, or a pharmaceutically acceptable salt thereof, or a prodrug or metabolite thereof, alone, or in combination with (b) a therapeutically effective amount of a second anti-proliferative agent. One or more pharmaceutically acceptable carriers or excipients is (are) optionally included in the composition.

A second anti-proliferative agent is preferably a second chemotherapeudic agent.

The cell proliferative disorder can be a precancerous condition or cancer. The cell proliferative disorder can be a hematologic tumor or malignancy, or a solid tumor (or tumors). This method of treating cancer include a reduction in tumor size. Alternatively, or in addition, the cancer is metastatic cancer and this method of treatment includes inhibition of metastatic cancer cell invasion.

The second chemotherapeutic agent (also referred to as an anti-neoplastic agent or anti-proliferative agent) can be an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine, tositumomab (Bexxar); alemtuzumab (Campath); ibritumomab (In-111 Zevalin); gemtuzumab (Mylotarg); eculizumab (Soliris); ibritumomab (Y-90 Zevalin); denosumab or ibritumomab (Zevalin).

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary mTOR inhibitors include, but are not limited to, everolimus (Afinitor) or temsirolimus (Torisel); rapamune, ridaforolimus; or AP23573.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl, PDGFRs and c-Kit), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/1apatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-B, KIT, FLT-3, and RET), Dasatinib/Sprycel (BCR/Abl and Src), AC-220 (targets Flt3), AC-480 (targets all HER proteins, "pan-HER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, eril/easudil hydrochloride; Rapamune (targets mTOR/FRAP1); Deforolimus (targets mTOR); Certican/Everolimus (targets mTOR/FRAP1); AP23573 (targets mTOR/FRAP1); Eril/Fasudil hydrochloride (targets RHO); Flavopiridol (targets CDK); Seliciclib/CYC202/Roscovitrine (targets CDKs); SNS-032/BMS-387032 (targets CDKs); Ruboxistaurin (targets PKC); Pkc412 (targets PKC); Bryostatin (targets PKC); KAI-9803 (targets PKC); SF1126 (targets PI3K); VX-680 (targets Aurora kinase); Azd1152 (targets Aurora kinase); Arry-142886/AZD-6244 (targets MAP/MEK); SCIO-469 (targets MAP/MEK); GW681323 (targets MAP/MEK); CC-401 (targets JNK); CEP-1347 (targets JNK); and PD 332991 (targets CDKs).

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary aromatase inhibitors include, but are not limited to, aminoglutethimide, testolactone (Teslac), anastrozole (Arimidex), Letrozole (Femara), exemestane (Aromasin), Vorozole (Rivizor), Formestane (Lentaron), Fadrozole (Afema), 4-androstene-3,6,17-trione (6-OXO), 1,4,6-androstatrien-3,17-dione (ATD), and 4-hydroxyandrostenedione.

Exemplary anthracyclines include, but are not limited to, daunorubicin (Daunomycin), doxorubicin (Adriamycin), epirubicin, idarubicin, and valrubicin.

Exemplary cytidine analogs include, but are not limited to, gemcitabine, azacytidine (e.g., 5-azacytidine), and cytosine arabinoside (cytarabin, araC, Cytosar).

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxel.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur—0.4 M 5-chloro-2,4-dihydroxypyrimidine—1 M potassium oxonate) or statins (e.g., lovastatin, atorvastatin, cerivastatin, fluvastatin, mevastatin, pitavastatin, pravastatin, rosuvastatin, and simvastatin).

In another aspect, the second chemotherapeutic agent can be a cytokine such as G-CSF (granulocyte colony stimulating factor). In another aspect, a compound of formula III, IIIa, IVa, IVb, Va, or Vb, or a pharmaceutically acceptable salt, prodrug, metabolite, analog or derivative thereof, may be administered in combination with radiation therapy. Radiation therapy can also be administered in combination with a compound of formula III, IIIa, IVa, IVb, Va, or Vb and another chemotherapeutic agent described herein as part of a multiple agent therapy. In yet another aspect, a compound of formula III, IIIa, IVa, IVb, Va, or Vb, or a pharmaceutically acceptable salt, prodrug, metabolite, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™) or CMFP (cyclophosphamide, methotrexate, 5-fluorouracil and prednisone).

In preferred embodiments, a compound of formula III, IIIa, IVa, IVb, Va, or Vb, or a pharmaceutically acceptable salt, prodrug, metabolite, polymorph or solvate thereof, may be administered with an inhibitor of an enzyme, such as a receptor or non-receptor kinase. Receptor and non-receptor kinases of the invention are, for example, tyrosine kinases or serine/threonine kinases. Kinase inhibitors of the invention are small molecules, polynucleic acids, polypeptides, or antibodies.

Preferred combinatorial therapies include, but are not limited to, (−)-trans-3-(5,6-dihydro-4H-pyrrolo[3,2,1-ij]quinolin-1-yl)-4-(1H-indol-3-yl) pyrrolidine-2,5-dione administered in combination with erlotinib, (−)-trans-3-(5,6-dihydro-4H-pyrrolo[3,2,1-ij]quinolin-1-yl)-4-(1H-indol-3-yl) pyrrolidine-2,5-dione administered in combination with sorafenib, (−)-trans-3-(5,6-dihydro-4H-pyrrolo[3,2,1-ij]quinolin-1-yl)-4-(1H-indol-3-yl) pyrrolidine-2,5-dione administered in combination with sunitinib; (−)-trans-3-(5,6-dihydro-4H-pyrrolo[3,2,1-ij]quinolin-1-yl)-4-(1H-indol-3-yl) pyrrolidine-2,5-dione administered in combination with capecitabine; (−)-trans-3-(5,6-dihydro-4H-pyrrolo[3,2,1-ij]quinolin-1-yl)-4-(1H-indol-3-yl) pyrrolidine-2,5-dione administered in combination with carboplatin and (−)-trans-3-(5,6-dihydro-4H-pyrrolo[3,2,1-ij]quinolin-1-yl)-4-(1H-indol-3-yl) pyrrolidine-2,5-dione administered in combination with cisplatin. In certain embodiments, a subject or patient receives a combination of erlotinib, administered as 150 mg once daily, in combination with (−)-trans-3-(5,6-dihydro-4H-pyrrolo[3,2,1-ij]quinolin-1-yl)-4-(1H-indol-3-yl) pyrrolidine-2,5-dione, administered as 360 mg twice daily. In another embodiment, a subject or patient receives a combination of sorafenib, administered as 200 mg twice daily, in combination with (−)-trans-3-(5,6-dihydro-4H-pyrrolo[3,2,1-ij]quinolin-1-yl)-4-(1H-indol-3-yl) pyrrolidine-2,5-dione, administered as 360 mg twice daily. Preferred dosage forms for (−)-trans-3-(5,6-dihydro-4H-pyrrolo[3,2,1-ij]quinolin-1-yl)-4-(1H-indol-3-yl) pyrrolidine-2,5-dione include, but are not limited to, a casule and a tablet.

The present examples demonstrate at least an additive anti-proliferative effect for various cancers, in vitro and in vivo, when (−)-trans-3-(5,6-dihydro-4H-pyrrolo[3,2,1-ij]quinolin-1-yl)-4-(1H-indol-3-yl) pyrrolidine-2,5-dione is administered in combination with sorafenib, sunitinib, erlotinib, gefitinib, cisplatin, carboplatin or capecitabine. These cancers include, but are not limited to, lung cancer, small cell lung cancer, non-small cell lung cancer, colon cancer, breast cancer, pancreatic cancer, prostate cancer, renal cancer, cervical cancer, brain cancer, gastric/stomach cancer, uterine cancer, intestinal cancer, hepatic cancer, chronic myelogenous leukemia, melanoma, ovarian cancer, translocation-associated renal cell carcinoma (RCC), alveolar soft part sarcoma (ASPS), clear cell sarcoma (CCS), and hepatocellular carcinoma. The anti-proliferative effects of these combinational treatments are increased/enhanced in cell proliferative disorders and cancers in which the effected cells constitutively express or over-express c-Met. In addition, synergistic anti-proliferative effects are shown by (−)-trans-3-(5,6-dihydro-4H-pyrrolo[3,2,1-ij]quinolin-1-yl)-4-(1H-indol-3-yl) pyrrolidine-2,5-dione in combination with sorafenib in breast cancer, cervical cancer, lung cancer, small cell lung cancer, non-small cell lung cancer, melanoma, colon cancer, pancreatic cancer, renal cancer and gastric/stomach cancer; by (−)-trans-3-(5,6-dihydro-4H-pyrrolo[3,2,1-ij]quinolin-1-yl)-4-(1H-indol-3-yl) pyrrolidine-2,5-dione in combination with sunitinib in gastric/stomach cancer; by (−)-trans-3-(5,6-dihydro-4H-pyrrolo[3,2,1-ij]quinolin-1-yl)-4-(1H-indol-3-yl) pyrrolidine-2,5-dione in combination with erlotinib in lung cancer, small cell lung cancer, non-small cell lung cancer and colon cancer; and by (−)-trans-3-(5,6-dihydro-4H-pyrrolo[3,2,1-ij]quinolin-1-yl)-4-(1H-indol-3-yl) pyrrolidine-2,5-dione in combination with cisplatin in pancreatic cancer.

A compound of formula III, IIIa, IVa, IVb, Va, or Vb of the present invention, or a pharmaceutically acceptable salt, prodrug, metabolite, analog or derivative thereof, can be incorporated into pharmaceutical compositions suitable for administration. Such compositions typically comprise the compound (i.e. including the active compound), and a pharmaceutically acceptable excipient or carrier. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, ringer's solutions, dextrose solution, and 5% human serum albumin.

Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like. Other fillers, excipients, flavorants, and other additives such as are known in the art may also be included in a pharmaceutical composition according to this invention. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In one aspect, a compound of formula III, IIIa, IVa, IVb, Va, or Vb, or a pharmaceutically acceptable salt, prodrug, metabolite, analog or derivative thereof, is administered in a suitable dosage form prepared by combining a therapeutically effective amount (e.g., an efficacious level sufficient to achieve the desired therapeutic effect through inhibition of tumor growth, killing of tumor cells, treatment or prevention of cell proliferative disorders, etc.) of a compound of formula III, Ma, IVa, IVb, Va, or Vb, or a pharmaceutically acceptable salt, prodrug, metabolite, analog or derivative thereof, (as an active ingredient) with standard pharmaceutical carriers or diluents according to conventional procedures (i.e., by producing a pharmaceutical composition of the invention). These procedures may involve mixing, granulating, and compressing or dissolving the ingredients as appropriate to attain the desired preparation.

As used herein, a "subject" can be any mammal, e.g., a human, a primate, mouse, rat, dog, cat, cow, horse, pig, sheep, goat, camel. In a preferred aspect, the subject is a human.

As used herein, a "subject in need thereof" is a subject having a cell proliferative disorder, or a subject having an increased risk of developing a cell proliferative disorder relative to the population at large. In one aspect, a subject in need thereof has a precancerous condition. In a preferred aspect, a subject in need thereof has cancer.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, precancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi's sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. In one aspect, a cell proliferative disorder of the hematologic system includes lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. In another aspect, a cell proliferative disorder of the hematologic system includes hyperplasia, dysplasia, and metaplasia of cells of the hematologic system. In a preferred aspect, compositions of the present invention may be used to treat a cancer selected from the group consisting of a hematologic cancer of the present invention or a hematologic cell proliferative disorder of the present invention. In one aspect, a hematologic cancer of the present invention includes multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. In one aspect, cell proliferative disorders of the lung include all forms of cell proliferative disorders affecting lung cells. In one aspect, cell proliferative disorders of the lung include lung cancer, a precancer or precancerous condition of the lung, benign growths or lesions of the lung, and malignant growths or lesions of the lung, and metastatic lesions in tissue and organs in the body other than the lung. In a preferred aspect, compositions of the present invention may be used to treat lung cancer or cell proliferative disorders of the lung. In one aspect, lung cancer includes all forms of cancer of the lung. In another aspect, lung cancer includes malignant lung neoplasms, carcinoma in situ, typical carcinoid tumors, and atypical carcinoid tumors. In another aspect, lung cancer includes small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. In another aspect, lung cancer includes "scar carcinoma," bronchioalveolar carcinoma, giant cell carcinoma, spindle cell carcinoma, and large cell neuroendocrine carcinoma. In another aspect, lung cancer includes lung neoplasms having histologic and ultrastructual heterogeneity (e.g., mixed cell types).

In one aspect, cell proliferative disorders of the lung include all forms of cell proliferative disorders affecting lung cells. In one aspect, cell proliferative disorders of the lung include lung cancer, precancerous conditions of the lung. In one aspect, cell proliferative disorders of the lung include hyperplasia, metaplasia, and dysplasia of the lung.

In another aspect, cell proliferative disorders of the lung include asbestos-induced hyperplasia, squamous metaplasia, and benign reactive mesothelial metaplasia. In another aspect, cell proliferative disorders of the lung include replacement of columnar epithelium with stratified squamous epithelium, and mucosal dysplasia. In another aspect, individuals exposed to inhaled injurious environmental agents such as cigarette smoke and asbestos may be at increased risk for developing cell proliferative disorders of the lung. In another aspect, prior lung diseases that may predispose individuals to development of cell proliferative disorders of the lung include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. In a preferred aspect, the cell proliferative disorder of the colon is colon cancer. In a preferred aspect, compositions of the present invention may be used to treat colon cancer or cell proliferative disorders of the colon. In one aspect, colon cancer includes all forms of cancer of the colon. In another aspect, colon cancer includes sporadic and hereditary colon cancers. In another aspect, colon cancer includes malignant colon neoplasms, carcinoma in situ, typical carcinoid tumors, and atypical carcinoid tumors. In another aspect, colon cancer includes adenocarcinoma, squamous cell carcinoma, and adenosquamous cell carcinoma. In another aspect, colon cancer is associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. In another aspect, colon cancer is caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

In one aspect, cell proliferative disorders of the colon include all forms of cell proliferative disorders affecting colon cells. In one aspect, cell proliferative disorders of the colon include colon cancer, precancerous conditions of the colon, adenomatous polyps of the colon and metachronous lesions of the colon. In one aspect, a cell proliferative disorder of the colon includes adenoma. In one aspect, cell proliferative disorders of the colon are characterized by hyperplasia, metaplasia, and dysplasia of the colon. In another aspect, prior colon diseases that may predispose individuals to development of cell proliferative disorders of the colon include prior colon cancer. In another aspect, current disease that may predispose individuals to development of cell proliferative disorders of the colon include Crohn's disease and ulcerative colitis. In one aspect, a cell proliferative disorder of the colon is associated with a mutation in a gene selected from the group consisting of p53, ras, FAP and DCC. In another aspect, an individual has an elevated risk of developing a cell proliferative disorder of the colon due to the presence of a mutation in a gene selected from the group consisting of p53, ras, FAP and DCC.

A "cell proliferative disorder of the prostate" is a cell proliferative disorder involving cells of the prostate. In one aspect, cell proliferative disorders of the prostate include all forms of cell proliferative disorders affecting prostate cells.

In one aspect, cell proliferative disorders of the prostate include prostate cancer, a precancer or precancerous condition of the prostate, benign growths or lesions of the prostate, and malignant growths or lesions of the prostate, and metastatic lesions in tissue and organs in the body other than the prostate. In another aspect, cell proliferative disorders of the prostate include hyperplasia, metaplasia, and dysplasia of the prostate.

A "cell proliferative disorder of the skin" is a cell proliferative disorder involving cells of the skin. In one aspect, cell proliferative disorders of the skin include all forms of cell proliferative disorders affecting skin cells. In one aspect, cell proliferative disorders of the skin include a precancer or precancerous condition of the skin, benign growths or lesions of the skin, melanoma, malignant melanoma and other malignant growths or lesions of the skin, and metastatic lesions in tissue and organs in the body other than the skin. In another aspect, cell proliferative disorders of the skin include hyperplasia, metaplasia, psoriasis, and dysplasia of the skin.

A "cell proliferative disorder of the ovary" is a cell proliferative disorder involving cells of the ovary. In one aspect, cell proliferative disorders of the ovary include all forms of cell proliferative disorders affecting cells of the ovary. In one aspect, cell proliferative disorders of the ovary include a precancer or precancerous condition of the ovary, benign growths or lesions of the ovary, ovarian cancer, malignant growths or lesions of the ovary, and metastatic lesions in tissue and organs in the body other than the ovary. In another aspect, cell proliferative disorders of the ovary include hyperplasia, metaplasia, and dysplasia of cells of the ovary.

A "cell proliferative disorder of the breast" is a cell proliferative disorder involving cells of the breast. In one aspect, cell proliferative disorders of the breast include all forms of cell proliferative disorders affecting breast cells. In one aspect, cell proliferative disorders of the breast include breast cancer, a precancer or precancerous condition of the breast, benign growths or lesions of the breast, and malignant growths or lesions of the breast, and metastatic lesions in tissue and organs in the body other than the breast. In another aspect, cell proliferative disorders of the breast include hyperplasia, metaplasia, and dysplasia of the breast.

In one aspect, a cell proliferative disorder of the breast is a precancerous condition of the breast. In one aspect, compositions of the present invention may be used to treat a precancerous condition of the breast. In one aspect, a precancerous condition of the breast includes atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). In another aspect, a precancerous condition of the breast has been staged according to the TNM classification scheme as accepted by the American Joint Committee on Cancer (AJCC), where the primary tumor (T) has been assigned a stage of T0 or Tis; and where the regional lymph nodes (N) have been assigned a stage of NO; and where distant metastasis (M) has been assigned a stage of MO.

In a preferred aspect, the cell proliferative disorder of the breast is breast cancer. In a preferred aspect, compositions of the present invention may be used to treat breast cancer. In one aspect, breast cancer includes all forms of cancer of the breast. In one aspect, breast cancer includes primary epithelial breast cancers. In another aspect, breast cancer includes cancers in which the breast is involved by other tumors such as lymphoma, sarcoma or melanoma. In another aspect, breast cancer includes carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. In one aspect, breast cancer includes Stage I, II, IIIA, IIIB, IIIC and IV breast cancer. In one aspect, ductal carcinoma of the breast includes invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. In one aspect, lobular carcinoma of the breast includes invasive lobular carcinoma with predominant in situ component, invasive lobular carcinoma, and infiltrating lobular carcinoma. In one aspect, breast cancer includes Paget's disease, Paget's disease with intraductal carcinoma, and Paget's disease with invasive ductal carcinoma. In another aspect, breast cancer includes breast neoplasms having histologic and ultrastructual heterogeneity (e.g., mixed cell types).

In a preferred aspect, a compound of formula III, IIIa, IVa, IVb, Va, or Vb may be used to treat breast cancer. In one aspect, a breast cancer that is to be treated includes familial breast cancer. In another aspect, a breast cancer that is to be treated includes sporadic breast cancer. In one aspect, a breast cancer that is to be treated has arisen in a male subject. In one aspect, a breast cancer that is to be treated has arisen in a female subject. In one aspect, a breast cancer that is to be treated has arisen in a premenopausal female subject or a postmenopausal female subject. In one aspect, a breast cancer that is to be treated has arisen in a subject equal to or older than 30 years old, or a subject younger than 30 years old. In one aspect, a breast cancer that is to be treated has arisen in a subject equal to or older than 50 years old, or a subject younger than 50 years old. In one aspect, a breast cancer that is to be treated has arisen in a subject equal to or older than 70 years old, or a subject younger than 70 years old.

In one aspect, a breast cancer that is to be treated has been typed to identify a familial or spontaneous mutation in BRCA1, BRCA2, or p53. In one aspect, a breast cancer that is to be treated has been typed as having a HER2/neu gene amplification, as overexpressing HER2/neu, or as having a low, intermediate or high level of HER2/neu expression. In another aspect, a breast cancer that is to be treated has been typed for a marker selected from the group consisting of estrogen receptor (ER), progesterone receptor (PR), human epidermal growth factor receptor-2, Ki-67, CA15-3, CA 27-29, and c-Met. In one aspect, a breast cancer that is to be treated has been typed as ER-unknown, ER-rich or ER-poor. In another aspect, a breast cancer that is to be treated has been typed as ER-negative or ER-positive. ER-typing of a breast cancer may be performed by any reproducible means. In a preferred aspect, ER-typing of a breast cancer may be performed as set forth in Onkologie 27: 175-179 (2004). In one aspect, a breast cancer that is to be treated has been typed as PR-unknown, PR-rich or PR-poor. In another aspect, a breast cancer that is to be treated has been typed as PR-negative or PR-positive. In another aspect, a breast cancer that is to be treated has been typed as receptor positive or receptor negative. In one aspect, a breast cancer that is to be treated has been typed as being associated with elevated blood levels of CA 15-3, or CA 27-29, or both.

In one aspect, a breast cancer that is to be treated includes a localized tumor of the breast. In one aspect, a breast cancer that is to be treated includes a tumor of the breast that is associated with a negative sentinel lymph node (SLN) biopsy. In one aspect, a breast cancer that is to be treated includes a tumor of the breast that is associated with a positive sentinel lymph node (SLN) biopsy. In another aspect, a breast cancer that is to be treated includes a tumor of the breast that is associated with one or more positive auxiliary lymph nodes, where the auxiliary lymph nodes have been staged by any applicable method. In another aspect, a breast cancer that is to be treated includes a tumor of the breast that has been typed as having nodal negative status (e.g., node-negative) or nodal positive status (e.g., node-positive). In another aspect, a breast cancer that is to be treated includes a tumor of the breast that has metastasized to other locations in the body. In one aspect, a breast cancer that is to be treated is classified as having metastasized to a location selected from the group consisting of bone, lung, liver, or brain. In another aspect a breast cancer that is to be treated is classified according to a characteristic selected from the group consisting of metastatic, localized, regional, local-regional, locally advanced, distant, multicentric, bilateral, ipsilateral, contralateral, newly diagnosed, recurrent, and inoperable.

In one aspect, a compound of formula III, IIIa, IVa, IVb, Va, or Vb may be used to treat or prevent a cell proliferative disorder of the breast, or to treat or prevent breast cancer, in a subject having an increased risk of developing breast cancer relative to the population at large. In one aspect, a subject with an increased risk of developing breast cancer relative to the population at large is a female subject with a family history or personal history of breast cancer. In another aspect, a subject with an increased risk of developing breast cancer relative to the population at large is a female subject having a germ-line or spontaneous mutation in BRCA1 or BRCA2, or both. In one aspect, a subject with an increased risk of developing breast cancer relative to the population at large is a female subject with a family history of breast cancer and a germ-line or spontaneous mutation in BRCA1 or BRCA2, or both. In another aspect, a subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. In one aspect, a subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

In another aspect, a breast cancer that is to be treated has been histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. In another aspect, a breast cancer that is to be treated has been assigned a tumor grade according to the International Consensus Panel on the Treatment of Breast Cancer selected from the group consisting of grade 1, grade 1-2, grade 2, grade 2-3, or grade 3.

In one aspect, a cancer that is to be treated has been staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) has been assigned a stage of MX, M0, or M1. In another aspect, a cancer that is to be treated has been staged according to an American Joint Committee on Cancer (AJCC) classification as Stage I, Stage IIA, Stage IIB, Stage IIIA, Stage IIIB, Stage IIIC, or Stage IV. In another aspect, a cancer that is to be treated has been assigned a grade according to an AJCC classification as Grade GX (e.g., grade cannot be assessed), Grade 1, Grade 2, Grade 3 or Grade 4. In another aspect, a cancer that is to be treated has been staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

In one aspect, a cancer that is to be treated includes a tumor that has been determined to be less than or equal to about 2 centimeters in diameter. In another aspect, a cancer that is to be treated includes a tumor that has been determined to be from about 2 to about 5 centimeters in diameter. In another aspect, a cancer that is to be treated includes a tumor that has been determined to be greater than or equal to about 3 centimeters in diameter. In another aspect, a cancer that is to be treated includes a tumor that has been determined to be greater than 5 centimeters in diameter. In another aspect, a cancer that is to be treated is classified by microscopic appearance as well differentiated, moderately differentiated, poorly differentiated, or undifferentiated. In another aspect, a cancer that is to be treated is classified by microscopic appearance with respect to mitosis count (e.g., amount of cell division) or nuclear pleiomorphism (e.g., change in cells). In another aspect, a cancer that is to be treated is classified by microscopic appearance as being associated with areas of necrosis (e.g., areas of dying or degenerating cells). In one aspect, a cancer that is to be treated is classified as having an abnormal karyotype, having an abnormal number of chromosomes, or having one or more chromosomes that are abnormal in appearance. In one aspect, a cancer that is to be treated is classified as being aneuploid, triploid, tetraploid, or as having an altered ploidy. In one aspect, a cancer that is to be treated is classified as having a chromosomal translocation, or a deletion or duplication of an entire chromosome, or a region of deletion, duplication or amplification of a portion of a chromosome.

In one aspect, a cancer that is to be treated is evaluated by DNA cytometry, flow cytometry, or image cytometry. In one aspect, a cancer that is to be treated has been typed as having 10%, 20%, 30%, 40%, 50%, 60%, 70%, 80%, or 90% of cells in the synthesis stage of cell division (e.g., in S phase of cell division). In one aspect, a cancer that is to be treated has been typed as having a low S-phase fraction or a high S-phase fraction.

As used herein, a "normal cell" is a cell that cannot be classified as part of a "cell proliferative disorder." In one aspect, a normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of formula III, IIIa, IVa, IVb, Va, or Vb that has been or will be tested in one or more in vitro or in vivo biological assays, in order to determine if that compound is likely to elicit a desired biological or medical response in a cell, tissue, system, animal or human that is being sought by a researcher or clinician. In one aspect, a candidate compound is a compound of formula III or IIIa; in another aspect, a candidate compound is a compound of formula IVa, IVb, Va, or Vb. In a preferred aspect, the biological or medical response is treatment of cancer. In another aspect, the biological or medical response is treatment or prevention of a cell proliferative disorder. In one aspect, in vitro or in vivo biological assays include, but are not limited to, enzymatic activity assays, electrophoretic mobility shift assays, reporter gene assays, in vitro cell viability assays, and the assays.

As used herein, "monotherapy" refers to administration of a single active or therapeutic compound to a subject in need thereof. Preferably, monotherapy will involve administration of a therapeutically effective amount of an active compound. For example, cancer monotherapy with (±)-cis-3-(5,6-dihydro-4H-pyrrolo[3,2,1-ij]quinolin-1-yl)-4-(1H-indol-3-yl) pyrrolidine-2,5-dione comprises administration of a therapeutically effective amount of (±)-cis-3-(5,6-dihydro-4H-pyrrolo[3,2,1-ij]quinolin-1-yl)-4-(1H-indol-3-yl) pyrrolidine-2,5-dione, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, montherapy with a compound of formula III, IIIa, IVa, IVb, Va, or Vb is more effective than combination therapy in inducing a desired biological effect. Monotherapeutic effectiveness of the compounds of of formula III, IIIa, IVa, IVb, Va, or Vb is shown in PCT Publication No. WO 2006/086484.

As used herein, "treating" describes the management and care of a patient for the purpose of combating a disease, condition, or disorder and includes decreasing or alleviating the symptoms or complications, or eliminating the disease, condition or disorder.

As used herein, "preventing" describes stopping the onset of the symptoms or complications of the disease, condition or disorder.

In one aspect, treating cancer results in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. In a preferred aspect, size of a tumor may be measured as a diameter of the tumor.

In another aspect, treating cancer results in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

In another aspect, treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. In a preferred aspect, number of tumors may be measured by counting tumors visible to the naked eye or at a specified magnification. In a preferred aspect, the specified magnification is 2×, 3×, 4×, 5×, 10×, or 50×.

In another aspect, treating cancer results in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. In a preferred aspect, the number of metastatic lesions may be measured by counting metastatic lesions visible to the naked eye or at a specified magnification. In a preferred aspect, the specified magnification is 2×, 3×, 4×, 5×, 10×, or 50×.

In another aspect, treating cancer results in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in increase in average survival time of a population of treated subjects in comparison to a population receiving monotherapy with a drug that is not a compound of formula III, IIIa, IVa, IVb, Va, or Vb, or a pharmaceutically acceptable salt, prodrug, metabolite, analog or derivative thereof. Preferably, the average survival time is increased by more than 30 days;

more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in a decrease in the mortality rate of a population of treated subjects in comparison to a population receiving carrier alone. In another aspect, treating cancer results in a decrease in the mortality rate of a population of treated subjects in comparison to an untreated population. In a further aspect, treating cancer results a decrease in the mortality rate of a population of treated subjects in comparison to a population receiving monotherapy with a drug that is not a compound of formula III, IIIa, IVa, IVb, Va, or Vb, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound. In another preferred aspect, a decrease in the mortality rate of a population may also be measured, for example, by calculating for a population the average number of disease-related deaths per unit time following completion of a first round of treatment with an active compound.

In another aspect, treating cancer results in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. In a preferred aspect, tumor growth rate is measured according to a change in tumor diameter per unit time.

In another aspect, treating cancer results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. In a preferred aspect, tumor regrowth is measured, for example, by measuring an increase in the diameter of a tumor after a prior tumor shrinkage that followed treatment. In another preferred aspect, a decrease in tumor regrowth is indicated by failure of tumors to reoccur after treatment has stopped.

In another aspect, treating or preventing a cell proliferative disorder results in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. In a preferred aspect, the rate of cellular proliferation is measured, for example, by measuring the number of dividing cells in a tissue sample per unit time.

In another aspect, treating or preventing a cell proliferative disorder results in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. In a preferred aspect, the proportion of proliferating cells is measured, for example, by quantifying the number of dividing cells relative to the number of nondividing cells in a tissue sample. In another preferred aspect, the proportion of proliferating cells is equivalent to the mitotic index.

In another aspect, treating or preventing a cell proliferative disorder results in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. In a preferred aspect, size of an area or zone of cellular proliferation may be measured as a diameter or width of an area or zone of cellular proliferation.

In another aspect, treating or preventing a cell proliferative disorder results in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. In one aspect, an abnormal cellular morphology is measured by microscopy, e.g., using an inverted tissue culture microscope. In one aspect, an abnormal cellular morphology takes the form of nuclear pleiomorphism.

As used herein, the term "selectively" means tending to occur at a higher frequency in one population than in another population. In one aspect, the compared populations are cell populations. In a preferred aspect, a compound of formula III, IIIa, IVa, IVb, Va, or Vb, or a pharmaceutically acceptable salt, prodrug, metabolite, analog or derivative thereof, acts selectively on a cancer or precancerous cell but not on a normal cell. In another preferred aspect, a compound of formula III, IIIa, IVa, IVb, Va, or Vb, or a pharmaceutically acceptable salt, prodrug, metabolite, analog or derivative thereof, acts selectively to modulate one molecular target (e.g., c-Met) but does not significantly modulate another molecular target (e.g., Protein Kinase C). In another preferred aspect, the invention provides a method for selectively inhibiting the activity of an enzyme, such as a kinase. Preferably, an event occurs selectively in population A relative to population B if it occurs greater than two times more frequently in population A as compared to population B. More preferably, an event occurs selectively if it occurs greater than five times more frequently in population A. More preferably, an event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

In a preferred aspect, a compound of formula III, IIIa, IVa, IVb, Va, or Vb or a pharmaceutically acceptable salt, prodrug, metabolite, analog or derivative thereof, modulates the activity of a molecular target (e.g., c-Met). In one aspect, modulating refers to stimulating or inhibiting an activity of a molecular target. Preferably, a compound of formula III, IIIa, IVa, IVb, Va, or Vb modulates the activity of a molecular target if it stimulates or inhibits the activity of the molecular target by at least 2-fold relative to the activity of the molecular target under the same conditions but lacking only the presence of said compound. More preferably, a compound of formula III, IIIa, IVa, IVb, Va, or Vb modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

In one aspect, a compound of formula III, IIIa, IVa, IVb, Va, or Vb, or a pharmaceutically acceptable salt, prodrug, metabolite, analog or derivative thereof, does not significantly modulate the activity of a molecular target if the addition of the compound does not stimulate or inhibit the activity of the molecular target by greater than 10% relative to the activity of the molecular target under the same conditions but lacking only the presence of said compound. In a preferred aspect, a compound of formula III, IIIa, IVa, IVb, Va, or Vb does not significantly modulate the activity of Protein Kinase C.

As used herein, the term "isozyme selective" means preferential inhibition or stimulation of a first isoform of an enzyme in comparison to a second isoform of an enzyme (e.g., preferential inhibition or stimulation of a kinase isozyme alpha in comparison to a kinase isozyme beta). Preferably, a compound of formula III, IIIa, IVa, IVb, Va, or Vb demonstrates a minimum of a four fold differential, preferably a ten fold differential, more preferably a fifty fold differential, in the dosage required to achieve a biological effect. Preferably, a compound of formula III, IIIa, IVa, IVb, Va, or Vb demonstrates this differential across the range of inhibition, and the differential is exemplified at the $IC_{50}$, i.e., a 50% inhibition, for a molecular target of interest.

In a preferred embodiment, administering a compound of formula III, IIIa, IVa, IVb, Va, or Vb, or a pharmaceutically acceptable salt, prodrug, metabolite, analog or derivative thereof, to a cell or a subject in need thereof results in modulation (i.e., stimulation or inhibition) of an activity of c-Met. As used herein, an activity of c-Met refers to any biological function or activity that is carried out by c-Met. For example, a function of c-Met includes phosphorylation of downstream target proteins. Other functions of c-Met include autophosphorylation, binding of adaptor proteins such as Gab-1, Grb-2, Shc, SHP2 and c-Cbl, and activation of signal transducers such as Ras, Src, PI3K, PLC-γ, STATs, ERK1 and 2 and FAK. c-Met knockdown has been shown to inhibit cancer cell growth in a cell-type-specific manner. MDA-MB-231, NCI-H661, NCI-H441, MIA PaCa-2, HT29 and MKN-45 human cancer cells. c-Met knockdown induces caspase-dependent apoptosis in a cell type-specific manner. Thus, the present invention is directed to the treatment of cell proliferative disorders where the cells express c-Met at high levels or express active c-Met.

In a preferred embodiment, administering a compound of formula III, IIIa, IVa, IVb, Va, or Vb, or a pharmaceutically acceptable salt, prodrug, metabolite, analog or derivative thereof, to a cell or a subject in need thereof results in modulation (i.e., stimulation or inhibition) of an activity of ERK 1 or ERK 2, or both. As used herein, an activity of ERK 1 or ERK 2 refers to any biological function or activity that is carried out by ERK 1 or ERK 2. For example, a function of ERK 1 or ERK 2 includes phosphorylation of downstream target proteins.

In one aspect, activating refers to placing a composition of matter (e.g., protein or nucleic acid) in a state suitable for carrying out a desired biological function. In one aspect, a composition of matter capable of being activated also has an unactivated state. In one aspect, an activated composition of matter may have an inhibitory or stimulatory biological function, or both.

In one aspect, elevation refers to an increase in a desired biological activity of a composition of matter (e.g., a protein or a nucleic acid). In one aspect, elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. In one aspect, a cell cycle checkpoint regulator is a protein. In another aspect, a cell cycle checkpoint regulator is not a protein.

In one aspect, treating cancer or a cell proliferative disorder results in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. In one aspect, number of cells in a population is measured by fluorescence activated cell sorting (FACS). In another aspect, number of cells in a population is measured by immunofluorescence microscopy. In another aspect, number of cells in a population is measured by light microscopy. In another aspect, methods of measuring cell death are as shown in Li et al., (2003) *Proc Natl Acad Sci USA*. 100(5): 2674-8. In an aspect, cell death occurs by apoptosis.

In a preferred aspect, an effective amount of a compound of formula III, IIIa, IVa, IVb, Va, or Vb, or a pharmaceutically acceptable salt, prodrug, metabolite, analog or derivative thereof is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

In one aspect, contacting a cell with a compound of formula III, IIIa, IVa, IVb, Va, or Vb, or a pharmaceutically acceptable salt, prodrug, metabolite, analog or derivative thereof, induces or activates cell death selectively in cancer cells. Preferably, administering to a subject in need thereof a compound of formula III, IIIa, IVa, IVb, Va, or Vb, or a pharmaceutically acceptable salt, prodrug, metabolite, analog or derivative thereof, induces or activates cell death selectively in cancer cells. In another aspect, contacting a cell with a compound of formula III, IIIa, IVa, IVb, Va, or Vb, or a pharmaceutically acceptable salt, prodrug, metabolite, analog or derivative thereof, induces cell death selectively in one or more cells affected by a cell proliferative disorder. Preferably, administering to a subject in need thereof a compound of formula III, IIIa, IVa, IVb, Va, or Vb, or a pharmaceutically acceptable salt, prodrug, metabolite, analog or derivative thereof, induces cell death selectively in one or more cells affected by a cell proliferative disorder. In a preferred aspect, the present invention relates to a method of treating or preventing cancer by administering a compound of formula III, IIIa, IVa, IVb, Va, or Vb, or a pharmaceutically acceptable salt, prodrug, metabolite, analog or derivative thereof to a subject in need thereof, where administration of the compound of formula III, IIIa, IVa, IVb, Va, or Vb, or a pharmaceutically acceptable salt, prodrug, metabolite, analog or derivative thereof results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose. One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3d ed.), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18th edition (1990). These texts can, of course, also be referred to in making or using an aspect of the invention.

2. Pyrroloquinolinyl-pyrrole-2,5-diones and pyrroloquinolinyl-pyrrolidine-2,5-diones The pyrroloquinolinyl-pyrrole-2,5-dione compounds of formula III and IIIa are:

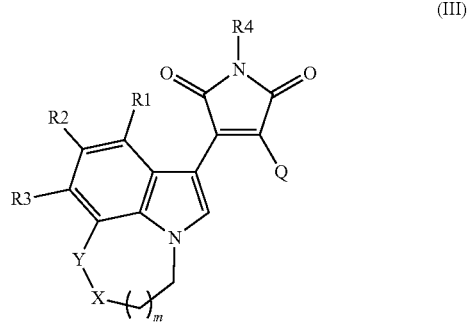

(III)

where:

R1, R2 and R3 are independently selected from the group consisting of hydrogen, F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, and —O—($C_3$-$C_9$) substituted cycloalkyl, aryl, heteroaryl, heterocyclyl;

R4 is independently selected from the group consisting of hydrogen, —($C_1$-$C_6$) alkyl, —CH$_2$R7;

R5, R6 are independently selected from the group consisting of hydrogen, and —($C_1$-$C_6$) alkyl;

R7 is independently selected from the group consisting of —O—P(=O)(OH)$_2$, —O—P(=O)(—OH)(—O—($C_1$-$C_6$) alkyl), —O—P(=O)(—O—($C_1$-$C_6$) alkyl)$_2$, —O—P(=O)(—OH)(—O—(CH$_2$)-phenyl), —O—P(=O)(—O—(CH$_2$)-phenyl)$_2$, a carboxylic acid group, an amino carboxylic acid group and a peptide;

Q is selected from the group consisting of aryl, heteroaryl, —O-aryl, —S-aryl, —O-heteroaryl, and —S-heteroaryl;

X is selected from the group consisting of —(CH$_2$)—, —(NR8)-, S, and O;

R8 is independently selected from the group consisting of hydrogen, —($C_1$-$C_6$) alkyl, —($C_1$-$C_6$) substituted alkyl, —($C_3$-$C_9$) cycloalkyl, —($C_3$-$C_9$) substituted cycloalkyl, and —O—($C_1$-$C_6$) alkyl, —C(=O)—O—($C_1$-$C_6$) alkyl and —C(=O)—O—($C_1$-$C_6$) substituted alkyl;

Y is selected from the group consisting of —(CH$_2$)— or a bond;

wherein said aryl, heteroaryl, —O-aryl, —S-aryl, —O-heteroaryl, and —S-heteroaryl groups may be substituted with one or more substituents independently selected from the group consisting of F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, —O—($C_3$-$C_9$) substituted cycloalkyl, -aryl, -aryl-($C_1$-$C_6$) alkyl, -aryl-O—($C_1$-$C_6$) alkyl, —O-aryl, —O—($C_1$-$C_4$) alkyl-aryl, heteroaryl, heterocyclyl, —O—($C_1$-$C_4$) alkyl-heterocycle, and —(S(=O)$_2$)—($C_1$-$C_6$) alkyl; and m is 1 or 2.

For the compound of formula IIIa, Q is selected from the group consisting of aryl, heteroaryl, —O-aryl, —S-aryl, —O-heteroaryl, and —S-heteroaryl, provided that when R4 is hydrogen, or (C$_1$-C$_4$) alkyl, Q is not 3-indolyl or substituted 3-indolyl.

The pyrroloquinolinyl-pyrrolidine-2,5-dione compounds of formula IVa, IVb, Va, or Vb, are:

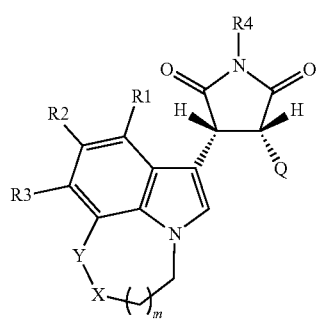
(IVa)

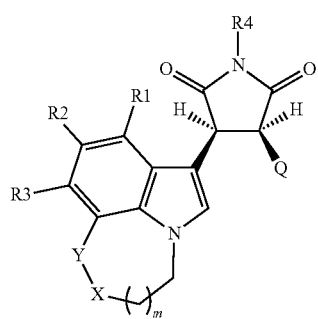
(IVb)

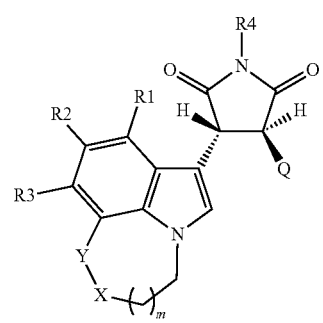
(Va)

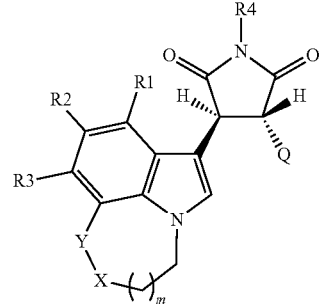
(Vb)

where:

R1, R2 and R3 are independently selected from the group consisting of hydrogen, F, Cl, Br, I, —NR5R6, —(C$_1$-C$_6$) alkyl, —(C$_1$-C$_6$) substituted alkyl, —(C$_3$-C$_9$) cycloalkyl, —(C$_3$-C$_9$) substituted cycloalkyl, —O—(C$_1$-C$_6$) alkyl, —O—(C$_1$-C$_6$) substituted alkyl, —O—(C$_3$-C$_9$) cycloalkyl, and —O—(C$_3$-C$_9$) substituted cycloalkyl, aryl, heteroaryl, heterocyclyl;

R4 is independently selected from the group consisting of hydrogen, —(C$_1$-C$_6$) alkyl, —CH$_2$R7;

R5, R6 are independently selected from the group consisting of hydrogen, and —(C$_1$-C$_6$) alkyl;

R7 is independently selected from the group consisting of —O—P(=O)(OH)$_2$, —O—P(=O)(—OH)(—O—(C$_1$-C$_6$) alkyl), —O—P(=O)(—O—(C$_1$-C$_6$) alkyl)$_2$, —O—P(=O)(—OH) (—O—(CH$_2$)-phenyl), —O—P(=O)(—O—(CH$_2$)-phenyl)$_2$, a carboxylic acid group, an amino carboxylic acid group and a peptide;

Q is selected from the group consisting of aryl, heteroaryl, —O-aryl, —S-aryl, —O-heteroaryl, and —S-heteroaryl;

X is selected from the group consisting of —(CH$_2$)—, —(NR8)-, S, and O;

R8 is independently selected from the group consisting of hydrogen, —(C$_1$-C$_6$) alkyl, —(C$_1$-C$_6$) substituted alkyl, —(C$_3$-C$_9$) cycloalkyl, —(C$_3$-C$_9$) substituted cycloalkyl, and —O—(C$_1$-C$_6$) alkyl, —C(=O)—O—(C$_1$-C$_6$) alkyl and —C(=O)—O—(C$_1$-C$_6$) substituted alkyl;

Y is selected from the group consisting of —(CH$_2$)— or a bond;

wherein said aryl, heteroaryl, —O-aryl, —S-aryl, —O-heteroaryl, and —S-heteroaryl groups may be substituted with one or more substituents independently selected from the group consisting of F, Cl, Br, I, —NR5R6, —(C$_1$-C$_6$) alkyl, —(C$_1$-C$_6$) substituted alkyl, —(C$_3$-C$_9$) cycloalkyl, —(C$_3$-C$_9$) substituted cycloalkyl, —O—(C$_1$-C$_6$) alkyl, —O—(C$_1$-C$_6$) substituted alkyl, —O—(C$_3$-C$_9$) cycloalkyl, —O—(C$_3$-C$_9$) substituted cycloalkyl, -aryl, -aryl-(C$_1$-C$_6$) alkyl, -aryl-O—(C$_1$-C$_6$) alkyl, —O-aryl, —O—(C$_1$-C$_4$) alkyl-aryl, heteroaryl, heterocyclyl, —O—(C$_1$-C$_4$) alkyl-heterocycle, and —(S(=O)$_2$)—(C$_1$-C$_6$) alkyl; and m is 1 or 2.

2.1. Definitions

The term "alkyl" refers to radicals containing carbon and hydrogen, without unsaturation. Alkyl radicals can be straight or branched. Exemplary alkyl radicals include, without limitation, methyl, ethyl, propyl, isopropyl, hexyl, t-butyl, sec-butyl and the like. Akyl groups may be denoted by a range, thus, for example, a (C$_1$-C$_6$) alkyl group is an alkyl group having from one to six carbon atoms in the straight or branched alkyl backbone. Substituted and unsubstituted alkyl groups may independently be (C$_1$-C$_5$) alkyl, (C$_1$-C$_6$) alkyl, (C$_1$-C$_{10}$) alkyl, (C$_3$-C$_{10}$) alkyl, or (C$_5$-C$_{10}$) alkyl. Unless expressly stated, the term "alkyl" does not include "cycloalkyl."

A "cycloalkyl" group refers to a cyclic alkyl group having the indicated number of carbon atoms in the "ring portion," where the "ring portion" may consist of one or more ring structures either as fused, spiro, or bridged ring structures. For example, a C3 to C6 cycloalkyl group (e.g., (C$_3$-C$_6$) cycloalkyl) is a ring structure having between 3 and 6 carbon atoms in the ring. When no range is given, then cycloalkyl has between three and nine carbon atoms ((C$_3$-C$_9$) cycloalkyl) in the ring portion. Exemplary cycloalkyl groups include, but are not limited to cyclopropyl, cyclobutyl, cyclopentyl, cyclohexyl, cycloheptyl, and adamantyl. Preferred cycloalkyl groups have three, four, five, six, seven, eight, nine, or from three to nine carbon atoms in the ring structure.

The term substituted alkyl and substituted cycloalkyl, refer to alkyl and cycloalkyl groups, as defined above, substituted with one or more substituents independently selected from the group consisting of fluorine, aryl, heteroaryl, —O—($C_1$-$C_6$) alkyl, and —NR5R6, where R5 and R6 are independently selected from the group consisting of hydrogen and —($C_1$-$C_6$) alkyl.

The term "aryl" refers to an aromatic carbocyclic group, having one, two, or three aromatic rings. Exemplary aryl groups include, without limitation, phenyl, naphthyl, and the like. Aryl groups include one, two, or three aromatic rings structures fused with one or more additional nonaromatic carbocyclic or hetercyclic rings having from 4-9 members. Examples of fused aryl groups include benzocyclobutanyl, indanyl, tetrahydronapthylenyl, 1,2,3,4-tetrahydrophenanthrenyl, tetrahydroanthracenyl, 1,4-dihydro-1,4-methanonaphthalenyl, benzodioxolyl.

The term "heteroaryl" refers to a heteroaromatic (heteroaryl) group having one, two, or three aromatic rings containing from 1-4 heteroatoms (such as nitrogen, sulfur, or oxygen) in the aromatic ring. Heteroaryl groups include one, two, or three aromatic rings structures containing from 1-4 heteroatoms fused with one or more additional nonaromatic rings having from 4-9 members. Heteroaryl groups containing a single type of hetroatom in the aromatic ring are denoted by the type of hetero atom they contain, thus, nitrogen-containing heteroaryl, oxygen-containing heteroaryl and sulfur-containing heteroaryl denote heteroaromatic groups containing one or more nitrogen, oxygen or sulfur atoms respectively. Exemplary heteroaryl groups include, without limitation, pyridyl, pyrimidinyl, triazolyl, quinolyl, quinazolinyl, thiazolyl, benzo[b]thiophenyl, furanyl, imidazolyl, indolyl, and the like.

The terms "heterocyclyl" or "heterocycle" refers to either saturated or unsaturated, stable non-aromatic ring structures that may be fused, spiro or bridged to form additional rings. Each heterocycle consists of one or more carbon atoms and from one to four heteroatoms selected from the group consisting of nitrogen, oxygen and sulfur. "Heterocyclyl" or "heterocycle" include stable non-aromatic 3-7 membered monocyclic heterocyclic ring structures and 8-11 membered bicyclic heterocyclic ring structures. A heterocyclyl radical may be attached at any endocyclic carbon or nitrogen atom that results in the creation of a stable structure. Preferred heterocycles include 3-7 membered monocyclic heterocycles (more preferably 5-7-membered monocyclic heterocycles) and 8-10 membered bicyclic heterocycles. Examples of such groups include piperidinyl, piperazinyl, pyranyl, pyrrolidinyl, morpholinyl, thiomorpholinyl, oxopiperidinyl, oxopyrrolidinyl, oxoazepinyl, azepinyl, isoxozolyl, tetrahydropyranyl, tetrahydrofuranyl, dioxolyl, dioxinyl, oxathiolyl, dithiolyl, sulfolanyl, dioxanyl, dioxolanyl, tetrahydrofurodihydrofuranyl, tetrahydropyranodihydro-furanyl, dihydropyranyl, tetrahydrofurofuranyl, tetrahydropyranofuran, quinuclidinyl (1-azabicyclo[2.2.2]octanyl) and tropanyl (8-methyl-8-azabicyclo[3.2.1]octanyl).

For the purpose of the Q substituent, the term "substituted 3-indolyl" refers to a 3-indolyl group substituted with one or more substituents selected from the group consisting of: F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, —O—($C_3$-$C_9$) substituted cycloalkyl, -aryl, -aryl-($C_1$-$C_6$) alkyl, -aryl-O—($C_1$-$C_6$) alkyl, —O-aryl, —O—($C_1$-$C_4$) alkyl-aryl, heteroaryl, heterocyclyl, —O—($C_1$-$C_4$) alkyl-heterocycle, and —(S(=O)$_2$)—($C_1$-$C_6$) alkyl; where R5, R6 are independently selected from the group consisting of hydrogen, and —($C_1$-$C_6$) alkyl.

For the purposes of the R7 substituent, the term "carboxylic acid group" refers to a group of the form —O—C(=O)—($C_1$-$C_6$) alkyl, —O—C(=O)—($C_3$-$C_9$) cycloalkyl, —O—C(=O)-aryl, —O—C(=O)-heteroaryl, —O—C(=O)-heterocycle, —O—C(=O)—($C_1$-$C_6$) alkyl-aryl, —O—C(=O)—($C_1$-$C_6$) alkyl-heteroaryl, or —O—C(=O)—($C_1$-$C_6$) alkyl-heterocycle. Included in "carboxylic acid group" are groups of the form —O—C(=O)—($C_1$-$C_6$) alkyl, —O—C(=O)—($C_3$-$C_9$) cycloalkyl, —O—C(=O)-aryl, —O—C(=O)-heteroaryl, —O—C(=O)-heterocycle, —O—C(=O)—($C_1$-$C_6$) alkyl-aryl, —O—C(=O)—($C_1$-$C_6$) alkyl-heteroaryl, or —O—C(=O)—($C_1$-$C_6$) alkyl-heterocycle substituted with one or more substituent independently selected from the group consisting of: F, Cl, Br, I, —OH, —SH, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —S—($C_1$-$C_6$) alkyl, —O—($C_3$-$C_9$) cycloalkyl, —O—($C_3$-$C_9$) substituted cycloalkyl, -aryl, —O-aryl, —O—($C_1$-$C_4$) alkyl-aryl, heteroaryl, heterocyclyl, —O—($C_1$-$C_4$) alkyl-heterocycle, —(S(=O)$_2$)—($C_1$-$C_6$) alkyl, —NH—C(=NH)—NH$_2$ (i.e., guanido), —COOH, and —C(=O)—NR5R6, where R5 and R6 are independently selected from the group consisting of hydrogen, and —($C_1$-$C_6$) alkyl. In addition, for the purposes of the R7 substituent the term "amino carboxylic acid group" refers to a carboxylic acid group, including carboxylic acid groups substituted with one or more of the above-stated substituents, which bears one or more independently selected amino groups of the form —NR5R6 where R5 and R6 are independently selected from the group consisting of hydrogen and (C1-C6) alkyl.

In one embodiment of this invention, R7 is an alpha amino or imino acid, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or stereoisomers or racemic mixtures thereof. In another embodiment the of the invention, R7 is alpha amino or imino acid selected from the group consisting of L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and L-valine.

For the purposes of the R7 substituent, the term "peptide" refers to a dipeptide, tripeptide, tetrapeptide or pentapeptide, which release two, three, four, or five amino or imino acids (e.g., proline) respectively upon hydrolysis. For the purpose of R7, peptides are linked to the remainder of the molecule through an ester linkage. In one embodiment, peptides of R7 are comprised of alpha amino or imino acid, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or stereoisomers or racemic mixtures thereof; and in a more preferred version of this embodiment, the carboxyl group involved in the ester linkage is the carboxyl terminal COOH group of the peptide, as opposed to a side chain carboxyl. In another embodiment the of the invention, R7 is alpha amino or imino acid selected from the group consisting of L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and L-valine; and in a more preferred version of this preferred embodiment, the carboxyl group involved in the ester linkage is the carboxyl terminal COOH group of the peptide, as opposed to a side chain carboxyl.

2.2. Preferred Compounds

Included in the preferred embodiments are compounds of formula III, IIIa, IVa, IVb, Va, or Vb, wherein Q is selected from the group consisting of aryl, heteroaryl, —O-aryl, —S-aryl, —O-heteroaryl, and —S-heteroaryl, provided that Q is not 3-indolyl or a substituted 3-indolyl. In other preferred embodiments Q is selected from the group consisting of aryl, heteroaryl, —O-aryl, —S-aryl, —O-heteroaryl, and —S-heteroaryl, provided that when R4 is hydrogen, cycloalkyl, or alkyl, Q is not 3-indolyl or a substituted 3-indolyl. In still other preferred embodiments Q is selected from the group consisting of aryl, heteroaryl, —O-aryl, —S-aryl, —O-heteroaryl, and —S-heteroaryl, provided that when R4 is hydrogen, $(C_3-C_4)$ cycloalkyl, or $(C_1-C_4)$ alkyl, Q is not 3-indolyl or substituted 3-indolyl. In another preferred embodiment Q is 3-indolyl or a substituted 3-indolyl provided that R4 is not hydrogen, cycloalkyl, or alkyl. In still another preferred embodiment Q is 3-indolyl or a substituted 3-indolyl provided that R4 is not hydrogen, $(C_3-C_4)$ cycloalkyl, or $(C_1-C_4)$ alkyl.

Other preferred embodiments include compounds of formula III, IIIa, IVa, IVb, Va, or Vb where R4 is —CH$_2$R7. These compounds may serve as prodrug forms of the corresponding compounds of formula III, IIIa, IVa, IVb, Va, or Vb where R4 is H. The prodrug form is cleaved by hydrolysis to release the corresponding compound where R4 is H. The hydrolysis may occur by enzymatic or nonenzymatic routes that produce the corresponding hydroxymethylene derivative, which upon subsequent hydrolysis, result in the release of compounds where R4 is H. In one such preferred embodiment R4 is —CH$_2$R7, where R7 is —O—P(=O)(OH)$_2$, —O—P(=O)(—OH)(—O—(C$_1$-C$_6$)alkyl), or —O—P(=O)(—O—(C$_1$-C$_6$)alkyl)$_2$. In one embodiment where R7 is —O—P(=O)(—O—(C$_1$-C$_6$)alkyl)$_2$, the alkyl groups are independently selected. In another preferred embodiment, R4 is —CH$_2$R7, where R7 is a carboxylic acid group or an amino carboxylic acid group. In still another preferred embodiment R7 is a peptide; where in a more preferred embodiment the peptide is linked through an ester bond formed with the carboxyl terminal COOH group of the peptide chain to the remainder of the compound. In other preferred separate and independent embodiments of compounds of formula III, IIIa, IVa, IVb, Va, or Vb where R4 is —CH$_2$R7 and R7 is a peptide, the peptide may be a dipeptide, a tripeptide, a tetrapeptide or a pentapeptide. Preferred amino acid compositions for peptides of the R7 functionality are described above.

Embodiments of compounds of formula III, IIIa, IVa, IVb, Va, or Vb include those where X is selected from the group consisting of —(NR8)-, S, and O, where R8 is independently selected from the group consisting of hydrogen, —(C$_1$-C$_6$) alkyl, —(C$_1$-C$_6$) substituted alkyl, —(C$_3$-C$_9$) cycloalkyl, —(C$_3$-C$_9$) substituted cycloalkyl, and —O—(C$_1$-C$_6$) alkyl. Other embodiments of compounds of formula III, IIIa, IVa, IVb, Va, or Vb include those where X is —CH$_2$—. In other embodiments of compounds of formula III, IIIa, IVa, IVb, Va, or Vb, X is oxygen (O). In other embodiments of compounds of formula III, IIIa, IVa, IVb, Va, or Vb, X is sulfur (S). In still other embodiments of compounds of formula III, IIIa, IVa, IVb, Va, or Vb, X is —(NR8)-, where R8 is independently selected from the group consisting of hydrogen, —(C$_1$-C$_6$) alkyl, —(C$_1$-C$_6$) substituted alkyl, —(C$_3$-C$_9$) cycloalkyl, —(C$_3$-C$_9$) substituted cycloalkyl, and —O—(C$_1$-C$_6$) alkyl.

Other preferred embodiments of the invention include compounds of formula III or IIIa, where Q is a heteroaryl or an optionally substituted heteroaryl group. In four separate alternative preferred embodiments of compounds of formula III or IIIa, Q is an optionally substituted monocyclic heteroaryl group, an optionally substituted bicyclic heteroaryl group, an optionally substituted bicyclic heteroaryl group with the proviso that the bicyclic heteroaryl group is not an indolyl group or a substituted indolyl, or an optionally substituted tricyclic heteroaryl group. Optional substituents, when present, are independently selected from those recited for aryl, heteroaryl, —O-aryl, —S-aryl, —O-heteroaryl, and —S-heteroaryl.

Included in the preferred embodiments of the invention are compounds of formula IVa, IVb, Va, or Vb, where Q is a heteroaryl or an optionally substituted heteroaryl group. In four separate alternative preferred embodiments of compounds of formula IVa, IVb, Va, or Vb, Q is an optionally substituted monocyclic heteroaryl group, an optionally substituted bicyclic heteroaryl group, an optionally substituted bicyclic heteroaryl group with the proviso that the bicyclic heteroaryl group is not indolyl, or an optionally substituted tricyclic heteroaryl group. In a more preferred embodiment, Q is an optionally substituted nitrogen-containing heteroaryl group. In a related embodiment, Q is an optionally substituted indolyl. Optional substituents, when present are independently selected from those recited for aryl, heteroaryl, —O-aryl, —S-aryl, —O-heteroaryl, and —S-heteroaryl.

Preferred embodiments of the invention include mixtures of compounds of formula IVa and IVb, including racemic mixtures. In another preferred embodiment, the compounds of formula IVa and IVb are the separate enantiomers of (±)-cis-3-(5,6-dihydro-4H-pyrrolo[3,2,1-ij]quinolin-1-yl)-4-(1H-indol-3-yl) pyrrolidine-2,5-dione. In this embodiment the preparation of (±)-cis-3-(5,6-dihydro-4H-pyrrolo[3,2,1-ij]quinolin-1-yl)-4-(1H-indol-3-yl) pyrrolidine-2,5-dione is prepared as a mixture beginning with the starting materials 1,2,3,4-tetrahydroquinoline and indole-3-acetamide. The 1,2,3,4-tetrahydroquinoline is converted into 5,6-dihydro-4H-pyrrolo[3,2,1-ij]quinolin-1-yl) oxoacetic acid methyl ester as described in Example 1, steps 1-5. The 5,6-dihydro-4H-pyrrolo[3,2,1-ij]quinolin-1-yl) oxoacetic acid methyl ester is reacted with indole-3-acetamide as described in Example 1, step 6, to yield 3-(5,6-dihydro-4H-pyrrolo[3,2,1-ij]quinolin-1-yl)-4-(1H-indol-3-yl) pyrrole-2,5-dione. The mixture of (±)-cis-3-(5,6-dihydro-4H-pyrrolo[3,2,1-ij]quinolin-1-yl)-4-(1H-indol-3-yl) pyrrolidine-2,5-dione is then prepared by catalytic hydrogenation as described in Example 2 using Procedure B.

Preferred embodiments of the invention also include mixtures of compounds of formula Va and Vb, including racemic mixtures. In another preferred embodiment, the compounds of Va and Vb are the separate enantiomers of (±)-trans-3-(5,6-dihydro-4H-pyrrolo[3,2,1-ij]quinolin-1-yl)-4-(1H-indol-3-yl) pyrrolidine-2,5-dione. In this embodiment, the compounds are prepared as a mixture by first preparing (±)-cis-3-(5,6-dihydro-4H-pyrrolo[3,2,1-ij]quinolin-1-yl)-4-(1H-indol-3-yl) pyrrolidine-2,5-dione, as described above. The mixture of cis compounds is then treated with a mixture of potassium tert-butoxide in tert-butanol to obtain a mixture of (±)-trans-3-(5,6-dihydro-4H-pyrrolo[3,2,1-ij]quinolin-1-yl)-4-(1H-indol-3-yl) pyrrolidine-2,5-dione as described in Example 3.

All stereoisomers of the compounds of the instant invention are contemplated, either in admixture or in pure or substantially pure form, including crystalline forms of racemic mixtures and crystalline forms of individual isomers. The definition of the compounds according to the invention embraces all possible stereoisomers (e.g., the R and S configurations for each asymmetric center) and their mixtures. It very particularly embraces the racemic forms and the isolated optical isomers having a specified activity. The racemic forms can be resolved by physical methods, such as, for example, fractional crystallization, separation or crystallization of diastereomeric derivatives, separation by chiral column chromatography or supercritical fluid chromatography. The individual optical isomers can be obtained from the racemates by conventional methods, such as, for example, salt formation with an optically active acid followed by crystallization. Furthermore, all geometric isomers, such as E- and Z-configurations at a double bond, are within the scope of the invention unless otherwise stated. Certain compounds of this invention may exist in tautomeric forms. All such tautomeric forms of the compounds are considered to be within the scope of this invention unless otherwise stated. The present invention also includes one or more regioisomeric mixtures of an analog or derivative.

As used herein, the term "salt" is a pharmaceutically acceptable salt and can include acid addition salts including hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as $Na^+$, $K^+$, $Li^+$, alkali earth metal salts such as Mg or Ca, or organic amine salts.

As used herein, the term "metabolite" means a product of metabolism of a compound of formula III, IIIa, IVa, IVb, Va, or Vb, or a pharmaceutically acceptable salt, analog or derivative thereof, that exhibits a similar activity in vivo to said a compound of formula III, IIIa, IVa, IVb, Va, or Vb.

As used herein, the term "prodrug" means a compound of formula III, IIIa, IVa, IVb, Va, or Vb covalently linked to one or more pro-moieties, such as an amino acid moiety or other water solubilizing moiety. A compound of formula III, IIIa, IVa, IVb, Va, or Vb may be released from the pro-moiety via hydrolytic, oxidative, and/or enzymatic release mechanisms.

In an embodiment, a prodrug composition of the present invention exhibits the added benefit of increased aqueous solubility, improved stability, and improved pharmacokinetic profiles. The pro-moiety may be selected to obtain desired prodrug characteristics. For example, the pro-moiety, e.g., an amino acid moiety or other water solubilizing moiety such as phosphate within R4, may be selected based on solubility, stability, bioavailability, and/or in vivo delivery or uptake.

3. The Synthesis of Pyrroloquinolinyl-pyrrole-2,5-diones and pyrroloquinolinyl-pyrrolidine-2,5-diones Standard synthetic methods and procedures for the preparation of organic molecules and functional group transformations and manipulations including the use of protective groups can be obtained from the relevant scientific literature or from standard reference textbooks in the field.

Although not limited to any one or several sources, recognized reference textbooks of organic synthesis include: Smith, M. B.; March, J. March's Advanced Organic Chemistry: Reactions, Mechanisms, and Structure, 5$^{th}$ ed.; John Wiley & Sons: New York, 2001; and Greene, T. W.; Wuts, P. G. M. Protective Groups in Organic Synthesis, 3$^{rd}$; John Wiley & Sons: New York, 1999. The following descriptions of synthetic methods are designed to illustrate, but not limit, general procedures for the preparation of the compounds of formula III, IIIa, IVa, IVb, Va, or Vb.

3.1 General Procedures for the Synthesis of pyrroloquinolinyl-pyrrole-2,5-dione and pyrroloquinolinyl-pyrrolidine-2,5-diones where R4 is Hydrogen The present invention provides for pyrroloquinolinyl-pyrrole-2,5-dione compounds of formula III, IIIa, IVa, IVb, Va, or Vb. The preparation of compounds of formula III, IIIa, IVa, IVb, Va, and Vb may be achieved by a series of reactions commencing with the reaction of a 5,6-dihydro-4H-pyrrolo[3,2,1-ij]quinolin-1-yl) oxoacetic acid ester of formula I with an amide of formula II, to form a 3-(5,6-dihydro-4H-pyrrolo[3,2,1-ij]quinolin-1-yl)-4-(1H-indol-3-yl) pyrrole-2,5-dione of formula III, including compounds of formula IIIa, where R4 is hydrogen, as shown in Scheme 1.

Scheme 1

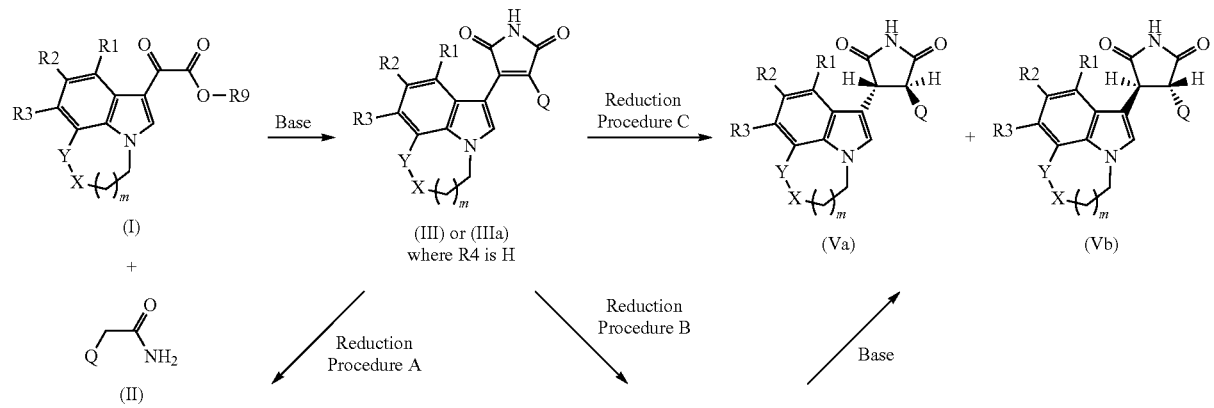

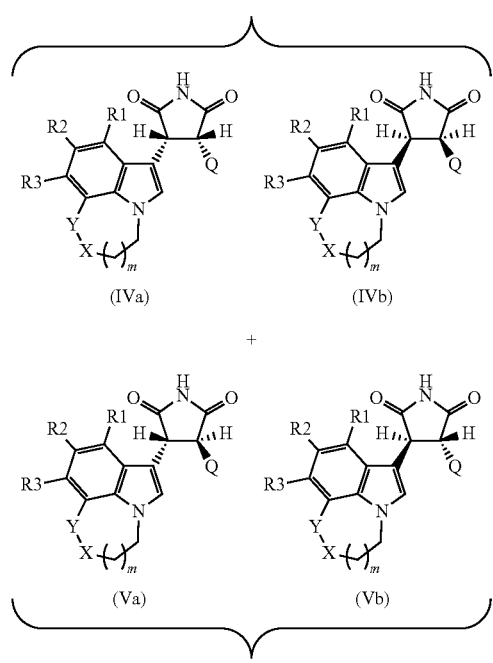
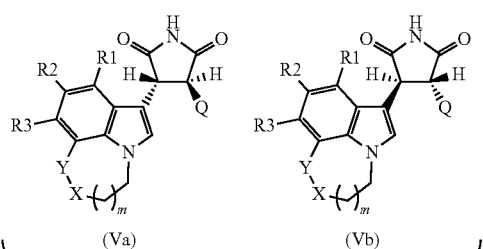
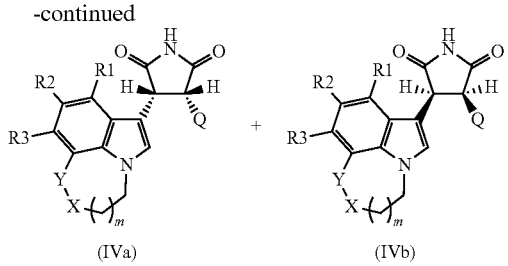

3.1.1. Synthesis of 3-(5,6-dihydro-4H-pyrrolo[3,2,1-ij]quinolin-1-yl)-4-(1H-indol-3-yl) pyrrole-2,5-diones of Formula III where R4 is Hydrogen The condensation of an ester of formula I and a compound of formula II to produce compounds of formula III, including compounds of formula IIIa, where R4 is hydrogen is conducted in any suitable anhydrous polar aprotic solvent including, but not limited to, tetrahydrofuran (THF), tetrahydropyran, diethyl ether and the like in the presence of base. For the purposes of the reaction, suitable esters of formula I include, but are not limited to, alkyl esters where R9 is a (C1-C4) alkyl group, and preferred esters include the methyl and ethyl esters. Suitable bases for the reaction include alkaline metal salts of low molecular weight alkyl alcohols, including, but not limited to, alkaline metal salts of methanol, ethanol, propanol, isopropanol, n-butanol, isobutanol, and tert-butanol. Preferred alkaline metal salts of low molecular weight alkyl alcohols include sodium and potassium salts, with potassium tert-butoxide (tBuOK) being the preferred base. Typically the reactions are conducted at 0° C. for 2 hours, however, both the time and temperature may be altered depending upon the specific substituents present on compounds of formula I and II, and the solvent employed. The reaction temperature may be varied from −78° C. to 37° C., and is preferably from −35° C. to 25° C., or more preferably from −15° C. to 10° C. Reaction times will generally vary inversely with the temperature employed, suitable times from about 15 minutes to 24 hours may be employed, more preferably, 30 minutes to 12 hours, and more preferably 1 to 6 hours.

3.1.2. Preparation of Compounds of Formula IVa, IVb, Va and Vb where R4 is Hydrogen Reduction of compounds of formula III and IIIa, where R4 is hydrogen to yield the corresponding 3-(5,6-dihydro-4H-pyrrolo[3,2,1-ij]quinolin-1-yl)-4-(1H-indol-3-yl) pyrrolidine-2,5-diones having formula IVa, IVb, Va, or Vb may be conducted employing a variety of procedures including, but not limited to, reduction with zinc-mercury (Procedure A), catalytic hydrogenation (Procedure B), and reduction with magnesium in methanol (Procedure C). As indicated in Scheme 1, depending on the reduction reaction and conditions chosen, the reaction will yield principally compounds of formula IVa and IVb, or principally compounds of formula Va and Vb, or alternatively a mixture of compounds of formula IVa, IVb, Va, and Vb.

Mixtures of compounds of formula IVa, IVb, Va, and Vb may be prepared by the direct reduction of compounds of formula III or IIIa with a zinc-mercury reducing agent. The reaction is generally carried out with fresh reducing agent prepared by mixing Zn powder with $HgCl_2$ deionized water followed by acidification with HCl. After drying, the solid reducing agent (zinc-mercury) is suitable for reduction of compounds of formula III or IIIa in refluxing dry ethanol under a dry HCl gas atmosphere as described in Example 2, Procedure A, for the reduction of 3-(5,6-dihydro-4H-pyrrolo[3,2,1-ij]quinolin-1-yl)-4-(1H-indol-3-yl) pyrrole-2,5-dione.

An alternative method of preparing pyrrolidine-2,5-diones is catalytic hydrogenation, which yields a mixture consisting principally of the (±)-cis pyrrolidine-2,5-diones of formula IVa and IVb. Catalytic hydrogenation of compounds of formula III or IIIa may be conducted in an anhydrous alcohol over a noble metal catalyst under 1 atmosphere of hydrogen for 48 hours. A variety of low molecular weight alkyl alcohols may be employed to conduct the reduction, including n-propyl alcohol, isopropyl alcohol, ethanol or methanol. Preferably the alcohol is ethanol or methanol, and most preferably methanol. A noble metal catalyst (e.g., platinum, palladium, rhodium, ruthenium etc.) on charcoal is preferred for the reduction of compounds of formula III or IIIa. In more preferred embodiments, the noble metal catalyst is palladium on activated charcoal. While reduction compounds of formula IIIa or III under 1 atmosphere of hydrogen at room temperature (25° C.) for 12-48 hours is generally suitable for preparation of pyrrolidine-2,5-diones, the pressure of hydrogen, reaction time, and the reaction temperature may be varied. Catalytic hydrogenation of 3-(5,6-dihydro-4H-pyrrolo[3,2,1-ij]quinolin-1-yl)-4-(1H-indol-3-yl) pyrrole-2,5-dione is described in Example 2, Procedure B.

Pyrrole-2,5-diones of formula IIIa or III may be reduced to yield a mixture of compounds of formula Va and Vb by the reduction in anhydrous alcohol with a metal reducing agent. Preferred metals include sodium, calcium and magnesium, with magnesium as a more preferred metal reducing agent. The reaction is typically carried out under an inert atmosphere of nitrogen for 30 minutes to 2 hours by refluxing a compound of formula III or formula IIIa in an alcohol selected from the group consisting of methanol, ethanol, n-propanol, and isopropanol with magnesium turnings. In preferred embodiments the reaction is conducted for about 40 minutes in methanol as described in Example 2, Procedure C, for the preparation of (±)-trans-3-(5,6-dihydro-4H-pyrrolo[3,2,1-ij]quinolin-1-yl)-4-(1H-indol-3-yl) pyrrolidine-2,5-dione.

Compounds of IVa and/or IVb, which have the pyrrolidine ring substituents in the cis configuration, may be converted into a mixture of compounds of Va and Vb, where the substituents are in the trans configuration, or into a mixture of all four isomers of formula IVa, IVb, Va, and Vb by treatment with base in a polar protic solvent. Typically the reaction employs an alkaline metal salt of a (C1-C4) alkyl alcohol in an alcohol solvent (e.g., sodium or potassium methoxide in methanol, sodium or potassium ethoxide in ethanol, sodium or potassium tert-butoxide in tert-butanol), with potassium tert-butoxide in tert-butanol as the preferred alkaline metal salt and solvent mixture. Reactions are generally conducted from 0° C. to the reflux temperature of the reaction mixture for 4 to 48 hours. In more preferred embodiments, the reaction are conducted from room temperature (25° C.) to the reflux temperature of the mixture for 8 to 24 hours, and in an even more preferred embodiment, the reaction is conducted at about 50° C. in a mixture of potassium tert-butoxide in tert-butanol for about 16 hours. Short reaction times and low temperatures favor formation of mixtures still containing compounds IVa and/or IVb.

3.1.3. Introduction of Aryl or Heteroaryl Substituents into Compounds of III, IIIa, IVa, IVb, Va, and Vb The introduction of additional substituted and unsubstituted aryl or heteroaryl substituents on to aromatic rings of compounds of formula III, IIIa, IVa, IVb, Va, or Vb may be accomplished by the reaction of a substituted or unsubstituted aryl or heteroaryl boronic acid with an aromatic halogen substituent on a compound of formula III, IIIa, IVa, IVb, Va, or Vb. The reaction is typically carried out by heating a mixture of a compound of formula III, IIIa, IVa, IVb, Va, or Vb bearing an aryl or heteroaryl bromide or iodide, more preferably an arylbromide or hetroarylbromide, with an aryl or heteroaryl boronic acid in the presence of tetrakistriphenylphosphine palladium in a solvent mixture consisting of 5 parts toluene, 5 parts ethanol, 1 part saturated NaHCO$_3$, and 2 parts water to 100° C. under nitrogen for 5 hours. After cooling to room temperature, the mixture is extracted with ethyl acetate and concentrated. The residue is purified by silica gel chromatography. In a preferred embodiment, the halogenated compound of formula III, IIIa, IVa, IVb, Va, or Vb bears the halogen on an aryl or heteroaryl group Q functionality resulting in the introduction of substituted aryl or heteroaryl group donated by the boronic acid on to the Q substituent. In a more preferred embodiment, the Q functionality is a brominated aromatic or heteroaromatic Q functionality. In another more preferred embodiment the halogenated Q functionality reacted with the boronic acid is a halogenated 3-indolyl. Examples 31-34 describe the introduction of substituted and unsubstituted aromatic groups into compounds of formula Va and Vb employing a brominated Q functionality where Q is a brominated 3-indolyl.

Aromatic and heteroaromatic boronic acids including 2-thienylboronic acid, 3-thienylboronic acid, and 2-naphthylboronic acid are available from a variety of commercial sources including Sigma-Aldrich (St. Louis, Mo.). Alternatively aromatic and heteroaromatic boronic acids may be prepared from the corresponding aryl or heteroaryl bromides by reaction with triisopropyl borate in the presence of n-butyllithium followed by quenching with aqueous HCl. (See, e.g., W. Li, et. al., *J. Organic Chem.* 67: 5394-97 (2002) and C. M. Marson, et. al., *Tetrahedron* 59: 4377-81 (2003).

3.1.4. Preparation of Compounds of Formula III, IIIa, IVa, IVb, Va, and Vb where R4 is —CH$_2$R7

Compounds of formula III, IIIa, IVa, IVb, Va, or Vb, where R4 is hydrogen, can be converted into compounds of formula III, IIIa, IVa, IVb, Va, or Vb where R4 is —CH$_2$R7. The conversion begins with the preparation of the hydroxymethylene derivative of the compounds as indicated in the partial structures shown in Scheme 2.

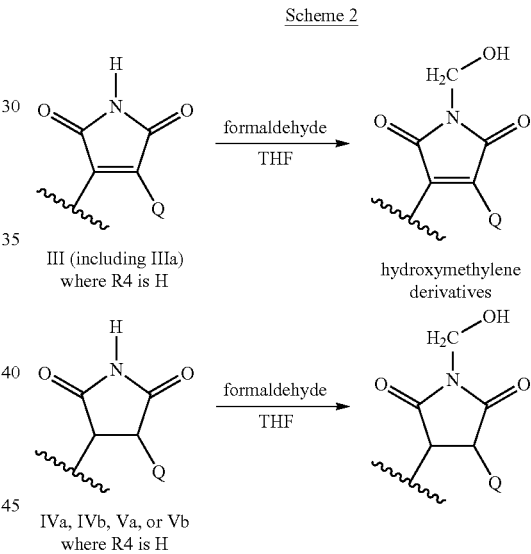

Scheme 2

III (including IIIa) where R4 is H hydroxymethylene derivatives

IVa, IVb, Va, or Vb where R4 is H

Preparation of the hydroxymethylene derivatives is accomplished by reaction of a compound of formula III, IIIa, IVa, IVb, Va, or Vb where R4 is H with aqueous formaldehyde in tetrahydrofuran (THF). Typical reaction conditions employ equal volumes of THF and 37% formaldehyde in water with the reaction stirred for 14-16 hours at room temperature. Reaction times and temperatures may vary from 1 hour to 48 hours and the temperature may be from 0° C. to 50° C. or more preferably from 10° C. to 37° C. Upon completion the reaction is partitioned between water and an organic solvent, typically ethyl acetate. The organic layer is dried over sodium sulfate, concentrated, and subject to chromatography on silica gel as necessary to yield the hydroxymethylene product. The preparation of the hydroxymethylene derivative of 3-(5,6-dihydro-4H-pyrrolo[3,2,1-ij]quinolin-1-yl)-4-(1H-indol-3-yl) pyrrolidine-2,5-dione, 3-(5,6-dihydro-4H-pyrrolo[3,2,1-ij]quinolin-1-yl)-1-hydroxymethyl-4-(1H-indol-3-yl)-pyrrolidine-2,5-dione, is described in Example 56, step 1.

Compounds of formula III, IIIa, IVa, IVb, Va, or Vb where R4 is —CH$_2$R7 and R7 is phosphate (—O—P(=O)(OH)$_2$), monoalkyl phosphate (e.g., —O—P(=O)(—OH)(—O—(C$_1$-C$_6$) alkyl)), dialkyl phosphate (e.g., —O—P(=O)(—O—(C$_1$-C$_6$) alkyl)$_2$) a monobenzylphosphate ester (—O—P(=O)(—OH) (—O—(CH$_2$)-phenyl)), or a dibenzylphosphate ester (—O—P(=O)(—O—(CH$_2$)-phenyl)$_2$) may be prepared from the desired hydroxymethylene derivative and a suitably substituted phosphoric acid by any reaction suitable for the formation of a phosphate ester bond between the phosphoric acid compound and the hydroxymethylene derivative. In a preferred method, the formation of phosphate esters is conducted by reaction of a hydroxymethylene derivative of a compound of formula III, IIIa, IVa, IVb, Va, or Vb with a suitably protected phosphoramidate followed by deprotection. Reactions with the desired phosphoramidate are typically conducted at room temperature in anhydrous THF. Following the addition of the phosphoramidate, the reaction is treated with tetrazole (3% in acetonitrile) and stirred 5 minutes to 1 hour, after which the reaction is cooled to −78° C. The cooled reaction is treated with m-chloroperbenzoic acid, and after stirring at −78° C. for 5 minutes, the reaction is warmed to room temperature and stirred for 5 minutes further. Following the removal of solvent, the product is purified by flash chromatography on silica gel using ethyl acetate hexane. The protecting groups are removed by suitable deprotection reactions. Where the phosphoramidate employed is dibenzylphosphoramidate, the benzyl protecting groups may be removed by hydrogenation of the compound over Pd/C under 1 atmosphere of hydrogen at room temperature. The preparation of phosphoric acid mono-[3-(5,6-dihydro-4H-pyrrolo[3,2,1-ij]quinolin-1-yl)-4-(1H-indol-3-yl)-2,5-dioxo-pyrrolidin-1-ylmethyl]ester from 3-(5,6-dihydro-4H-pyrrolo[3,2,1-ij]quinolin-1-yl)-1-hydroxymethyl-4-(1H-indol-3-yl)-pyrrolidine-2,5-dione is described in Example 56, steps 2-3.

Compounds of formula III, IIIa, IVa, IVb, Va, or Vb where R7 is a carboxylic acid group, or an amino carboxylic acid group, may be prepared by coupling the desired hydroxymethylene derivative with a carboxylic acid or amino carboxylic acid (amino acid) under conditions suitable for the formation of an ester linkage. A variety of dehydrating agents, including DCC (dicyclohexylcarbodiimide), HBTU (O-(benzotriazol-1-yl)-N,N,N',N'-tetramethyluronium hexafluorophosphate), or BOP ((benzotriazol-1-yloxy)tris (dimethylamino)phosphonium hexafluorophosphate) may be employed to drive the formation of the ester bond. In a preferred embodiment, the reactions are conducted in anhydrous THF in the presence of HBTU and DIEPA (N,N-diisopropylethylamine) at room temperature for 10 hours to 24 hours. Following completion of the dehydration reaction, solvent is removed under reduced pressure and the compounds are taken up in an organic solvent (e.g., ethyl acetate) and washed with water. The organic layer is dried and the residue purified by silica gel chromatography as necessary.

Where R7 is an amino carboxylic acid group, the starting materials for introducing the amino carboxylic acid group must contain a suitably protected amine. A variety of suitable amine-protecting groups may be advantageously employed including carbobenzyloxy-protected amines (e.g., the reactions may employ N-carbobenzyloxy glycine or N-carbobenzyloxy alanine etc.). Subsequent deprotection will yield the free product. Where the protecting group employed is carbobenzyloxy, deprotection may be accomplished by treating the amine protected product suspended in methanol with HCl (4M) in ethyl acetate in the presence of palladium on charcoal (Pd/C) under 1 atmosphere of hydrogen for 1-3 hours at room temperature. Examples 58-60 describe the preparation of compounds where R7 is a carboxylic acid group, or an amino carboxylic acid group.

Compounds of formula III, IIIa, IVa, IVb, Va, or Vb where R7 is a peptide, may be prepared by coupling the desired hydroxymethylene derivative with a peptide bearing a free carboxylic acid group to form an ester linkage. Linking of a carboxyl functionality of a peptide and the hydroxymethylene group in an ester linkage may be conducted employing a suitably protected peptide, bearing for example, protected free amine groups protected with conventional N-protecting groups. Conditions suitable for the formation of an ester linkage, include those employing dehydrating agents, such as those described for the preparation of compounds of formula III, IIIa, IVa, IVb, Va, or Vb where R4 is —CH$_2$R7 and R7 is a carboxylic acid group, or an amino carboxylic acid group.

3.1.5. Preparation of Compounds of Formula III, IIIa, IVa, IVb, Va, and Vb where R4 is —(C$_1$-C$_6$) alkyl Compounds of formula III, IIIa, IVa, IVb, Va, or Vb where R4 is a —(C$_1$-C$_6$) alkyl may be prepared by reacting by reacting the desired compound of formula III, IIIa, IVa, IVb, Va, or Vb where R4 is H with a (C$_1$-C$_6$) alkyl halide, where the halide is preferably Cl, Br or I, in the presence of a suitable base at room temperature. Suitable bases include organic bases such as potassium tert-butoxide, sodium methoxide, and inorganic bases such as KOH, NaOH and K$_2$CO$_3$. Suitable solvents include polar aprotic solvents such as DMSO, THF, dioxane or other ethers, or DMF. In an alternative embodiment, the compound of formula III, IIIa, IVa, IVb, Va, or Vb where R4 is H is reacted with an organic or inorganic base to yield the conjugate base of the compound of formula III, IIIa, IVa, IVb, Va, or Vb, and the conjugate base is then reacted with the alkylhalide. Where the alkyl group is introduced into a compound of formula III or IIIa, the resulting alkylated compounds can be reduced to yield compounds of formula IVa and IVb, Va and Vb, or a mixture of compounds of formula IVa, IVb, Va, and Vb employing the reduction procedures described in Section I(b)(1). Example 61 describes the preparation of 3-(5,6-dihydro-4H-pyrrolo[3,2,1-ij]quinolin-1-yl)-4-(1-methylindol-3-yl)-1-methyl pyrrole-2,5-dione using iodomethane as an alkylating agent, and its reduction by catalytic hydrogenation to yield (±)-cis-3-(5,6-dihydro-4H-pyrrolo[3,2,1-ij] quinolin-1-yl)-4-(1-methylindol-3-yl)-1-methyl pyrrolidine-2,5-dione.

Compounds of formula III, IIIa, IVa, IVb, Va, or Vb where R4 is a —(C$_1$-C$_6$) alkyl group may also be prepared by reacting the desired compound of formula III, IIIa, IVa, IVb, Va, or Vb where R4 is H with a (C$_1$-C$_6$) alkyl alcohol in the presence of diethylzodicarboxylate (DEAD) and triphenylphosphine. (See, e.g., Mitsunobu, O.; Wade, M.; Sano, T. *J. Am Chem. Soc.* 94: 694 (1972); Hughes, D. L., *Organic Reactions*, 42; 335-656 (1992)). The reactions may be conducted in a variety of solvents including tetrahydrofuran (THF), dichloromethane, chloroform, acetonitrile, and benzene, preferably the solvent is THF.

3.1.6. Separation of Compounds of Formula III, IIIa, IVa, IVb, Va, and Vb

Where the isolation of an individual product having the structure of formula III, IIIa, IVa, IVb, Va, or Vb is desired, the products may be separated by chromatography on one or more chromatography media. Chromatography may be carried out on a preparative scale or on an analytical scale to determine the identity and purity of the products present in a sample. Although any suitable chromatography media including, but not limited to, silica, reverse phase, ion exchange, chiral chromatographic media, or any combination thereof, may be advantageously employed for separations, the suitability of specific chromatographic media and conditions for the separation of products having formula III, IIIa, IVa, IVb, Va, and Vb will depend upon the substituents present on the compounds. In preferred embodiments, chromatographic separations are conducted employing HPLC. In other preferred embodiments the separation is carried out using supercritical fluid chromatography. Where supercritical fluid chromatography is employed, $CO_2$, or mixtures of $CO_2$ with other solvents including acetonitrile (ACN), methanol, ethanol, isopropanol, or hexane, are the preferred mobile phase, with mixtures of $CO_2$ and methanol most preferred. A variety of chromatographic media (stationary phases) may be employed in supercritical fluid chromatography including, but not limited to: ChiralCel OA, OB, OD, or OJ; ChiralPak AD or AS; Cyclobond I, II, or III; and Chirobiotic T, V, and R media.

In more preferred embodiments, where the products are individual isomers of formula IVa, IVb, Va, or Vb, mixtures containing two or more of the isomeric forms may be separated by using supercritical fluid chromatography on chiral media. In one more preferred embodiment, separations are conducted on CHIRALPAK® AD columns (Daicel (U.S.A.) Inc. Fort Lee, N.J.). In that embodiment, products are applied to the AD column in a mixture of methanol and acetonitrile, or in acetonitrile, and the column is subsequently eluted with 35% methanol in CO2 (65%). The separation of 3(R),4(S)-3-(5,6-dihydro-4H-pyrrolo[3,2,1-ij]quinolin-1-yl)-4-(1H-indol-3-yl) pyrrolidine-2,5-dione and 3(S),4(R)-3-(5,6-dihydro-4H-pyrrolo[3,2,1-ij]quinolin-1-yl)-4-(1H-indol-3-yl) pyrrolidine-2,5-dione on a CHIRALPAK® AD column is set forth in Example 4. The separation of (+) trans-3-(5,6-dihydro-4H-pyrrolo[3,2,1-ij]quinolin-1-yl)-4-(1H-indol-3-yl) pyrrolidine-2,5-dione and (−) trans-3-(5,6-dihydro-4H-pyrrolo[3,2,1-ij]quinolin-1-yl)-4-(1H-indol-3-yl) pyrrolidine-2,5-dione is set forth in Example 5.

The individual racemic forms of compounds of formula III, IIIa, IVa, IVb, Va, or Va may also be resolved by physical methods, such as, for example, fractional crystallization or crystallization of diastereomeric derivatives. In addition, individual optical isomers can be obtained from racemic mixtures by conventional methods, such as, for example, salt formation with an optically active acid, where applicable, followed by crystallization.

3.2. Preparation of Compounds of Formula I and II where Y is a Bond

Compounds of formula I and II, which are employed in the synthesis of pyrroloquinolinyl-pyrrole-2,5-dione of formula III and IIIa, may be purchased or obtained via a variety of synthetic routes such as those set forth below.

3.2.1. Preparation of Compounds of Formula I where Y is a Bond

Compounds of formula I may be prepared from the corresponding compound of formula A, where X is selected from the group consisting of —($CH_2$)—, —($NR8$)-, S and O,
R8 is selected from the group consisting of hydrogen, —($C_1$-$C_6$) alkyl, —($C_1$-$C_6$) substituted alkyl, —($C_3$-$C_9$) cycloalkyl, —($C_3$-$C_9$) substituted cycloalkyl, and —O—($C_1$-$C_6$) alkyl, and m is 1 or 2. Exemplary compounds of formula A include 1,2,3,4-tetra hydroquinoline, 1,2,3,4-tetrahydro-quinoxaline, 3,4-dihydro-2H-benzo[1,4]oxazine, 3,4-dihydro-2H-benzo[1,4]thiazine, 2,3,4,5-tetrahydro-1H-benzo[b]azepine, 2,3,4,5-tetrahydro-1H-benzo[b][1,4]diazepine, 6,7,8,9-tetrahydro-5-oxa-9-aza-benzocycloheptene, or 2,3,4,5-tetrahydro-benzo[b][1,4]thiazepine. The preparation begins with the conversion of a compound of formula A to the corresponding 3-substituted-2-oxopropionic acid ethyl ester of formula B. The ethyl ester of formula B is cyclized to form a compound of formula C, which is converted to the free acid D, which is decarboxylated to yield the desired tricyclic product E. Subsequent reaction of the tricyclic product E with oxalyl chloride and work-up in alcoholic base yields the corresponding compound of formula I. Scheme 3 illustrates the reaction sequence beginning with compounds of formula A, which is further illustrated in Example 1, steps 1-5 for the preparation of 5,6-dihydro-4H-pyrrolo[3,2,1-ij]quinolin-1-yl) oxoacetic methyl ester of formula I from 1,2,3,4-tetrahydroquinoline and bromoethylpyruvate (3-bromo-pyruvic acid ethyl ester).

Some suitable conditions for the conversion of compounds of formula A into compounds of formula I through the reaction sequence of Scheme 3 are described herein. Compounds of formula A may be converted to the corresponding 3-substituted-2-oxopropionic acid ethyl ester of formula B by treatment with bromoethyl pyruvate in an anhydrous ether, such as THF, at room temperature for about 24 hours. Treatment of the 3-substituted-2-oxopropionic acid ethyl ester of formula B with anhydrous $MgCl_2$ in 2-methoxyethanol at about 125° C. for 30 minutes to 2 hours, preferably for 1 hour, results in the formation of the corresponding tricyclic carboxylic acid ester of formula C. Subsequent conversion of this compound to the free acid of formula D may be accomplished by hydrolysis in aqueous base. In preferred embodiments the reaction is carried out in an aqueous base, including but not limited to NaOH or KOH, in the presence of alcohol as a co-solvent. Preferred alcohol co-solvents include methanol, ethanol, n-propanol, and isopropanol, with ethanol as a more preferred co-solvent. Reactions are typically conducted by heating the mixture to reflux for 2 hours, although the time and temperature of the reaction may be varied as needed. Oxidative decarboxylation of compounds of formula D may be conducted by a variety of procedures suitable for the decarboxylation of aromatic acids. In preferred embodiments the decarboxylation of compounds of formula D is conducted by heating the free acid with copper-chromite ($CuO$—$Cr_2O_3$) in quinolone for about 2 hours to yield the decarboxylated product of formula E. Conversion of compounds of formula E to compounds of formula I may be accomplished by reaction with oxalyl chloride, followed by treatment with a mixture of an anhydrous alcohol and the alkaline metal salt of the alcohol, preferably sodium methoxide, or sodium ethoxide. The reaction of oxalyl chloride with compounds of formula E is typically conducted in anhydrous polar aprotic solvents including ethers at a temperature from about −78° C. to about 10° C. In preferred embodiments, the reaction is conducted at a temperature from about −25° C. to about 5° C. employing an ether as a solvent. In more preferred embodiments the reaction is conducted at 0° C. Preferred solvents for conducting the reaction include, but are not limited to tetrahydrofuran (THF), tetrahydropyran, diethyl ether and the like.

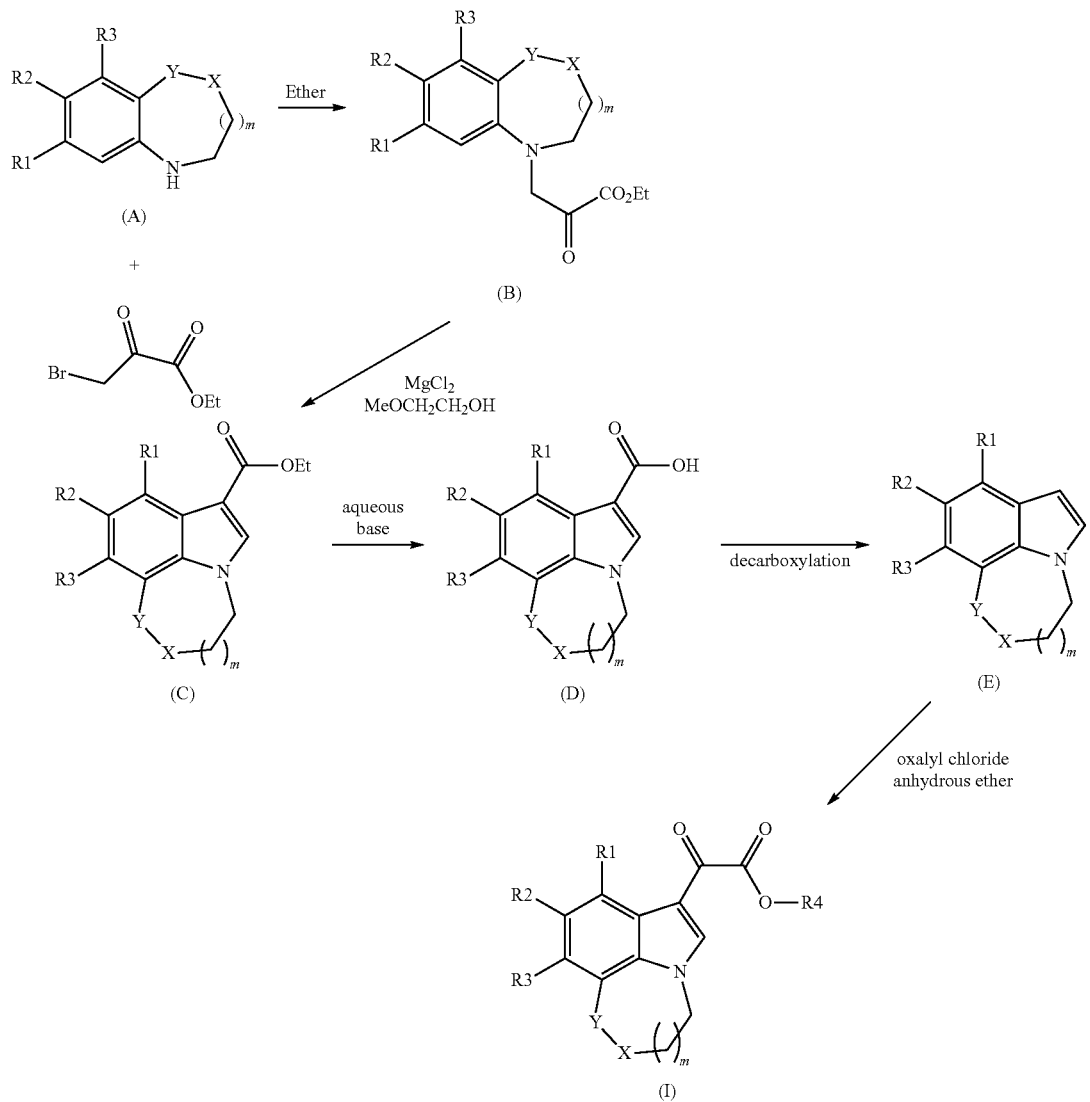

Scheme 3. Preparation of Compounds of Formula (I) where Y is a bond

3.2.2. Preparation of Compounds of Formula II

Compounds of formula II, which are substituted acetamides, may be purchased or prepared from commercially available starting materials. Commercially available acetamides including: indole-3-acetamide, 2-(5-methyl-1H-indol-3-yl)acetamide, 2-(5-methoxy-1H-indol-3-yl)acetamide, 2-(4-hydroxy-1H-indol-3-yl)acetamide, 2-phenylacetamide, 2-(4-methylphenyl)acetamide, 4-hydroxyphenylacetamide, 4-hydroxyphenylacetamide, N-cyclopentyl-2-(4-hydroxy-2-oxo-1,2-dihydro-3-quinolinyl)acetamide, 2-phenoxyacetamide, 2-(2-methylphenoxyl)acetamide, 2-(4-fluorophenoxyl)acetamide, 2-(4-pyridinyl) acetamide, and 2-[(4-chlorophenyl)sulfanyl]acetamide are available from a variety of sources including Sigma Aldrich Chemical Co., St. Louis Mo. A compound of formula II may also be prepared from its corresponding free acid by conversion of the free acid to its acid chloride followed by reaction with ammonia.

3.3. Additional Routes for the Preparation of Pyrroloquinolinyl-pyrrolidine-2,5-diones In addition to those routes for the preparation of pyrroloquinolinyl-pyrrolidine-2,5-diones described above, additional routes of preparing the compounds exemplified for (±)-trans-3-(5,6-dihydro-4H-pyrrolo[3,2,1-ij]quinolin-1-yl)-4-(1H-indol-3-yl) pyrrolidine-2,5-dione are described in Examples 62-64.

4. The Pharmaceutical Compositions and Formulations

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount," as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one aspect, the active compounds are prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 3000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

Preferably, (−)-trans-3-(5,6-dihydro-4H-pyrrolo[3,2,1-ij] quinolin-1-yl)-4-(1H-indol-3-yl) pyrrolidine-2,5-dione is administered at dosage of 360 mg, twice a day, for a maximal daily dosage of 720 mg. (−)-trans-3-(5,6-dihydro-4H-pyrrolo[3,2,1-ij]quinolin-1-yl)-4-(1H-indol-3-yl) pyrrolidine-2,5-dione is optionally administered to subjects or patients at an initial dosage of 10 mg twice daily for a maximal daily dose of 20 mg, with dosage escalation to administration of 360 mg twice daily for a maximal daily dosage of 720 mg. Preferred dosage forms of (−)-trans-3-(5,6-dihydro-4H-pyrrolo[3,2,1-ij]quinolin-1-yl)-4-(1H-indol-3-yl) pyrrolidine-2,5-dione include, but are not limited to, caplets, tablets, pills, and freeze-dried powder. For instance, a subject or patient is administered one 360 mg caplet twice a day, or alternatively, two 180 mg caplets, twice a day, for a maximal daily dosage of 720 mg. (−)-trans-3-(5,6-dihydro-4H-pyrrolo[3,2,1-ij]quinolin-1-yl)-4-(1H-indol-3-yl) pyrrolidine-2,5-dione caplets or tablets are also formulated in 60 mg doses.

The pharmaceutical compositions can include co-formulations of any of the compounds described herein.

The pharmaceutical compositions can be included in a container, pack, or dispenser together with instructions for administration.

EXAMPLES

Examples are provided below to further illustrate different features of the present invention. The examples also illustrate useful methodology for practicing the invention. These examples do not limit the claimed invention.

Example 1

Preparation of 3-(5,6-Dihydro-4H-pyrrolo[3,2,1-ij] quinolin-1-yl)-4-(1H-indol-3-yl) pyrrole-2,5-dione Step 1

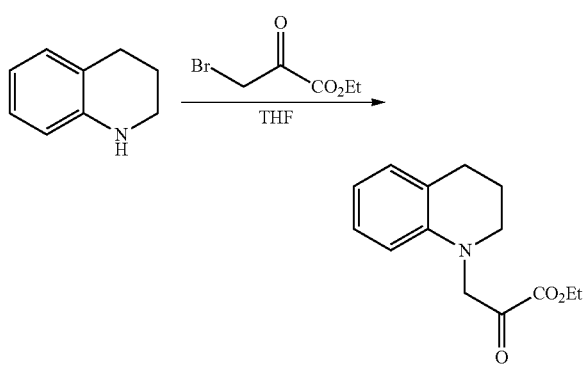

To a solution of 1,2,3,4-tetrahydroquinoline (100 mL) in anhydrous tetrahydrofuran (300 mL), bromoethylpyruvate (53 mL) was added dropwise over 30 minutes. The mixture was stirred for 24 hours at room temperature. The reaction mixture was filtered and the solid washed with tetrahydrofuran (100 mL). The filtrate was evaporated to dryness to give 3-(3,4-dihydro-2H-quinolin-1-yl)-2-oxopropionic acid ethyl ester as a brown oil 117 g.
Step 2

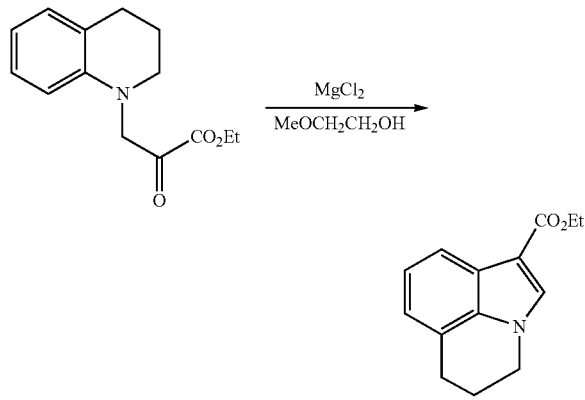

Anhydrous magnesium chloride (29.4 g, 0.31 mol) was suspended in 2-methoxyethanol (400 ml), and the mixture was stirred for 15 minutes at 125° C. A solution of 3-(3,4-dihydro-2H-quinolin-1-yl)-2-oxopropionic acid ethyl ester (76.57 g 0.31 mol) in 2-methoxyethanol (100 ml) was then added and the mixture stirred at 125° C. for 60 minutes. The mixture was stirred for a further 5 hours at reflux, cooled and evaporated to dryness. The residue was then acidified with 2 M hydrochloric acid (500 mL) and extracted with dichloromethane (3×500 mL). The combined organic layers were then washed with 5% sodium bicarbonate solution and dried over anhydrous magnesium sulfate before being evaporated to dryness. The residue was then purified on a silica gel chromatography column, eluting with ethyl acetate/hexanes (1:4) to provide 5,6-dihydro-4H-pyrrolo [3,2,1-ij]quinoline-1-carboxylic acid ethyl ester (31.0 g, 47%). $^1$H NMR (CDCl$_3$) 400 MHz δ: 7.9 (d, 1H, J=8 Hz), 7.79 (s, 1H), 7.17 (m, 1H), 6.99 (d, 1H, J=7.2 Hz), 4.37 (m, 2H), 4.18 (t, 2H, J=5.6 Hz), 3.0 (t, 2H, J=6 Hz), 2.24 (t, 2H, J=6 Hz), 1.42 (t, 3H, J=7.2 Hz).

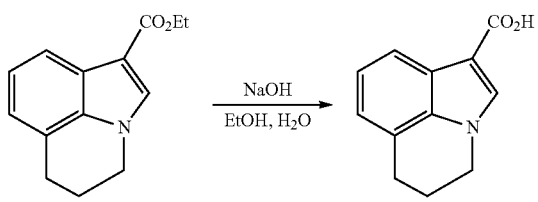

To a solution of 5,6-dihydro-4H-pyrrolo[3,2,1-ij]quinoline-1-carboxylic acid ethyl ester (31 g, 0.14 mol) in ethanol (200 mL) and water (200 mL) was added sodium hydroxide (30.8 g, 0.77 mol). The mixture was heated to reflux for 2 hours before being cooled to room temperature and diluted with water (2.64 L). The mixture was then washed with dichloromethane (2×300 mL) and the aqueous layer was acidified with concentrated hydrochloric acid to pH 1.0. The precipitate formed was collected by filtration, washed with water and dried to yield 5,6-dihydro-4H-pyrrolo[3,2,1-ij]quinoline-1-carboxylic acid as a dark yellow solid (23 g, 85%). $^1$H NMR (DMSO-d$_6$) 400 MHz δ: 11.95 (brs, 1H), 7.96 (s, 1H), 7.69 (d, 1H, J=8.4 Hz), 7.06 (t, 1H, J=6.8 Hz), 6.92 (d, 1H, J=6.8 Hz), 4.19 (t, 2H, J=6 Hz), 2.91 (t, 2H, J=6 Hz), 2.11 (t, 2H, J=5.6 Hz).
Step 4

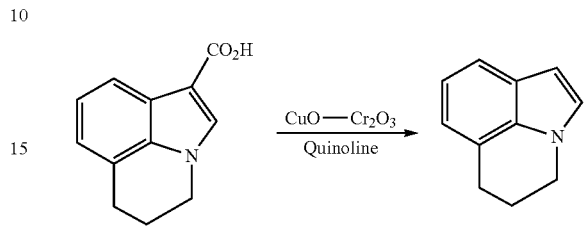

5,6-dihydro-4H-pyrrolo[3,2,1-ij]quinoline-1-carboxylic acid (37.5 g, 0.186 mol), copper chromite (13.5 g, 43 mmol) and quinoline (180 mL) were heated with stirring to 185° C. for 2 hours. The mixture was cooled, diluted with dichloromethane (1 L) and filtered over hyflo. The filtrate was washed with 2 M hydrochloric acid (2×600 mL) and twice with 2 M sodium hydroxide (150 mL) before being evaporated to dryness. The residue was purified by silica gel chromatography, eluting with a ethyl acetate/hexanes (1:6) to afford 5,6-dihydro-4H-pyrrolo[3,2,1-ij]quinoline (21 g, 72%) as a pale yellow solid. $^1$H NMR (CDCl$_3$) 400 MHz δ: 7.44 (dd, 1H, J=0.8 and 7.6 Hz), 7.07 (d, 1H, J=3.2 Hz), 7.01 (t, 1H, J=7.2 Hz), 6.9 (dd, 1H, J=0.8 and 6.8 Hz), 6.43 (d, 1H, J=3.2 Hz), 4.16 (t, 2H, J=6 Hz), 2.99 (t, 2H, J=6.4 Hz), 2.24 (m, 2H).
Step 5

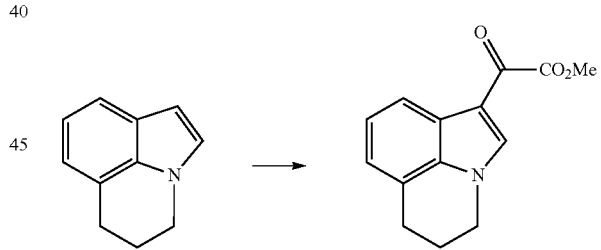

To a solution of 5,6-dihydro-4H-pyrroloquinoline (4.0 g, 25.3 mmol), in anhydrous ether (300 mL) at 0° C., was added oxalyl chloride (2.22 mL, 25.3 mmol). The mixture was stirred for 30-45 minutes at 0° C. before being cooled to −78° C. Sodium methoxide in methanol (0.5M) (60 mL) was then added slowly and the mixture allowed to warm to room temperature. The mixture was then diluted with ethyl acetate (200 mL), washed with water (100 mL) followed by a wash with saturated aqueous sodium chloride (50 mL). The organic layer was dried over anhydrous sodium sulfate and evaporated to dryness. The residue was dissolved in ethyl acetate (100 mL) filtered through a 2 inch plug of coarse silica gel and evaporated to give 5,6-dihydro-4H-pyrrolo[3,2,1-ij]quinolin-1-yl) oxoacetic acid methyl ester as a yellow solid (5.3 g, 85%). $^1$H NMR (CDCl$_3$) 400 MHz δ: 8.3 (s, 1H), 8.14 (d, 1H), 7.22 (t, 1H), 7.04 (d, 1H), 4.2 (t, 2H), 3.95 (s, 3H), 3.0 (t, 2H), 2.3 (t, 2H).

Step 6

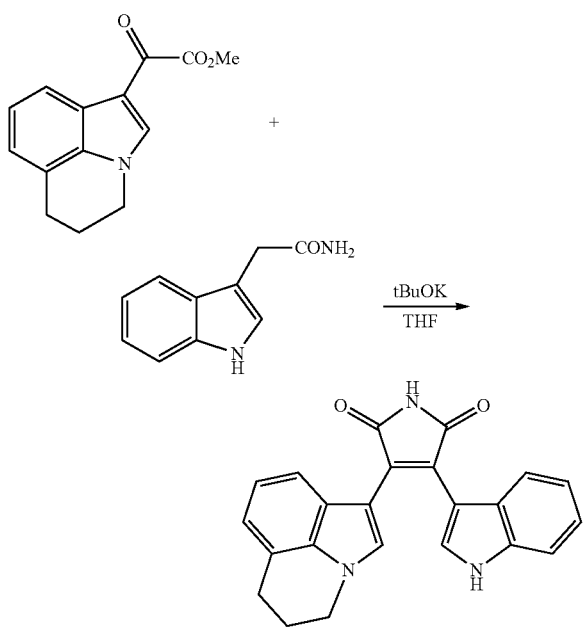

To a solution of 5,6-dihydro-4H-pyrrolo[3,2,1-ij]quinolin-1-yl) oxoacetic acid methyl ester (1.0 g, 4.12 mmol) and indole-3-acetamide (0.8 g, 4.5 mmol) in anhydrous tetrahydrofuran at 0° C. was added a solution of potassium t-butoxide (1M in tetrahydrofuran) (12.4 mL, 12.4 mmol) dropwise over 30 minutes. The mixture was stirred at 0° C. for 2 hours. Concentrated hydrochloric acid (10 mL) was then added and the mixture stirred for 1 hour at room temperature. The mixture was then diluted with ethyl acetate (200 mL), washed twice with water (50 mL), and saturated aqueous sodium chloride solution (50 mL) and the organic layer dried over anhydrous sodium sulfate. The residue was purified by silica gel chromatography, eluting with ethyl acetate/hexanes (1:4) to afford 3-(5,6-dihydro-4H-pyrrolo[3,2,1-ij]quinolin-1-yl)-4-(1H-indol-3-yl) pyrrole-2,5-dione as a bright red solid (1.2 g, 80%). $^1$H NMR (CDCl$_3$) 400 MHz δ: 8.5 (brs, 1H), 7.78 (s, 1H), 7.63 (d, 1H, J=2.8 Hz), 7.44 (s, 1H), 7.35 (d, 1H, J=8 Hz), 7.16 (d, 1H, J=8.4 Hz), 7.11 (t, 1H, J=7.6 Hz), 6.86 (t, 1H, J=7.6 Hz), 6.80 (d, 1H, J=7.2 Hz), 6.64 (t, 1H, J=8 Hz), 6.57 (d, 1H, J=8 Hz), 4.2 (t, 2H, J=6 Hz), 2.96 (t, 2H, J=6 Hz), 2.24 (m, 2H).

Example 2

Preparation of (±)-Cis-3-(5,6-dihydro-4H-pyrrolo[3,2,1-ij]quinolin-1-yl)-4-(1H-indol-3-yl) pyrrolidine-2,5-dione and (±)-Trans-3-(5,6-dihydro-4H-pyrrolo[3,2,1-ij]quinolin-1-yl)-4-(1H-indol-3-yl) pyrrolidine-2,5-dione Preparation of the (±)-cis compounds, (±)-trans compounds, or mixtures thereof were obtained using reducing conditions as described in each of Procedures A through C.

Procedure A:

Reduction of 3-(5,6-dihydro-4H-pyrrolo[3,2,1-ij]quinolin-1-yl)-4-(1H-indol-3-yl) pyrrole-2,5-dione with Zn/Hg.

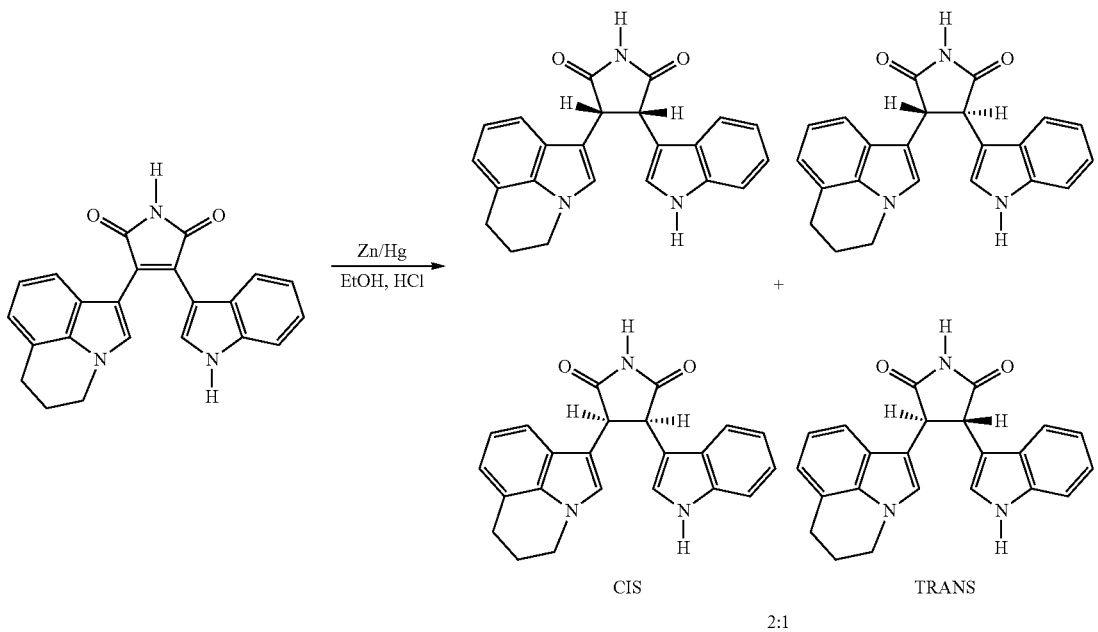

The active zinc-mercury reducing agent for the reduction of 3-(5,6-dihydro-4H-pyrrolo[3,2,1-ij]quinolin-1-yl)-4-(1H-indol-3-yl) pyrrole-2,5-dione was prepared from metallic zinc and HgCl$_2$. Zinc powder (2.5 g) and mercury (II) chloride (0.25 g) were suspended in deionized water (3 mL) and stirred for 20 minutes. A few drops of concentrated hydrochloric acid was then added and the mixture stirred for few minutes. The solid was filtered off, washed with deionized water (50 mL), ethanol (50 mL) and dried.

To a suspension of the Zn(Hg) reducing agent prepared as above in dry ethanol (50 mL) was added 3-(5,6-dihydro-4H-pyrrolo[3,2,1-ij]quinolin-1-yl)-4-(1H-indol-3-yl) pyrrole-2,5-dione (0.35 g, 95.4 μmol.). The mixture was heated to reflux for 30-60 minutes while dry hydrogen chloride gas was slowly passed through the mixture. The mixture was then cooled, filtered, and evaporated to dryness. A 5% potassium carbonate solution (150 mL) and ethyl acetate (300 mL) were then added. The organic layer was dried over anhydrous magnesium sulfate and evaporated to give ~2:1 mixture of (±)-cis-3-(5,6-dihydro-4H-pyrrolo[3,2,1-ij]quinolin-1-yl)-4-(1H-indol-3-yl) pyrrolidine-2,5-dione and (±)-trans-3-(5,6-dihydro-4H-pyrrolo[3,2,1-ij]quinolin-1-yl)-4-(1H-indol-3-yl) pyrrolidine-2,5-dione (0.2 g).

Procedure B:
Reduction of 3-(5,6-dihydro-4H-pyrrolo[3,2,1-ij]quinolin-1-yl)-4-(1H-indol-3-yl) pyrrole-2,5-dione with hydrogen in the presence of palladium on carbon.

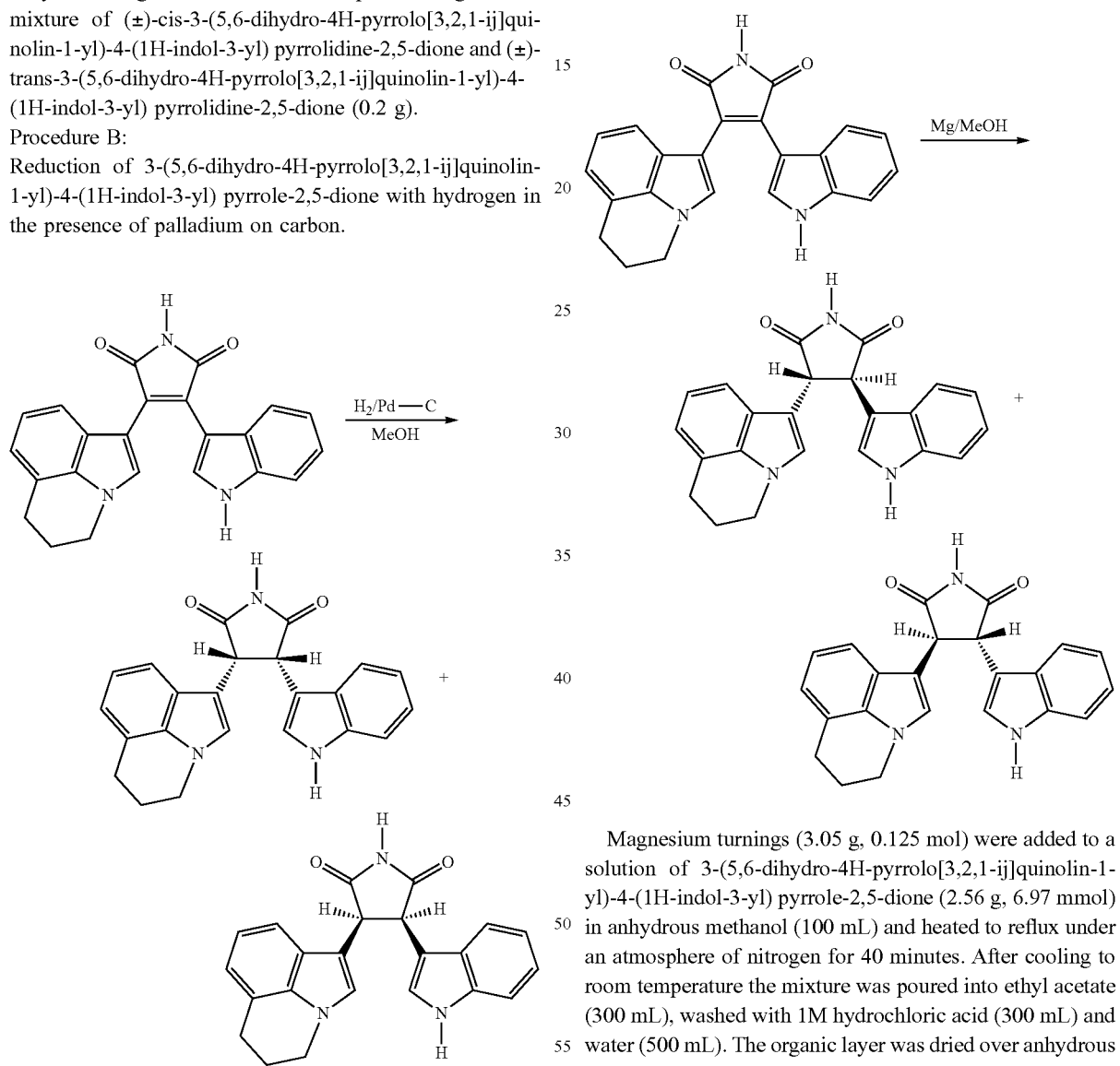

A suspension of 3-(5,6-dihydro-4H-pyrrolo[3,2,1-ij]quinolin-1-yl)-4-(1H-indol-3-yl) pyrrole-2,5-dione (16 g, 43.6 mmol) and 10% palladium on carbon (Pd/C, wet catalyst) (8 g) were stirred under 1 atmosphere of hydrogen in methanol (600 mL) at room temperature for 48 hours. The catalyst was then filtered through a bed of Celite and the filtrate evaporated to dryness. The residue was re-dissolved in methanol and the product precipitated by the addition of cold water. The precipitate was filtered, washed with water and dried under vacuum to yield (±)-cis-3-(5,6-dihydro-4H-pyrrolo[3, 2,1-ij]quinolin-1-yl)-4-(1H-indol-3-yl) pyrrolidine-2,5-dione (9.2 g). $^1$H NMR (DMSO-$d_6$) 400 MHz δ: 11.56 (s, 1H), 10.66 (s, 1H), 7.43 (d, 1H, J=7.6 Hz), 7.14 (d, 2H, J=8 Hz), 6.86-6.97 (m, 4H), 6.78 (t, 1H, J=7.2 Hz), 6.69 (d, 1H, J=6.8 Hz), 4.88 (dd, 2H, J=9.2 and 45.6 Hz), 3.88 (m, 2H), 2.76 (t, 2H, J=5.6 Hz), 1.94 (t, 2H, J=6 Hz).

Procedure C:
Reduction of 3-(5,6-dihydro-4H-pyrrolo[3,2,1-ij]quinolin-1-yl)-4-(1H-indol-3-yl) pyrrole-2,5-dione by magnesium in methanol.

Magnesium turnings (3.05 g, 0.125 mol) were added to a solution of 3-(5,6-dihydro-4H-pyrrolo[3,2,1-ij]quinolin-1-yl)-4-(1H-indol-3-yl) pyrrole-2,5-dione (2.56 g, 6.97 mmol) in anhydrous methanol (100 mL) and heated to reflux under an atmosphere of nitrogen for 40 minutes. After cooling to room temperature the mixture was poured into ethyl acetate (300 mL), washed with 1M hydrochloric acid (300 mL) and water (500 mL). The organic layer was dried over anhydrous sodium sulfate and evaporated to dryness. The residue was then purified by silica gel chromatography using 40-50% ethyl acetate in hexanes to yield (±)-trans-3-(5,6-dihydro-4H-pyrrolo[3,2,1-ij]quinolin-1-yl)-4-(1H-indol-3-yl) pyrrolidine-2,5-dione as a pale pink solid (2.3 g). $^1$H NMR (DMSO-$d_6$) 400 MHz δ: 11.54 (s, 1H), 11.03 (s, 1H), 7.32-7.4 (m, 4H), 7.17 (d, 1H, J=7.2 Hz), 7.07 (t, 1H, J=7.6 Hz), 6.96 (t, 1H, J=7.6 Hz), 6.82-6.89 (m, 2H), 4.5 (dd, 2H, J=7.2 and 20 Hz), 4.07 (t, 2H, J=5.2 Hz), 2.87 (t, 2H, J=6 Hz), 2.08 (m, 2H).

Example 3

Preparation of (±)-Trans-3-(5,6-dihydro-4H-pyrrolo[3,2,1-ij]quinolin-1-yl)-4-(1H-indol-3-yl) pyrrolidine-2,5-dione from (±)-Cis-3-(5,6-dihydro-4H-pyrrolo[3,2,1-ij]quinolin-1-yl)-4-(1H-indol-3-yl) pyrrolidine-2,5-dione

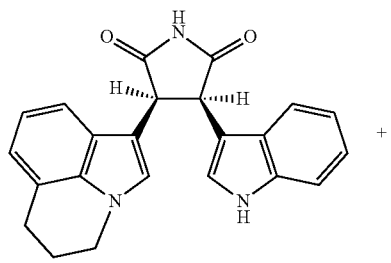

+

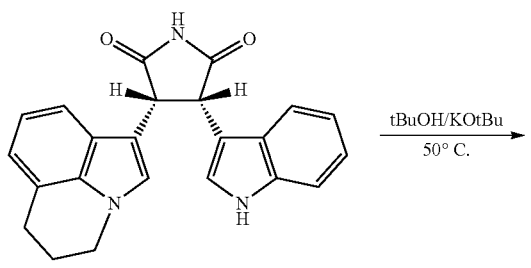 tBuOH/KOtBu 50° C.

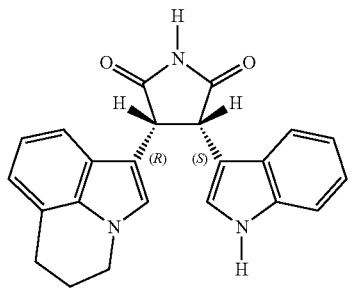

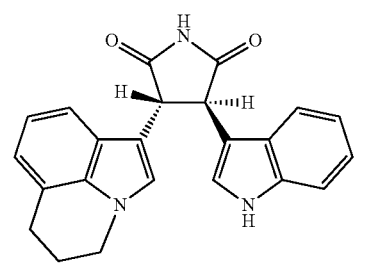 +

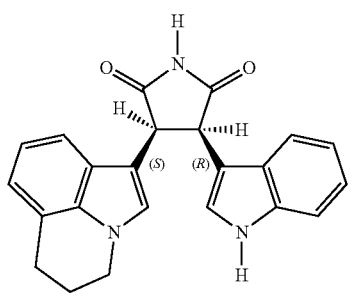

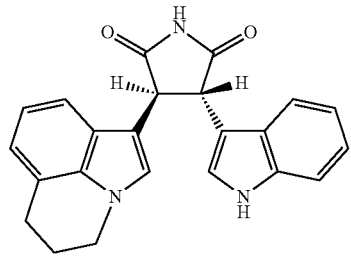

A preparation of (±)-cis-3-(5,6-dihydro-4H-pyrrolo[3,2,1-ij]quinolin-1-yl)-4-(1H-indol-3-yl) pyrrolidine-2,5-dione (378 mg, 1.02 mmol) was heated to 50° C. in tert-butanol (10 mL) and potassium t-butoxide (11 mg, 98 μmol) for 16 hours. The mixture was poured into ethyl acetate (100 mL) and washed with water (100 mL). The organic layer was dried over anhydrous sodium sulfate and evaporated to dryness to give (±)-trans-3-(5,6-dihydro-4H-pyrrolo[3,2,1-ij]quinolin-1-yl)-4-(1H-indol-3-yl) pyrrolidine-2,5-dione as a tan powder (276 mg). $^1$H NMR (DMSO-d$_6$) 400 MHz δ: 11.54 (s, 1H), 11.03 (s, 1H), 7.32-7.4 (m, 4H), 7.17 (d, 1H, J=7.2 Hz), 7.07 (t, 1H, J=7.6 Hz), 6.96 (t, 1H, J=7.6 Hz), 6.82-6.89 (m, 2H), 4.5 (dd, 2H, J=7.2 and 20 Hz), 4.07 (t, 2H, J=5.2 Hz), 2.87 (t, 2H, J=6 Hz), 2.08 (m, 2H).

Example 4

Chromatographic Separation of 3(R),4(S)-3-(5,6-Dihydro-4H-pyrrolo[3,2,1-ij]quinolin-1-yl)-4-(1H-indol-3-yl) pyrrolidine-2,5-dione and 3(S),4(R)-3-(5,6-Dihydro-4H-pyrrolo[3,2,1-ij]quinolin-1-yl)-4-(1H-indol-3-yl) pyrrolidine-2,5-dione A mixture of (±)-cis-3-(5,6-dihydro-4H-pyrrolo[3,2,1-ij]quinolin-1-yl)-4-(1H-indol-3-yl) pyrrolidine-2,5-dione (135 mg) in methanol (10 mL) and acetonitrile (6 mL) was subjected to preparative supercritical fluid chromatography, using a chiral AD column 20 mm×250 mm, eluting with 35% methanol/C02 at a flow rate of 3.5 mL/minutes. To give a faster eluting peak at 4.55 minutes (60 mg) assigned 3(R),4(S)-3-(5,6-dihydro-4H-pyrrolo[3,2,1-ij]quinolin-1-yl)-4-(1H-indol-3-yl) pyrrolidine-2,5-dione and a slower eluting peak 6.05 minutes (56 mg), assigned 3(S),4(R)-3-(5,6-dihydro-4H-pyrrolo[3,2,1-ij]quinolin-1-yl)-4-(1H-indol-3-yl) pyrrolidine-2,5-dione. The absolute stereochemical assignments were based solely upon the relative retention time of related compounds and may be reversed.

Example 5

Chromatographic Separation of 3(R),4(R)-3-(5,6-Dihydro-4H-pyrrolo[3,2,1-ij]quinolin-1-yl)-4-(1H-indol-3-yl) pyrrolidine-2,5-dione and 3(S),4(S)-3-(5,6-Dihydro-4H-pyrrolo[3,2,1-ij]quinolin-1-yl)-4-(1H-indol-3-yl) pyrrolidine-2,5-dione

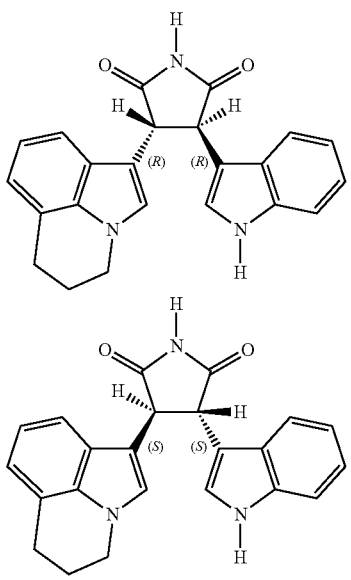

A mixture of (±)-trans-3-(5,6-dihydro-4H-pyrrolo[3,2,1-ij]quinolin-1-yl)-4-(1H-indol-3-yl) pyrrolidine-2,5-dione (200 mg) in acetonitrile (1 mL) was subjected to preparative supercritical fluid chromatography using a CHIRALPAK® AD column (Daicel, U.S.A.) 20 mm×250 mm, eluting with 35% methanol/C02 at a flow rate of 3.5 mL/minutes. Chromatography yielded a faster eluting peak of the trans isomer (82 mg) having a negative optical rotation assigned (−)-3(R),4(R)-3-(5,6-dihydro-4H-pyrrolo[3,2,1-ij]quinolin-1-yl)-4-(1H-indol-3-yl) pyrrolidine-2,5-dione and a slower eluting peak of the trans isomer (86 mg) having a positive optical rotation assigned (+)-3(S),4(R)-3-(5,6-dihydro-4H-pyrrolo[3,2,1-j]quinolin-1-yl)-4-(1H-indol-3-yl) pyrrolidine-2,5-dione. Absolute stereochemical assignments were based solely upon relative retention time of related compounds they may be reversed. All optical rotation measurements were conducted in chloroform at 25° C. at 589 nm.

Crystals of the chromatographically separated (+) or (−) isomers of trans-3-(5,6-dihydro-4H-pyrrolo[3,2,1-ij]quinolin-1-yl)-4-(1H-indol-3-yl) pyrrolidine-2,5-dione may be prepared from 2,2,2-trifluoroethanol using vapor stress techniques and slow evaporation at 49° C. Crystals of these isomers may also be prepared from ethanol at room temperature by evaporation employing seed crystals, such as those prepared by vapor stress techniques.

Example 6

Preparation of 3-(5,6-dihydro-4H-pyrrolo[3,2,1-ij]quinolin-1-yl)-4-(2-trifluoromethyl-phenyl)-pyrrole-2,5-dione 3-(5,6-Dihydro-4H-pyrrolo[3,2,1-ij]quinolin-1-yl)-4-(2-trifluoromethyl-phenyl)-pyrrole-2,5-dione was prepared according to Example 1, steps 1-6, employing 2'-trifluoromethylphenyl acetamide in place of indole-3-acetamide in step 6. $^1$H NMR (CDCl$_3$) 400 MHz δ: 8.16 (s, 1H), 7.83 (d, 2H, J=7.2 Hz), 7.58 (m, 2H), 7.37 (d, 1H, J=7.6 Hz), 7.33 (s, 1H), 6.85 (d, 1H, J=6.8 Hz), 6.66 (t, 1H, J=7.2 Hz), 5.96 (d, 1H, J=8.8 Hz), 4.2 (t, 2H, J=5.6 Hz), 2.95 (t, 2H, J=6.4 Hz), 2.22 (m, 2H).

Example 7

Preparation of 3-(5,6-Dihydro-4H-pyrrolo[3,2,1-ij]quinolin-1-yl)-4-thiophen-2-yl-pyrrole-2,5-dione 3-(5,6-Dihydro-4H-pyrrolo[3,2,1-ij]quinolin-1-yl)-4-thiophen-2-yl-pyrrole-2,5-dione was prepared according to Example 1, steps 1-6, employing 2-thienylacetamide in place of indole-3-acetamide in step 6. $^1$H NMR (CDCl$_3$) 400 MHz δ: 7.87 (s, 1H), 7.49 (d, 1H, J=5.2 Hz), 7.37 (s, 1H), 7.3 (d, 1H, J=4 Hz), 7.02 (t, 1H, J=4 Hz), 6.89-6.98 (m, 2H), 6.53 (d, 1H, J=7.6 Hz), 4.92 (t, 2H, J=6 Hz), 3.04 (t, 2H, J=6 Hz), 2.31 (m, 2H).

Example 8

Preparation of 3-(5,6-Dihydro-4H-pyrrolo[3,2,1-ij]quinolin-1-yl)-4-(3-methoxy-phenyl)-pyrrole-2,5-dione 3-(5,6-Dihydro-4H-pyrrolo[3,2,1-ij]quinolin-1-yl)-4-(3-methoxy-phenyl)-pyrrole-2,5-dione was prepared according to Example 1, steps 1-6, employing 3-methoxyphenylacetamide in place of indole-3-acetamide in step 6. $^1$H NMR (CDCl$_3$) 400 MHz δ: 8.01 (s, 1H), 7.31 (s, 1H), 7.23 (t, 1H, J=7.6 Hz), 7.09 (m, 2H), 6.87-6.92 (m, 2H), 6.73 (t, 1H, J=7.6 Hz), 6.14 (d, 1H, J=8 Hz), 4.25 (t, 2H, J=5.2 Hz), 2.99 (t, 2H, J=5.6 Hz), 2.67 (m, 2H).

Example 9

Preparation of 3-(5,6-Dihydro-4H-pyrrolo[3,2,1-ij]quinolin-1-yl)-4-pyridin-2-yl-pyrrole-2,5-dione 3-(5,6-Dihydro-4H-pyrrolo[3,2,1-ij]quinolin-1-yl)-4-pyridin-2-yl-pyrrole-2,5-dione was prepared according to Example 1, steps 1-6, employing pyridin-2-ylacetamide in place of indole-3-acetamide in step 6. $^1$H NMR (CDCl$_3$) 400 MHz δ: 8.58 (d, 1H, J=4.4 Hz), 8.12 (s, 1H), 7.78 (dt, 1H, J=1.6 and 7.6 Hz), 7.68 (d, 1H, J=8 Hz), 7.31 (s, 1H), 7.25 (m, 1H), 6.87 (d, 1H, J=6 Hz), 6.68 (t, 1H, J=8 Hz), 5.91 (d, 1H, J=7.6 Hz), 4.24 (t, 2H, J=5.6 Hz), 2.97 (t, 2H, J=6 Hz), 2.25 (m, 2H).

Example 10

Preparation of 3-(5,6-Dihydro-4H-pyrrolo[3,2,1-ij]quinolin-1-yl)-4-(4-methoxy-phenyl)-pyrrole-2,5-dione 3-(5,6-Dihydro-4H-pyrrolo[3,2,1-ij]quinolin-1-yl)-4-(4-methoxy-phenyl)-pyrrole-2,5-dione was prepared according to Example 1, steps 1-6, employing 4-methoxyphenylacetamide in place of indole-3-acetamide in step 6. $^1$H NMR (CDCl$_3$) 400 MHz δ: 7.95 (s, 1H), 7.51 (m, 2H), 7.25 (s, 1H), 6.85-6.89 (m, 3H), 6.75 (t, 1H, J=8 Hz), 6.24 (d, 1H, J=8 Hz), 4.26 (t, 2H, J=5.6 Hz), 3.82 (s, 3H), 2.99 (t, 2H, J=6.4 Hz), 2.27 (m, 2H).

Example 11

Preparation of 3-Benzo[1,3]dioxol-5-yl-4-(5,6-dihydro-4H-pyrrolo[3,2,1-ij]quinolin-1-yl)-pyrrole-2,5-dione 3-Benzo[1,3]dioxol-5-yl-4-(5,6-dihydro-4H-pyrrolo[3,2,1-ij]quinolin-1-yl)-pyrrole-2,5-dione was prepared according to Example 1, steps 1-6, employing 3,4-(methylenedioxy)phenylacetamide in place of indole-3-acetamide in step 6. $^1$H NMR (CDCl$_3$) 400 MHz δ: 7.98 (s, 1H), 7.04-7.07 (m, 2H), 6.90 (d, 1H, J=7.2 Hz), 6.76-6.82 (m, 2H), 6.30 (d, 1H, J=8 Hz), 5.98 (s, 2H,), 4.26 (t, 2H, J=5.6 Hz), 2.99 (t, 2H, J=6 Hz), 2.28 (m, 2H).

Example 12

Preparation of 3-(5,6-Dihydro-4H-pyrrolo[3,2,1-ij]quinolin-1-yl)-4-phenyl-pyrrole-2,5-dione 3-(5,6-Dihydro-4H-pyrrolo[3,2,1-ij]quinolin-1-yl)-4-phenyl-pyrrole-2,5-dione was prepared according to Example 1, steps 1-6, employing phenylacetamide in place of indole-3-acetamide in step 6. $^1$H NMR (CDCl$_3$) 400 MHz δ: 8.01 (s, 1H), 7.52 (m, 2H), 7.35 (m, 3H), 7.27 (s, 1H), 6.87 (d, 1H, J=7.2 Hz), 6.7 (t, 1H, J=7.2 Hz), 6.08 (d, 1H, J=8 Hz), 4.26 (t, 2H, J=5.6 Hz), 2.99 (t, 2H, J=5.6 Hz), 2.27 (m, 2H).

Example 13

Preparation of 3-Benzo[b]thiophen-2-yl-4-(5,6-dihydro-4H-pyrrolo[3,2,1-ij]quinolin-1-yl)-pyrrole-2,5-dione 3-Benzo[b]thiophen-2-yl-4-(5,6-dihydro-4H-pyrrolo[3,2,1-ij]quinolin-1-yl)-pyrrole-2,5-dione was prepared according to Example 1, steps 1-6, employing 2-benzothiophenylacetamide in place of indole-3-acetamide in step 6. $^1$H NMR (DMSO-d$_6$) 400 MHz δ: 11.11 (s, 1H), 8.14 (s, 1H), 8.01 (d, 1H, J=8 Hz), 7.84 (s, 1H), 7.45 (d, 1H, J=8 Hz), 7.3 (t, 1H, J=7.2 Hz), 7.15 (t, 1H, J=7.6 Hz), 6.71 (d, 1H, J=6.8 Hz), 6.43 (t, 1H, J=7.6 Hz), 5.99 (d, 1H, J=8 Hz), 4.26 (t, 2H, J=5.2 Hz), 2.86 (t, 2H, J=5.6 Hz), 2.1 (m, 2H).

Example 14

Preparation of 3-(5,6-Dihydro-4H-pyrrolo[3,2,1-ij]quinolin-1-yl)-4-(3-phenoxy-phenyl)-pyrrole-2,5-dione 3-(5,6-Dihydro-4H-pyrrolo[3,2,1-ij]quinolin-1-yl)-4-(3-phenoxy-phenyl)-pyrrole-2,5-dione was prepared according to Example 1, steps 1-6, employing 3-phenoxyphenylacetamide in place of indole-3-acetamide in step 6. $^1$H NMR (DMSO-d$_6$) 400 MHz δ: 11.03 (s, 1H), 8.01 (s, 1H), 7.43 (t, 1H, J=7.6 Hz), 7.28 (d, 1H, J=7.6 Hz), 7.15 (t, 2H, J=7.6 Hz), 7.03 (t, 2H, J=7.6 Hz), 6.92 (d, 1H, J=6.8 Hz), 6.8 (s, 1H), 6.76 (t, 1H, J=8 Hz), 6.60 (d, 2H, J=7.6 Hz), 6.08 (d, 1H, J=8 Hz), 4.27 (t, 2H, J=5.6 Hz), 2.97 (t, 2H, J=6 Hz), 2.16 (m, 2H).

Example 15

Preparation of 3-(5,6-Dihydro-4H-pyrrolo[3,2,1-ij]quinolin-1-yl)-4-(3-chloro-phenyl)-pyrrole-2,5-dione 3-(5,6-Dihydro-4H-pyrrolo[3,2,1-ij]quinolin-1-yl)-4-(3-chloro-phenyl)-pyrrole-2,5-dione was prepared according to Example 1, steps 1-6, employing 3-chlorophenylacetamide in place of indole-3-acetamide in step 6. $^1$H NMR (DMSO-d$_6$) 400 MHz δ: 11.11 (s, 1H), 8.13 (s, 1H), 7.47-7.43 (m, 2H), 7.36 (t, 1H, J=7.6 Hz), 7.29 (d, 1H, J=7.6 Hz), 6.86 (d, 1H, J=6.8 Hz), 6.68 (t, 1H, J=7.6 Hz), 5.97 (d, 1H, J=8 Hz), 4.31 (t, 2H, J=5.6 Hz), 2.93 (t, 2H, J=5.6 Hz), 2.16 (m, 2H).

Example 16

Preparation of 3-(5,6-Dihydro-4H-pyrrolo[3,2,1-ij]quinolin-1-yl)-4-(2-chloro-phenyl)-pyrrole-2,5-dione 3-(5,6-Dihydro-4H-pyrrolo[3,2,1-ij]quinolin-1-yl)-4-(2-chloro-phenyl)-pyrrole-2,5-dione was prepared according to Example 1, steps 1-6, employing 2-chlorophenylacetamide in place of indole-3-acetamide in step 6. $^1$H NMR (DMSO-d$_6$) 400 MHz δ: 11.1 (s, 1H), 8.17 (s, 1H), 7.55 (d, 1H, J=8 Hz), 7.45-7.49 (m, 1H), 7.36 (d, 2H, J=4.4 Hz), 6.81 (d, 1H, J=7.2 Hz), 6.58 (t, 1H, J=8 Hz), 5.92 (d, 1H, J=8.4 Hz), 4.27 (m, 2H), 2.89 (t, 2H, J=6 Hz), 2.11 (m, 2H).

Example 17

Preparation of 3-(5,6-Dihydro-4H-pyrrolo[3,2,1-ij]quinolin-1-yl)-4-(2,5-dimethoxyphenyl)-pyrrole-2,5-dione 3-(5,6-Dihydro-4H-pyrrolo[3,2,1-ij]quinolin-1-yl)-4-(2,5-dimethoxy-phenyl)-pyrrole-2,5-dione was prepared according to Example 1, steps 1-6, employing 2,5-dimethoxyphenylacetamide in place of indole-3-acetamide in step 6. $^1$H NMR (DMSO-d$_6$) 400 MHz δ: 10.93 (s, 1H), 8.06 (s, 1H), 6.97 (s, 2H), 6.81 (d, 1H, J=7.6 Hz), 6.77 (s, 1H), 6.6 (t, 1H, J=8 Hz), 5.92 (d, 1H, J=8 Hz), 4.26 (t, 2H, J=5.2 Hz), 3.63 (s, 3H), 3.3 (s, 3H), 2.9 (t, 2H, J=5.6 Hz), 2.11 (m, 2H).

Example 18

Preparation of 3-(5,6-Dihydro-4H-pyrrolo[3,2,1-ij]quinolin-1-yl)-4-(2-chloro-4-fluoro-phenyl)-pyrrole-2,5-dione 3-(5,6-Dihydro-4H-pyrrolo[3,2,1-ij]quinolin-1-yl)-4-(2-chloro-4-fluoro-phenyl)-pyrrole-2,5-dione was prepared according to Example 1, steps 1-6, employing 2-chloro-4-fluorophenylacetamide in place of indole-3-acetamide in step 6. $^1$H NMR (DMSO-d$_6$) 400 MHz δ: 11.11 (s, 1H), 8.16 (s, 1H), 7.57 (dd, 1H, J=2.8 and 9.2 Hz), 7.44 (dd, 1H, J=6.8 and 8.4 Hz), 7.28 (dt, 1H, J=2.4 and 8.4 Hz), 6.84 (d, 1H, J=7.2 Hz), 6.66 (t, 1H, J=8 Hz), 5.98 (d, 1H, J=8 Hz), 4.27 (m, 2H), 2.9 (t, 2H, J=5.6 Hz), 2.11 (m, 2H).

Example 19

Preparation of 3-(5,6-Dihydro-4H-pyrrolo[3,2,1-ij]quinolin-1-yl)-4-naphthalene-1-yl-pyrrole-2,5-dione 3-(5,6-Dihydro-4H-pyrrolo[3,2,1-ij]quinolin-1-yl)-4-naphthalene-1-yl-pyrrole-2,5-dione was prepared according to Example 1, steps 1-6, employing 1-naphthylacetamide in place of indole-3-acetamide in step 6. $^1$H NMR (DMSO-d$_6$) 400 MHz δ: 11.1 (s, 1H), 8.17 (s, 1H), 8.02 (d, 1H, J=8 Hz), 7.97 (d, 1H, J=8 Hz), 7.75 (d, 1H, J=8 Hz), 7.43-7.55 (m, 3H), 7.37 (t, 1H, J=8 Hz), 6.66 (d, 1H, J=6.8 Hz), 6.27 (t, 1H, J=8 Hz), 5.57 (d, 1H, J=8 Hz), 4.24 (t, 2H, J=5.2 Hz), 2.83 (t, 2H, J=5.6 Hz), 2.08 (m, 2H).

Example 20

Preparation of 3-(5,6-Dihydro-4H-pyrrolo[3,2,1-ij] quinolin-1-yl)-4-(2,6-dichloro-phenyl)-pyrrole-2,5-dione 3-(5,6-Dihydro-4H-pyrrolo[3,2,1-ij]quinolin-1-yl)-4-(2, 6-dichloro-phenyl)-pyrrole-2,5-dione was prepared according to Example 1, steps 1-6, employing 2,6-dichlorophenylacetamide in place of indole-3-acetamide in step 6. $^1$H NMR (DMSO-$d_6$) 400 MHz δ: 11.23 (s, 1H), 8.27 (s, 1H), 7.53-7.62 (m, 3H), 6.85 (d, 1H, J=7.2 Hz), 6.64 (t, 1H, J=8.4 Hz), 6.01 (d, 1H, J=8 Hz), 4.27 (t, 2H, J=5.6 Hz), 2.9 (t, 2H, J=5.6 Hz), 2.11 (m, 2H).

Example 21

Preparation of 3-(5,6-Dihydro-4H-pyrrolo[3,2,1-ij] quinolin-1-yl)-4-(2-bromo-phenyl)-pyrrole-2,5-dione 3-(5,6-Dihydro-4H-pyrrolo[3,2,1-ij]quinolin-1-yl)-4-(2-bromo-phenyl)-pyrrole-2,5-dione was prepared according to Example 1, steps 1-6, employing 2-bromophenylacetamide in place of indole-3-acetamide in step 6. $^1$H NMR (DMSO-$d_6$) 400 MHz δ: 11.09 (s, 1H), 8.17 (s, 1H), 7.75 (m, 1H), 7.37 (m, 2H), 7.33 (m, 1H), 6.81 (d, 1H, J=7.2 Hz), 6.58 (t, 1H, J=8 Hz), 5.95 (d, 1H, J=8 Hz), 4.26 (t, 2H, J=5.6 Hz), 2.9 (t, 2H, J=5.6 Hz), 2.11 (m, 2H).

Example 22

Preparation of 3-(5,6-Dihydro-4H-pyrrolo[3,2,1-ij] quinolin-1-yl)-4-indol-1-yl-pyrrole-2,5-dione 3-(5,6-Dihydro-4H-pyrrolo[3,2,1-ij]quinolin-1-yl)-4-indol-1-yl-pyrrole-2,5-dione was prepared according to Example 1, steps 1-6, employing N-indolyl-2-acetamide in place of indole-3-acetamide in step 6. $^1$H NMR (DMSO-$d_6$) 400 MHz δ: 11.21 (s, 1H), 8.18 (s, 1H), 7.58 (d, 1H, J=8 Hz), 7.52 (d, 1H, J=3.2 Hz), 7.01 (m, 2H), 6.91 (t, 1H, J=6.8 Hz), 6.74 (d, 1H, J=2.8 Hz), 6.71 (d, 1H, J=7.2 Hz), 6.4 (t, 1H, J=8 Hz), 5.63 (d, 1H, J=8 Hz), 4.28 (t, 2H, J=4.8 Hz), 2.85 (t, 2H, J=5.6 Hz), 2.11 (m, 2H).

Example 23

Preparation of 3-(5,6-Dihydro-4H-pyrrolo[3,2,1-ij] quinolin-1-yl)-4-pyridine-3-yl-pyrrole-2,5-dione 3-(5,6-Dihydro-4H-pyrrolo[3,2,1-ij]quinolin-1-yl)-4-pyridine-3-yl-pyrrole-2,5-dione was prepared according to Example 1, steps 1-6, employing pyridine-3-ylacetamide in place of indole-3-acetamide in step 6. $^1$H NMR (DMSO-$d_6$) 400 MHz δ: 11.14 (s, 1H), 8.53 (m, 2H), 8.12 (s, 1H), 7.78 (d, 1H, J=7.6 Hz), 7.41 (dd, 1H, J=4.8 and 8 Hz), 6.86 (d, 1H, J=7.2 Hz), 6.66 (t, 1H, J=7.6 Hz), 5.97 (d, 1H, J=8.4 Hz), 4.3 (t, 2H, J=5.2 Hz), 2.93 (t, 2H, J=5.6 Hz), 2.16 (m, 2H).

Example 24

Preparation of 3-(5,6-Dihydro-4H-pyrrolo[3,2,1-ij] quinolin-1-yl)-4-(5-bromo-1H-indol-3-yl)-pyrrole-2, 5-dione 3-(5,6-Dihydro-4H-pyrrolo[3,2,1-ij]quinolin-1-yl)-4-(5-bromo-1H-indol-3-yl)-pyrrole-2,5-dione was prepared according to Example 1, steps 1-6, employing 5-bromo-1H-indolyl-3-ylacetamide in place of indole-3-acetamide in step 6. $^1$H NMR (DMSO-$d_6$) 400 MHz δ: 11.77 (s, 1H), 10.92 (s, 1H), 7.82 (s, 1H), 7.69 (d, 1H, J=2.4 Hz), 7.33 (d, 1H, J=8.4 Hz), 7.10 (dd, 1H, J=2 and 8.4 Hz), 6.99 (d, 1H, J=1.6 Hz), 6.76 (d, 1H, J=7.2 Hz), 6.55 (t, 1H, J=8 Hz), 6.36 (d, 1H, J=8 Hz), 4.25 (t, 2H, J=5.6 Hz), 2.92 (t, 2H, J=5.6 Hz), 2.17 (m, 2H).

Example 25

Preparation of 3-(5,6-Dihydro-4H-pyrrolo[3,2,1-ij] quinolin-1-yl)-4-pyridine-4-yl-pyrrole-2,5-dione 3-(5,6-Dihydro-4H-pyrrolo[3,2,1-ij]quinolin-1-yl)-4-pyridine-4-yl-pyrrole-2,5-dione was prepared according to Example 1, steps 1-6, employing pyridine-4-ylacetamide in place of indole-3-acetamide in step 6. $^1$H NMR (DMSO-$d_6$) 400 MHz δ: 11.17 (s, 1H), 8.53 (m, 2H), 8.54 (d, 2H, J=6 Hz), 8.17 (s, 1H), 7.32 (d, 2H, J=4.8 Hz), 6.88 (d, 1H, J=7.2 Hz), 6.69 (t, 1H, J=7.6 Hz), 5.93 (d, 1H, J=8 Hz), 4.31 (t, 2H, J=6 Hz), 2.94 (t, 2H, J=6 Hz), 2.16 (m, 2H).

Example 26

Preparation of 3-Biphenyl-4-yl-4-(5,6-dihydro-4H-pyrrolo[3,2,1-ij]quinolin-1-yl)-pyrrole-2,5-dione 3-Biphenyl-4-yl-4-(5,6-dihydro-4H-pyrrolo[3,2,1-ij]quinolin-1-yl)-pyrrole-2,5-dione was prepared according to Example 1, steps 1-6, employing 4-phenylphenylacetamide in place of indole-3-acetamide in step 6. $^1$H NMR (acetone-$d_6$) 400 MHz δ: 8.08 (s, 1H), 7.6-7.73 (m, 7H), 7.48 (t, 2H, J=6.8 Hz), 7.39 (d, 1H, J=7.2 Hz), 6.84 (d, 1H, J=8 Hz), 6.65 (t, 1H, J=8.4 Hz), 6.23 (t, 1H, J=7.2 Hz), 5.97 (d, 1H, J=8.4 Hz), 4.38 (m, 2H), 2.98 (m, 2H), 2.28 (m, 2H).

Example 27

Preparation of 3-(5,6-Dihydro-4H-pyrrolo[3,2,1-ij] quinolin-1-yl)-4-(4-methanesulfonyl-phenyl)-pyrrole-2,5-dione 3-(5,6-Dihydro-4H-pyrrolo[3,2,1-ij]quinolin-1-yl)-4-(4-methanesulfonyl-phenyl)-pyrrole-2,5-dione was prepared according to Example 1, steps 1-6, employing 4-methanesulfonylphenylacetamide in place of indole-3-acetamide in step 6. $^1$H NMR (CDCl$_3$) 400 MHz δ: 8.09 (s, 1H), 7.9 (d, 2H, J=8.4 Hz), 7.71 (d, 2H, J=8.4 Hz), 7.64 (s, 1H), 6.91 (d, 1H, J=7.2 Hz), 6.73 (t, 1H, J=7.6 Hz), 5.95 (d, 1H, J=8.4 Hz), 4.29 (t, 2H, J=5.6 Hz), 3.06 (s, 3H), 3.0 (t, 2H, J=6 Hz), 2.29 (m, 2H).

Example 28

Preparation of 3-(5,6-Dihydro-4H-pyrrolo[3,2,1-ij] quinolin-1-yl)-4-(2-trifluoromethyl-quinolin-4-yl-sulfanyl)-pyrrole-2,5-dione 3-(5,6-Dihydro-4H-pyrrolo[3,2,1-ij]quinolin-1-yl)-4-(2-trifluoromethyl-quinolin-4-yl-sulfanyl)-pyrrole-2,5-dione was prepared according to Example 1, steps 1-6, employing 2-[[2-(trifluoromethyl)-4-quinolinyl]thio]acetamide in place of indole-3-acetamide in step 6. $^1$H NMR (CDCl$_3$) 400 MHz δ: 8.3 (d, 1H, J=7.6 Hz), 8.11 (d, 1H, J=8.4 Hz), 8.05 (s, 1H), 7.68-7.82 (m, 4H), 7.23 (s, 1H), 6.83 (m, 2H), 4.21 (t, 2H, J=6 Hz), 2.92 (t, 2H, J=6 Hz), 2.21 (m, 2H).

Example 29

Preparation of 3-(4-Benzoyloxyphenyl)-4-(5,6-dihydro-4H-pyrrolo[3,2,1-ij]quinolin-1-yl)-pyrrole-2,5-dione 3-(4-Benzoyloxyphenyl)-4-(5,6-dihydro-4H-pyrrolo[3,2,1-ij]quinolin-1-yl)-pyrrole-2,5-dione was prepared according to Example 1, steps 1-6, employing 4-benzyloxyphenylacetamide in place of indole-3-acetamide in step 6. $^1$H NMR (CDCl$_3$) 400 MHz δ: 7.95 (s, 1H), 7.5 (d, 2H, J=8.8 Hz), 7.33-7.43 (m, 6H), 6.93 (d, 2H, J=8.8 Hz), 6.88 (d, 1H, J=7.2 Hz), 6.73 (t, 1H, J=7.2 Hz), 6.23 (d, 1H, J=8.4 Hz), 5.08 (s, 2H), 4.25 (t, 2H, J=5.6 Hz), 2.99 (t, 2H, J=6 Hz), 2.27 (m, 2H).

Example 30

Preparation of 3-(5,6-Dihydro-4H-pyrrolo[3,2,1-ij]quinolin-1-yl)-4-[4-(2-morpholin-4-yl-ethoxy)-phenyl]-pyrrole-2,5-dione 3-(5,6-Dihydro-4H-pyrrolo[3,2,1-ij]quinolin-1-yl)-4-[4-(2-morpholin-4-yl-ethoxy)-phenyl]-pyrrole-2,5-dione was prepared according to Example 1, steps 1-6, employing 4-(2-morpholin-4-yl-ethoxy)-phenylacetamide in place of indole-3-acetamide in step 6. $^1$H NMR (CDCl$_3$) 400 MHz δ: 7.95 (s, 1H), 7.48 (m, 3H), 6.86 (m, 3H), 6.74 (t, 1H, J=8 Hz), 6.23 (d, 1H, J=8. Hz), 4.26 (t, 2H, J=5.2 Hz), 4.16 (t, 2H, J=5.6 Hz), 3.77 (t, 4H, J=4.8 Hz), 2.99 (t, 2H, J=6 Hz), 2.87 (t, 2H, J=5.2 Hz), 2.65 (m, 4H), 2.28 (m, 2H).

Example 31

Preparation of 3-(5,6-Dihydro-4H-pyrrolo[3,2,1-ij]quinolin-1-yl)-4-(5-1-naphthyl-1H-indol-3-yl) pyrrole-2,5-dione A mixture of 1-naphthyl boronic acid (41 mg, 0.24 mmol), 3-(5,6-dihydro-4H-pyrrolo[3,2,1-ij]quinolin-1-yl)-4-(5-bromo-1H-indol-3-yl) pyrrole-2,5-dione (88 mg, 0.2 mmol) (prepared as in Example 24), tetrakistriphenylphosphine palladium (5 mol %) in toluene (4 mL), ethanol (4 mL), saturated NaHCO$_3$ (1 mL), and water (2 mL) was heated at 100° C. under nitrogen for 5 hours. After cooling to room temperature, the mixture was extracted with ethyl acetate (3×15 mL) and concentrated. The residue was purified by silica gel chromatography, eluting with ethyl acetate/hexanes (1:4) to afford 3-(5,6-dihydro-4H-pyrrolo[3,2,1-ij]quinolin-1-yl)-4(5-1-naphthyl-1H-indol-3-yl) pyrrole-2,5-dione as a bright red solid (70 mg, 71%). $^1$H NMR (CD$_3$OD) δ: 1.80-1.92 (m, 2H), 2.72-2.80 (t, J=6.0 Hz, 2H), 3.94-3.99 (t, J=6.0 Hz, 2H), 6.50-6.58 (m, 3H), 6.66 (s, 1H), 6.72 (m, 1H), 6.98 (dd, J=8.4 Hz, J=2.0 Hz, 1H), 7.00-7.50 (m, 2H), 7.28 (dd, J=6.8 Hz, J'=8.4 Hz, 1H), 7.38-7.43 (m, 2H), 7.61 (s, 1H), 7.72 (d, J=8.4 Hz, 1H), 7.82 (d, J=8.4 Hz, 1H), 7.97 (s, 1H).

Example 32

Preparation of 3-(5,6-Dihydro-4H-pyrrolo[3,2,1-ij]quinolin-1-yl)-4-(5-phenyl-1H-indol-3-yl) pyrrole-2,5-dione 3-(5,6-Dihydro-4H-pyrrolo[3,2,1-ij]quinolin-1-yl)-4-(5-phenyl-1H-indol-3-yl) pyrrole-2,5-dione was prepared according to the method of Example 31 employing phenyl boronic acid in place of 1-naphthyl boronic acid. $^1$H NMR (CD$_3$OD) δ: 2.10-2.18 (m, 2H), 2.90 (t, J=5.6 Hz, 2H), 4.18 (t, J=5.6 Hz, 2H), 6.63 (t, J=7.6 Hz, 1H), 6.75-6.83 (m, 5H), 7.11-7.20 (m, 3H), 7.22 (dd, J=8.4 Hz, J'=1.2 Hz, 1H), 7.38 (d, J=8.4 Hz, 1H), 7.59 (s, 1H), 7.93 (s, 1H).

Example 33

Preparation of 3-(5,6-Dihydro-4H-pyrrolo[3,2,1-ij]quinolin-1-yl)-4-(5-(4-methoxyphenyl)-1H-indol-3-yl) pyrrole-2,5-dione 3-(5,6-Dihydro-4H-pyrrolo[3,2,1-ij]quinolin-1-yl)-4-(5-(4-methoxyphenyl)-1H-indol-3-yl) pyrrole-2,5-dione was prepared according to the method of Example 31 employing 4-methoxyphenyl boronic acid in place of 1-naphthyl boronic acid. $^1$H NMR (CD$_3$OD) δ: 2.09-2.18 (m, 2H), 2.90 (t, J=6.0 Hz, 2H), 4.15 (t, J=6.0 Hz, 2H), 6.62-6.68 (m, 2H), 6.73 (s, 4H), 6.77-6.82 (m, 2H), 7.18 (d, J=8.4 Hz, 1H), 7.33 (d, J=8.4 Hz, 1H), 7.53 (s, 1H), 7.91 (s, 1H).

Example 34

Preparation of 3-(5,6-Dihydro-4H-pyrrolo[3,2,1-ij]quinolin-1-yl)-4-(5-(3-methylphenyl)-1H-indol-3-yl) pyrrole-2,5-dione 3-(5,6-Dihydro-4H-pyrrolo[3,2,1-ij]quinolin-1-yl)-4-(5-(3-methylphenyl)-1H-indol-3-yl) pyrrole-2,5-dione was prepared according to the method of Example 31 employing 3-methylphenyl boronic acid in place of 1-naphthyl boronic acid. $^1$H NMR (CD$_3$OD) δ: 2.00-2.10 (m, 2H), 2.11 (s, 3H), 2.81-2.88 (t, J=6.0 Hz, 2H), 4.03-4.11 (t, J=5.6 Hz, 2H), 6.50 (d, J=7.2 Hz, 1H), 6.64 (t, J=7.6 Hz, 1H), 6.74-6.81 (m, 3H), 6.86 (d, J=8.0 Hz, 1H), 6.94 (d, J=7.6 Hz, 1H), 7.03 (t, J=7.2 Hz, 1H), 7.22 (dd, J=8.4 Hz, J'=2.0 Hz, 1H), 7.36 (d, J=8.8 Hz, 1H), 7.48 (s, 1H), 7.90 (s, 1H).

Example 35

Preparation of (±)-Trans-3-(5,6-dihydro-4H-pyrrolo[3,2,1-ij]quinolin-1-yl)-4-(5-bromo-1H-indol-3-yl) pyrrolidine-2,5-dione 3-(5,6-Dihydro-4H-pyrrolo[3,2,1-ij]quinolin-1-yl)-4-(5-bromo-1H-indol-3-yl) pyrrole-2,5-dione, prepared as in Example 24, was reduced with Mg in methanol as described in Example 2, Procedure C, to yield (±)-trans-3-(5,6-dihydro-4H-pyrrolo[3,2,1-ij]quinolin-1-yl)-4-(5-bromo-1H-indol-3-yl) pyrrolidine-2,5-dione. $^1$H NMR (CD$_3$OD) δ: 2.18-2.26 (m, 2H), 2.96 (t, J=6.0 Hz, 2H), 4.12 (t, J=6.4 Hz, 2H), 4.40 (d, J=6.8 Hz, 1H), 4.52 (d, J=6.8 Hz, 1H), 6.86-6.96 (m, 2H), 7.08 (s, 1H), 7.13-7.30 (m, 5H)

Example 36

Preparation of (±)-Trans-3-(5,6-dihydro-4H-pyrrolo[3,2,1-ij]quinolin-1-yl)-4-(5-phenyl-1H-indol-3-yl) pyrrolidine-2,5-dione 3-(5,6-Dihydro-4H-pyrrolo[3,2,1-ij]quinolin-1-yl)-4-(5-phenyl-1H-indol-3-yl) pyrrole-2,5-dione, prepared as in Example 32, was reduced with Mg in methanol as described in Example 2, Procedure C, to yield (±)-trans-3-(5,6-dihydro-4H-pyrrolo[3,2,1-ij]quinolin-1-yl)-4-(5-phenyl-1H-indol-3-yl) pyrrolidine-2,5-dione. $^1$H NMR (CD$_3$OD) δ:

2.00-2.16 (m, 2H), 2.94 (t, J=6.0 Hz, 2H), 3.92-3.99 (m, 1H), 4.00-4.08 (m, 1H), 4.36 (d, J=6.4 Hz, 1H), 4.68 (d, J=6.4 Hz 1H), 6.88-6.97 (m, 2H), 7.04 (s, 1H), 7.12-7.15 (m, 1H), 7.17-7.47 (m, 9H).

Example 37

Preparation of (±)-Trans-3-(5,6-dihydro-4H-pyrrolo [3,2,1-ij]quinolin-1-yl)-4-(5-(1-naphthyl)-1H-indol-3-yl) pyrrolidine-2,5-dione 3-(5,6-Dihydro-4H-pyrrolo[3,2,1-ij]quinolin-1-yl)-4-(5-1-naphthyl-1H-indol-3-yl) pyrrole-2,5-dione, prepared as in Example 31, was reduced with Mg in methanol as described in Example 2, Procedure C, to yield (±)-trans-3-(5,6-dihydro-4H-pyrrolo[3,2,1-ij]quinolin-1-yl)-4-(5-(1-naphthyl)-1H-indol-3-yl) pyrrolidine-2,5-dione. $^1$H NMR (CD$_3$OD) δ: 1.85-1.95 (m, 1H), 1.95-2.05 (m, 1H), 2.74-2.88 (m, 2H), 3.72-3.83 (m, 1H), 3.88-3.98 (m, 1H), 4.40 (d, J=6.4 Hz, 1H), 4.62 (d, J=6.4 Hz, 1H), 6.80 (d, J=6.8 Hz, 1H), 6.78 (t, J=8.0 Hz, 1H), 7.46 (s, 1H), 7.07-7.13 (m, 2H), 7.18-7.23 (dd, J=8.4 Hz, J=1.6 Hz, 2H), 7.27-7.34 (m, 2H), 7.41-7.49 (m, 3H), 7.78-7.83 (dd, J=8.4 Hz, J=3.2 Hz, 2H), 7.86-7.90 (d, J=7.6 Hz, 1H).

Example 38

Preparation of (±)-Trans-3-(5,6-dihydro-4H-pyrrolo [3,2,1-ij]quinolin-1-yl)-4-(5-(4-methoxyphenyl)-1H-indol-3-yl) pyrrolidine-2,5-dione 3-(5,6-Dihydro-4H-pyrrolo[3,2,1-ij]quinolin-1-yl)-4-(5-(4-methoxyphenyl)-1H-indol-3-yl) pyrrole-2,5-dione, prepared as in Example 33, was reduced with Mg in methanol as described in Example 2, Procedure C, to yield (±)-trans-3-(5,6-dihydro-4H-pyrrolo[3,2,1-ij]quinolin-1-yl)-4-(5-(4-methoxyphenyl)-1H-indol-3-yl) pyrrolidine-2,5-dione. $^1$H NMR (CD$_3$OD) δ: 2.03-2.22 (m, 2H), 2.98 (t, J=6.0 Hz, 2H), 3.80 (s, 3H), 3.97-4.06 (m, 1H), 4.06-4.14 (m, 1H), 4.38 (d, J=6.8 Hz, 1H), 4.67 (d, J=6.8 Hz, 1H), 6.86 (d, J=8.4 Hz, 2H), 6.91-7.00 (m, 2H), 7.08 (s, 2H), 7.17-7.27 (m, 4H), 7.31 (d, J=8.4 Hz, 1H), 7.37 (d, J=8.8 Hz, 1H).

Example 39

(±)-Trans-3-(5,6-dihydro-4H-pyrrolo[3,2,1-ij]quinolin-1-yl)-4-(5-(3-methylphenyl)-1H-indol-3-yl) pyrrolidine-2,5-dione 3-(5,6-Dihydro-4H-pyrrolo[3,2,1-ij]quinolin-1-yl)-4-(5-(3-methylphenyl)-1H-indol-3-yl) pyrrole-2,5-dione, prepared as in Example 34, was reduced with Mg in methanol as described in Example 2, Procedure C, to yield (±)-trans-3-(5,6-dihydro-4H-pyrrolo[3,2,1-ij]quinolin-1-yl)-4-(5-(3-methylphenyl)-1H-indol-3-yl) pyrrolidine-2,5-dione. $^1$H NMR (CD$_3$OD) δ: 1.98-2.18 (m, 2H), 2.34 (s, 3H), 2.85-3.00 (m, 2H), 3.90-3.98 (m, 1H), 3.98-4.09 (m, 1H), 4.35 (d, J=7.2 Hz, 1H), 4.64 (d, J=6.8 Hz, 1H), 6.88-6.99 (m, 2H), 7.00-7.10 (m, 3H), 7.13-7.26 (m, 5H), 7.36 (m, 2H).

Example 40

Preparation of (±)-Trans-3-(5,6-dihydro-4H-pyrrolo [3,2,1-ij]quinolin-1-yl)-4-(2-chloro-4-fluorophenyl) pyrrolidine-2,5-dione To a solution of 5,6-dihydro-4H-pyrrolo[3,2,1-ij]quinolin-1-yl) oxoacetic acid methyl ester (0.243 g, 1 mmol) and 2-chloro-4-fluorophenylacetamide (1 mmol) in anhydrous tetrahydrofuran (5 mL) at 0° C. was added a solution of potassium t-butoxide (1 M in tetrahydrofuran) (2.5 mL, 2.5 mmol). The mixture was stirred at 0° C. for 2 hours. Concentrated hydrochloric acid (0.5 mL) was then added and the mixture stirred for 1 hour at room temperature. The mixture was then diluted with ethyl acetate (20 mL), washed with water (2×15 mL) and saturated aqueous sodium chloride solution (15 mL). The organic layer was then dried over anhydrous sodium sulfate and concentrated under reduced pressure to yield an oil. This residue was diluted in anhydrous methanol (15 mL) and the resulting solution charged with oven dried magnesium turnings (0.5 g, 20.5 mmol) and stirred at 70° C. in a ventilated vial until the Mg turnings fully dissolved or for two hours. The vial was then allowed to cool to room temperature. The mixture was diluted with ethyl acetate (25 mL) and washed with 10% hydrochloric acid (2×25 mL) and saturated aqueous sodium chloride solution (20 mL). The organic layer was dried over anhydrous sodium sulfate and concentrated under reduced pressure. The residue was purified by silica gel chromatography, eluting with an ethyl acetate/hexanes gradient (10% ethyl acetate to 50% ethyl acetate over 40 minutes) to yield (25.6 mg, 6.7%) of (±)-trans-3-(5,6-dihydro-4H-pyrrolo[3,2,1-ij]quinolin-1-yl)-4-(2-chloro-4-fluorophenyl) pyrrolidine-2,5-dione. $^1$H NMR (DMSO-d$_6$) 400 MHz δ: 12.5 (s, 1H), 7.52 (t, 1H, J=6.4 Hz), 7.49 (dd, 1H, J=6.4 2.4 Hz), 7.34 (s, 1H), 7.21 (td, 1H, J=6.0 2.8 Hz), 7.10 (d, 1H, J=7.6 Hz), 6.87 (m, 2H), 4.67 (d, 1H, J=8.0 Hz), 4.51 (d, 1H, J=7.2 Hz), 2.90 (t, 2H, J=5.6 Hz), 2.11 (t, 2H, J=5.2 Hz).

Example 41

Preparation of (±)-Trans-3-(5,6-dihydro-4H-pyrrolo [3,2,1-ij]quinolin-1-yl)-4-(2,6-dichlorophenyl) pyrrolidine-2,5-dione (±)-Trans-3-(5,6-dihydro-4H-pyrrolo[3,2,1-ij]quinolin-1-yl)-4-(2,6-dichlorophenyl) pyrrolidine-2,5-dione was prepared according to Example 40 replacing 2-chloro-4-fluorophenylacetamide with 2,6-dichlorophenylacetamide. Yield 52.2 mg, 13.0%. $^1$H NMR (DMSO-d$_6$) 400 MHz δ: 11.82 (s, 1H), 7.34 (m, 3H), 7.10 (d, 1H, J=7.2 Hz), 6.87 (m, 2H), 5.16 (d, 1H J=7.6 Hz), 5.10 (d, 1H, J=7.6 Hz), 2.91 (t, 2H, J=6.0 Hz) 2.10 (m, 2H).

Example 42

Preparation of (±)-Trans-3-(5,6-dihydro-4H-pyrrolo [3,2,1-ij]quinolin-1-yl)-4-(4-bromophenyl) pyrrolidine-2,5-dione (±)-Trans-3-(5,6-dihydro-4H-pyrrolo[3,2,1-ij]quinolin-1-yl)-4-(4-bromophenyl) pyrrolidine-2,5-dione was prepared according to Example 40 replacing 2-chloro-4-fluorophenylacetamide with 4-bromophenylacetamide. Yield 33.1 mg, 8.1%. $^1$H NMR (DMSO-d$_6$) 400 MHz δ: 11.55 (s, 1H), 7.53 (dt, 2H, J=8.8 2.0 Hz), 7.34 (dt, 3H, J=8.0 2.0 Hz), 7.15 (dd, 1H, J=7.6 1.0 Hz), 6.86 (m, 2H), 4.53 (d, 1H, J=8.0 Hz), 4.37 (d, 1H, J=8.0 Hz), 4.10 (t, 2H, J=1.6 Hz), 2.90 (t, 2H, J=2.0 Hz), 2.12 (t, 2H, J=1.8 Hz).

Example 43

Preparation of (±)-Trans-3-(5,6-dihydro-4H-pyrrolo [3,2,1-ij]quinolin-1-yl)-4-(4-chlorophenyl) pyrrolidine-2,5-dione (±)-Trans-3-(5,6-dihydro-4H-pyrrolo[3,2,1-ij]quinolin-1-yl)-4-(4-chlorophenyl) pyrrolidine-2,5-dione was prepared according to Example 40 replacing 2-chloro-4-fluorophenylacetamide with 4-chlorophenylacetamide. Yield 32.7 mg, 9.0%. $^1$H NMR (DMSO-d$_6$) 400 MHz δ: 11.54 (s, 1H), 7.40 (m, 4H), 7.33 (s, 1H), 7.15 (dd, 1H, J=6.8 0.8 Hz), 6.86 (m, 2H), 4.54 (d, 1H, J=8.0 Hz), 7.38 (d, 1H, J=7.6 Hz), 4.10 (t, 2H, J=5.6 Hz), 2.90 (t, 2H, J=6.0 Hz), 2.11 (m, 2H).

Example 44

Preparation of (±)-Trans-3-(5,6-dihydro-4H-pyrrolo[3,2,1-ij]quinolin-1-yl)-4-(4-trifluoromethoxyphenyl) pyrrolidine-2,5-dione (±)-Trans-3-(5,6-dihydro-4H-pyrrolo[3,2,1-ij]quinolin-1-yl)-4-(4-trifluoromethoxyphenyl) pyrrolidine-2,5-dione was prepared according to Example 40 replacing 2-chloro-4-fluorophenylacetamide with 4-trifluoromethoxyphenylacetamide. Yield 67.8 mg, 16.4%. $^1$H NMR (DMSO-d$_6$) 400 MHz δ: 11.56 (s, 1H), 7.52 (d, 2H, J=8.4 Hz), 7.35 (s, 1H), 7.33 (d, 2H, J=8.0 Hz), 7.15 (d, 1H, J=7.2 Hz), 6.86 (m, 2H), 4.58 (d, 1H, J=8.0 Hz), 4.45 (d, 1H, J=8.0 Hz), 4.10 (t, 2H, J=6.0 Hz), 2.90 (t, 2H, J=6.0), 2.10 (t, 2H, J=5.6).

Example 45

Preparation of (±)-Trans-3-(5,6-dihydro-4H-pyrrolo[3,2,1-ij]quinolin-1-yl)-4-(thiophen-3-yl) pyrrolidine-2,5-dione (±)-Trans-3-(5,6-dihydro-4H-pyrrolo[3,2,1-ij]quinolin-1-yl)-4-(thiophen-3-yl) pyrrolidine-2,5-dione was prepared according to Example 40 replacing 2-chloro-4-fluorophenylacetamide with thiophen-3-ylacetamide. Yield 50.3 mg, 15.0%. $^1$H NMR (DMSO-d$_6$) 400 MHz δ: 11.50 (s, 1H), 7.52 (m, 1H), 7.49 (m, 1H), 7.35 (s, 1H), 7.21 (dd, 1H, J=4.0 1.2 Hz), 7.16 (d, 1H, 7.6 Hz), 6.89 (d, 1H, J=4.4 Hz), 6.85 (t, 1H, J=6.8 Hz), 4.56 (d, 1H, J=7.2 Hz), 4.41 (d, 1H, J=7.2 Hz), 4.10 (t, 2H, J=6.0 Hz), 2.90 (t, 2H, J=6.0 Hz), 2.10 (m, 2H).

Example 46

Preparation of (±)-Trans-3-(5,6-dihydro-4H-pyrrolo[3,2,1-ij]quinolin-1-yl)-4-(2-fluorophenyl) pyrrolidine-2,5-dione (±)-Trans-3-(5,6-dihydro-4H-pyrrolo[3,2,1-ij]quinolin-1-yl)-4-(2-fluorophenyl) pyrrolidine-2,5-dione was prepared according to Example 40 replacing 2-chloro-4-fluorophenylacetamide with 2-fluorophenylacetamide. Yield 30.6 mg, 8.8%. $^1$H NMR (DMSO-d$_6$) 400 MHz δ: 11.64 (s, 1H), 7.36 (m, 3H), 7.17 (m, 3H), 6.84 (m, 2H), 4.44 (d, 1H, J=7.2 Hz), 4.40 (d, 1H, J=7.6 Hz), 4.10 (s, 2H), 2.88 (s, 2H), 2.09 (s, 2H).

Example 47

Preparation of (±)-Trans-3-(5,6-dihydro-4H-pyrrolo[3,2,1-ij]quinolin-1-yl)-4-(2-thiophen-2-yl) pyrrolidine-2,5-dione (±)-Trans-3-(5,6-dihydro-4H-pyrrolo[3,2,1-ij]quinolin-1-yl)-4-(2-thiophen-2-yl) pyrrolidine-2,5-dione was prepared according to Example 40 replacing 2-chloro-4-fluorophenylacetamide with 2-thiophen-2-ylacetamide. Yield 30.6 mg, 8.8%. $^1$H NMR (DMSO-d$_6$) 400 MHz δ: 11.58 (s, 1H), 7.45 (dd, 1H, J=5.2 0.8 Hz), 7.40 (s, 1H), 7.22 (d, 1H, J=8.0 Hz), 7.12 (d, 1H, J=3.2 Hz), 6.99 (dd, 1H, J=5.2 and 3.6 Hz), 4.63 (d, 1H, J=8.0 Hz), 4.60 (d, 1H, J=7.6 Hz), 2.90 (t, 2H, J=6.0 Hz), 2.12 (t, 2H, J=6.0 Hz).

Example 48

Preparation of (±)-Trans-3-(5,6-dihydro-4H-pyrrolo[3,2,1-ij]quinolin-1-yl)-4-(2,4-dichlorophenyl) pyrrolidine-2,5-dione (±)-Trans-3-(5,6-dihydro-4H-pyrrolo[3,2,1-ij]quinolin-1-yl)-4-(2,4-dichlorophenyl) pyrrolidine-2,5-dione was prepared according to Example 40 replacing 2-chloro-4-fluorophenylacetamide with 2,4-dichlorophenylacetamide. Yield 20.9 mg, 5.2%. $^1$H NMR (DMSO-d$_6$) 400 MHz δ: 11.65 (s, 1H), 7.69 (s, 1H), 7.51 (d, 1H, J=8.0 Hz), 7.43 (d, 1H, J=8.0 Hz), 7.34 (s, 1H), 7.12 (m, 1H), 6.87 (m, 2H), 4.65 (d, 1H, J=7.6 Hz), 4.55 (d, 1H, J=7.6 Hz), 4.10 (t, 2H, J=6.0 Hz), 2.90 (t, 2H, J=6.0), 2.12 (t, 2H, J=6.0 Hz).

Example 49

Preparation of (±)-Trans-3-(5,6-dihydro-4H-pyrrolo[3,2,1-ij]quinolin-1-yl)-4-phenyl-pyrrolidine-2,5-dione (±)-Trans-3-(5,6-dihydro-4H-pyrrolo[3,2,1-ij]quinolin-1-yl)-4-phenyl-pyrrolidine-2,5-dione was prepared according to the Example 40 replacing 2-chloro-4-fluorophenylacetamide with phenylacetamide. $^1$H NMR (DMSO-d$_6$) 400 MHz δ: 11.511 (s, 1H), 7.24-7.36 (m, 6H), 7.13 (d, 1H, J=7.2), 6.8-6.88 (m, 2H), 4.49 (d, 1H, J=8.0 Hz), 4.3 (d, 1H, J=7.6 Hz), 4.08 (m, 2H), 2.88 (m, 2H), 2.088 (m, 2H).

Example 50

Preparation of (±)-Trans-3-(5,6-dihydro-4H-pyrrolo[3,2,1-ij]quinolin-1-yl)-4-(2-chlorophenyl)-pyrrolidine-2,5-dione (±)-Trans-3-(5,6-dihydro-4H-pyrrolo[3,2,1-ij]quinolin-1-yl)-4-(2-chlorophenyl)-pyrrolidine-2,5-dione was prepared according to Example 40 replacing 2-chloro-4-fluorophenylacetamide with 2-chlorophenylacetamide. $^1$H NMR (DMSO-d$_6$) 400 MHz δ: 11.655 (s, 1H), 7.41-7.48 (m, 2H), 7.27-7.35 (m, 3H, J=7.2), 7.87 (d, 1H, J=7.6), 6.81-6.88 (m, 2H), 4.632 (d, 1H, J=7.6 Hz), 4.494 (d, 1H, J=7.2), 4.07-4.10 (m, 2H), 2.884 (m, 2H), 2.09 (m, 2H).

Example 51

Preparation of (±)-Trans-3-(5,6-dihydro-4H-pyrrolo[3,2,1-ij]quinolin-1-yl)-4-(N-methylindol-3-yl) pyrrolidine-2,5-dione (±)-Trans-3-(5,6-dihydro-4H-pyrrolo[3,2,1-ij]quinolin-1-yl)-4-(N-methylindol-3-yl) pyrrolidine-2,5-dione was prepared according to Example 40 replacing 2-chloro-4-fluorophenylacetamide with N-methylindol-3-ylacetamide. $^1$H NMR (DMSO-d$_6$) 400 MHz δ: 11.55 (s, 1H), 7.44-7.34 (m, 4H), 7.2-7.18 (m, 2H), 7.01 (t, 1H), 6.82-6.89 (m, 2H), 4.49 (dd, 2H), 4.093 (t, 2H), 4.093 (t, 2H), 3.73 (s, 3H), 2.89 (t, 2H), 2.07 (m, 2H).

Example 52

Preparation of (±)-Cis-3-(5,6-dihydro-4H-pyrrolo[3,2,1-ij]quinolin-1-yl)-4-(4-methoxyphenyl)-pyrrolidine-2,5-dione 3-(5,6-Dihydro-4H-pyrrolo[3,2,1-ij]quinolin-1-yl)-4(4-methoxy-phenyl)-pyrrole-2,5-dione, prepared as in Example 10 and was reduced by employing the method of Example 2, Protocol B, to yield (±)-cis-3-(5,6-dihydro-4H-pyrrolo[3,2,1-ij]quinolin-1-yl)-4-(4-methoxyphenyl)-pyrrolidine-2,5-dione. $^1$H NMR (CDCl$_3$) 400 MHz δ: 8.62 (s, 1H), 7.15 (d, 1H, J=7.6 Hz), 6.8-6.93 (m, 4H), 6.7 (s, 1H), 6.55 (d, 2H, J=8.4 Hz), 4.8 (d, 1H, J=8.8 Hz), 4.48 (d, 1H, J=8.8 Hz), 3.96 (m, 2H), 3.63 (s, 3H), 2.87 (t, 2H, J=6 Hz), 2.10 (m, 2H).

Example 53

Preparation of (±)-Cis-3-(5,6-dihydro-4H-pyrrolo[3,2,1-ij]quinolin-1-yl)-4-(2,5-dimethoxyphenyl)-pyrrolidine-2,5-dione 3-(5,6-Dihydro-4H-pyrrolo[3,2,1-ij]quinolin-1-yl)-4-(2,5-dimethoxy-phenyl)-pyrrole-2,5-dione, prepared as in Example 17, was reduced by employing the method of Example 2, Protocol B, to yield (±)-cis-3-(5,6-dihydro-4H-pyrrolo[3,2,1-ij]quinolin-1-yl)-4-(2,5-dimethoxyphenyl)-pyrrolidine-2,5-dione. $^1$H NMR (CDCl$_3$) 400 MHz δ: 8.0 (s, 1H), 7.19 (d, 1H, J=7.6 Hz), 6.89 (t, 1H, J=7.2 Hz), 6.77 (d, 2H, J=7.2 Hz), 6.44-6.51 (m, 3H), 4.84 (d, 2H, J=9.6 Hz), 3.88-4.00 (m, 2H), 3.6 (s, 3H), 3.49 (s, 3H), 2.8 (m, 2H), 2.05 (m, 2H).

Example 54

Preparation of (±)-Cis-3-(5,6-dihydro-4H-pyrrolo[3,2,1-ij]quinolin-1-yl)-4-(2-chloro-4-fluoro-phenyl)-pyrrolidine-2,5-dione 3-(5,6-Dihydro-4H-pyrrolo[3,2,1-ij]quinolin-1-yl)-4-(2-chloro-4-fluoro-phenyl)-pyrrole-2,5-dione, prepared as in Example 18, was reduced by employing the method of Example 2, Protocol B, to yield (±)-cis-3-(5,6-dihydro-4H-pyrrolo[3,2,1-ij]quinolin-1-yl)-4-(2-chloro-4-fluoro-phenyl)-pyrrolidine-2,5-dione. $^1$H NMR (DMSO-d$_6$) 400 MHz δ: 11.82 (s, 1H), 7.02-7.18 (m, 4H), 6.7-6.85 (m, 3H), 5.01 (d, 1H, J=9.2 Hz), 4.79 (d, 2H, J=9.6 Hz), 3.96 (m, 2H), 2.79 (m, 2H), 1.97 (m, 2H).

Example 55

Preparation of (±)-Cis-3-(5,6-dihydro-4H-pyrrolo[3,2,1-ij]quinolin-1-yl)-4-(3-chlorophenyl)-pyrrolidine-2,5-dione 3-(5,6-Dihydro-4H-pyrrolo[3,2,1-ij]quinolin-1-yl)-4-(3-chloro-phenyl)-pyrrole-2,5-dione, prepared as in Example 15, was reduced by employing the method of Example 2, Procedure B, to yield (±)-cis-3-(5,6-dihydro-4H-pyrrolo[3,2,1-ij]quinolin-1-yl)-4-(3-chlorophenyl)-pyrrolidine-2,5-dione. $^1$H NMR (DMSO-d$_6$) 400 MHz δ: 11.66 (s, 1H), 7.13 (d, 1H, J=8 Hz), 6.95-7.02 (m, 5H), 6.78 (t, 1H, J=7.6 Hz), 6.7 (d, 1H, J=7.2 Hz), 4.84 (d, 1H, J=9.2 Hz), 4.65 (d, 2H, J=8.8 Hz), 3.9-4.03 (m, 2H), 2.79 (t, 2H, J=5.6 Hz), 1.97 (m, 2H).

Example 56

Preparation of (±)-Phosphoric acid mono-[trans-3-(5,6-dihydro-4H-pyrrolo[3,2,1-ij]quinolin-1-yl)-4-(1H-indol-3-yl)-2,5-dioxo-pyrrolidin-1-ylmethyl] ester Step 1

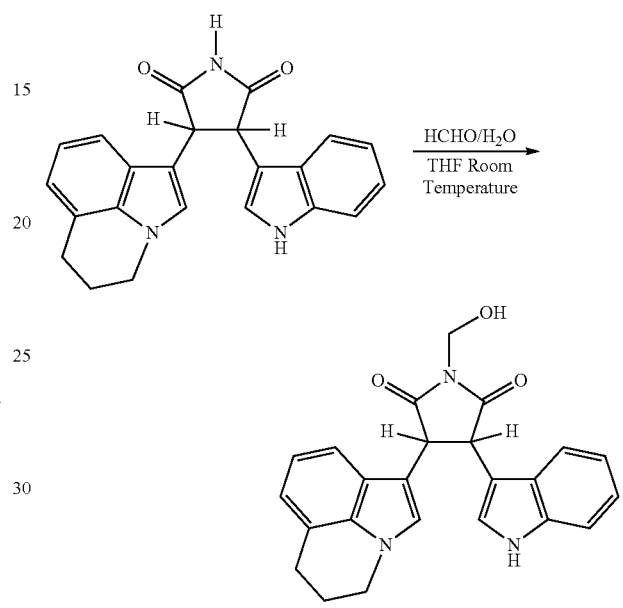

(±)-Trans-3-(5,6-dihydro-4H-pyrrolo[3,2,1-ij]quinolin-1-yl)-4-(1H-indol-3-yl) pyrrolidine-2,5-dione (3.0 g, 8.13 mmol, prepared as in Example 2, Procedure C) and formaldehyde (30 mL, 37% in water) in tetrahydrofuran (30 mL) were stirred for 14-16 hours at room temperature.

The mixture was then taken up in ethyl acetate (50 mL) and water (50 mL). The organic layer was washed with brine and dried over sodium sulfate. Solvent was removed under reduced pressure and residue was purified using a silica gel chromatography column eluted with EtOAc/Hexane 1:1 to yield 2.5 g, 77%, of (±)-trans-3-(5,6-dihydro-4H-pyrrolo[3,2,1-ij]quinolin-1-yl)-1-hydroxymethyl-4-(1H-indol-3-yl)-pyrrolidine-2,5-dione an orange foamy solid (2.5 g, 77%).

Step 2

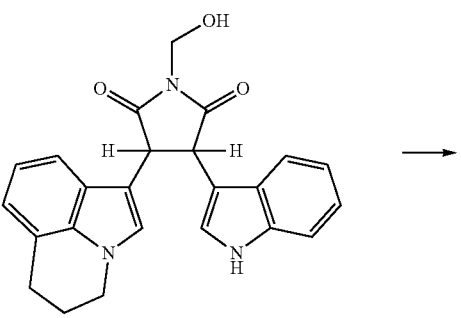

71
-continued

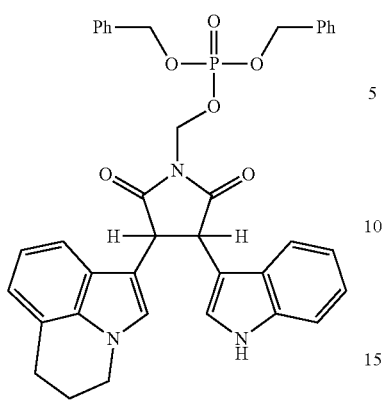

(±)-Trans-3-(5,6-Dihydro-4H-pyrrolo[3,2,1-ij]quinolin-1-yl)-1-hydroxymethyl-4-(1H-indol-3-yl)-pyrrolidine-2,5-dione (0.06 g) in anhydrous tetrahydrofuran (5 mL) was treated with dibenzylphosphoramidate (0.156 mL, 3.5 equivalents) followed by the addition of tetrazole (3% solution in acetonitrile, 2 mL). The reaction mixture was stirred at room temperature for 20 min and cooled to −78° C. A solution of m-chloroperbenzoic acid (70%, 0.162 g) in dichloromethane (2 mL) was added at −78° C. After 5 min at −78° C., the reaction was brought to room temperature and stirred for 5 min. Solvents were removed under reduced pressure and the residue was purified by flash chromatography on a silica column, eluted with ethyl acetate, hexane to give phosphoric acid dibenzyl ester trans-3-(5,6-dihydro-4H-pyrrolo[3,2,1-ij]quinolin-1-yl)-4-(1H-indol-3-yl)-2,5-dioxo-pyrrolidin-1-ylmethyl ester as a solid (70 mg). $^1$H NMR (DMSO-$d_6$) 400 MHz δ: 11.10 (s, 1H), 7.32-7.39 (m, 12H), 6.84-7.24 (m, 2H), 5.49 (brs, 2H), 5.03 (m, 4H), 4.61 (dd, 2H), 4.06 (brs, 2H), 2.87 (brs, 2H), 2.07 (brs, 2H).

Step 3,

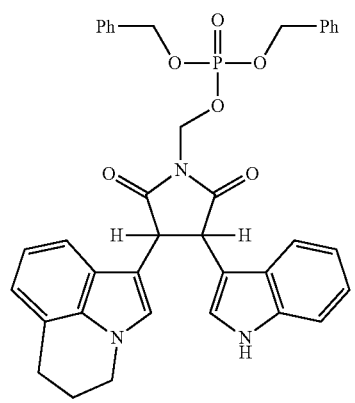

72
-continued

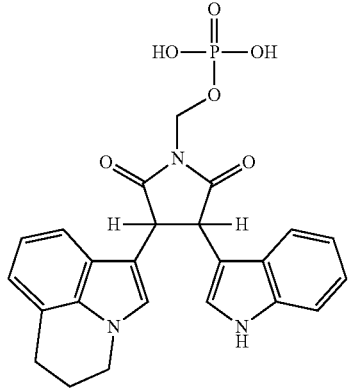

The phosphoric acid dibenzyl ester of (±)-trans-3-(5,6-dihydro-4H-pyrrolo[3,2,1-ij]quinolin-1-yl)-4-(1H-indol-3-yl)-2,5-dioxo-pyrrolidin-1-yl-methyl ester (0.160 g) in methanol (2 mL) and Pd/C (10%, 20 mg) was stirred at room temperature under 1 atmosphere of hydrogen for two hours. The mixture was filtered over Celite and the solvent removed to give (±)-phosphoric acid mono-[trans-3-(5,6-dihydro-4H-pyrrolo[3,2,1-ij]quinolin-1-yl)-4-(1H-indol-3-yl)-2,5-dioxo-pyrrolidin-1-ylmethyl]ester (0.110 g).

Example 57

Preparation of (±)-trans-2-Amino-propionic acid-3-(5,6-dihydro-4H-pyrrolo[3,2,1-ij]quinolin-1-yl)-4-(1H-indol-3-yl)-2,5-dioxo-pyrrolidin-1-yl methyl ester Step 1

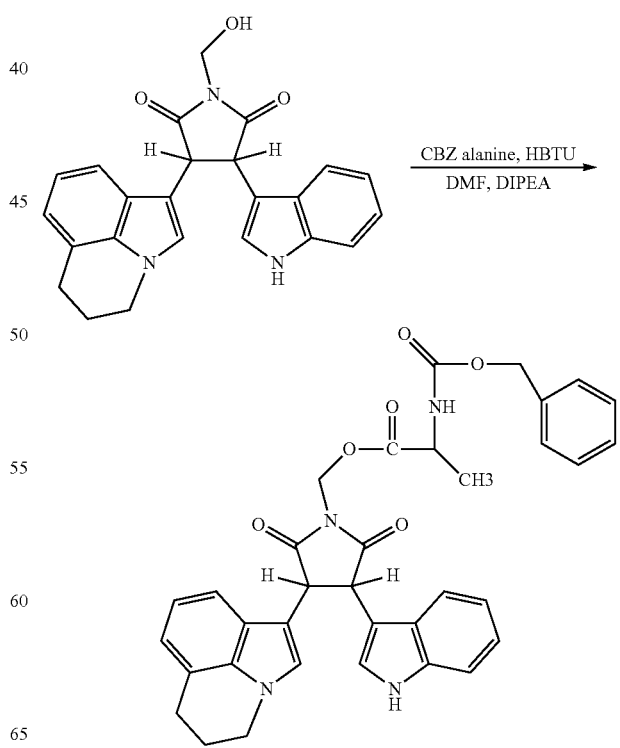

To a solution of (±)-trans-3-(5,6-dihydro-4H-pyrrolo[3,2,1-ij]quinolin-1-yl)-1-hydroxymethyl-4-(1H-indol-3-yl)-pyrrolidine-2,5-dione (0.5 mmol) in tetrahydrofuran (8 mL) was added N-carbobenzyloxy alanine (1.1 equivalents) followed by the addition of HBTU (1.5 equivalents) and DIPEA (2.2 equivalents). The mixture was stirred at room temperature for 15 h. The solvents were removed under reduced pressure and the residue was taken up in ethyl acetate and water (1:1, 15 mL). The organic layer was separated and dried. The residue was purified by silica gel chromatography to provide the N-carbobenzyloxy protected product.

Step 2

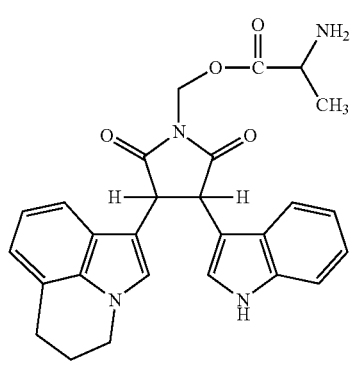 [SMILES: CC(N)C(=O)OCN1C(=O)C(c2c[nH]c3ccccc23)C(c2cn3c4c(cccc24)CCC3)C1=O]

A solution of the N-carbobenzyloxy protected product from Step 1 (0.5 mmol) in methanol (8 mL) and a few drops of 4 M HCl in ethyl acetate and 10% Pd/C (10% w/w) were stirred at room temperature under 1 atmosphere of hydrogen for 2 hours. The mixture was then filtered over celite and the solvent removed to provide final product (±)-trans-2-aminopropionic acid-3-(5,6-dihydro-4H-pyrrolo[3,2,1-ij]quinolin-1-yl)-4-(1H-indol-3-yl)-2,5-dioxo-pyrrolidin-1-ylmethyl ester. $^1$H NMR (DMSO-$d_6$) 400 MHz δ: 11.10 (s, 1H), 8.57 (s, 2H), 6.84-7.41 (m, 9H), 5.61 (m, 2H), 4.62 (dd, 2H), 4.07 (brs, 2H), 3.72 (brm, 1H), 2.87 (brs, 2H), 2.23 (s, 6H), 2.08 (brs, 2H), 1.40 (d, J=6.4 Hz, 3H).

Example 58

Preparation of (±)-trans-2-Amino-acetic acid-3-(5,6-dihydro-4H-pyrrolo[3,2,1-ij]quinolin-1-yl)-4-(1H-indol-3-yl)-2,5-dioxo-pyrrolidin-1-yl methyl ester (±)-trans-2-Amino-acetic acid-3-(5,6-dihydro-4H-pyrrolo[3,2,1-ij]quinolin-1-yl)-4-(1H-indol-3-yl)-2,5-dioxo-pyrrolidin-1-ylmethyl ester was prepared as in Example 57 by replacing N-carbobenzyloxy alanine with N-carbobenzyloxy glycine. $^1$H NMR (DMSO-$d_6$) 400 MHz δ: 11.19 (s, 1H), 8.46 (s, 2H), 6.82-7.43 (m, 9H), 5.61 (s, 2H), 4.65 (dd, 2H), 4.08 (brt, J=5.6 Hz, 2H), 3.88 (brs, 2H), 2.87 (t, J=5.6 Hz, 2H), 2.48 (s, 2H), 2.08 (t, J=4.8 Hz, 2H).

Example 59

Preparation of (±)-trans-2-dimethylamino-acetic acid-3-(5,6-dihydro-4H-pyrrolo[3,2,1-ij]quinolin-1-yl)-4-(1H-indol-3-yl)-2,5-dioxo-pyrrolidin-1-ylmethyl ester To a solution of (±)-trans-3-(5,6-Dihydro-4H-pyrrolo[3,2,1-ij]quinolin-1-yl)-1-hydroxymethyl-4-(1H-indol-3-yl)-pyrrolidine-2,5-dione (0.5 mmol) in tetrahydrofuran (8 mL) was added N,N-dimethylglycine (1.1 equivalents) followed by the addition of HBTU (1.5 equivalents) and DIPEA (N,N-diisopropylethylamine, 2.2 equivalents). The mixture was stirred at room temperature for 15 hours. The solvents were removed under reduced pressure and the residue was taken up in ethyl acetate and water (1:1, 15 mL). The organic layer was separated and dried to yield a residue.

The residue was purified by chromatography on a silica gel column eluted with ethyl acetate hexanes to yield (±)-trans-2-dimethylamino-acetic acid-3-(5,6-dihydro-4H-pyrrolo[3,2,1-ij]quinolin-1-yl)-4-(1H-indol-3-yl)-2,5-dioxo-pyrrolidin-1-yl methyl ester. $^1$H NMR (DMSO-$d_6$) 400 MHz δ: 11.10 (s, 1H), 6.82-7.41 (m, 9H), 5.70 (m, 2H), 4.62 (dd, 2H), 4.07 (brs, 2H), 3.23 (s, 2H), 2.87 (brs, 2H), 2.23 (s, 6H), 2.08 (brs, 2H).

Example 60

Preparation of (±)-trans-Isonicotinic acid-3-(5,6-dihydro-4H-pyrrolo[3,2,1-ij]quinolin-1-yl)-4-(1H-indol-3-yl)-2,5-dioxo-pyrrolidin-1-ylmethyl ester (±)-trans-Isonicotinic acid 3-(5,6-dihydro-4H-pyrrolo[3,2,1-ij]quinolin-1-yl)-4-(1H-indol-3-yl)-2,5-dioxo-pyrrolidin-1-ylmethyl ester was prepared as in Example 59 by replacing N,N-dimethylglycine with 4-carboxypyridine. $^1$H NMR (DMSO-$d_6$) 400 MHz δ: 11.19 (s, 1H), 8.83 (d, 2H), 7.83 (d, 2H), 6.83-7.42 (m, 9H), 5.88 (s, 2H), 4.65 (dd, 2H), 4.05 (brt, 2H), 2.86 (brs, 2H), 2.08 (brs, 2H).

Example 61

Preparation of 3-(5,6-dihydro-4H-pyrrolo[3,2,1-ij]quinolin-1-yl)-4-(1-methylindol-3-yl)-1-methyl pyrrole-2,5-dione and (±)-cis-3-(5,6-dihydro-4H-pyrrolo[3,2,1-ij]quinolin-1-yl)-4-(1-methylindol-3-yl)-1-methyl pyrrolidine-2,5-dione Step 1:
To a solution of 3-(5,6-dihydro-4H-pyrrolo[3,2,1-ij]quinolin-1-yl)-4-(1H-indol-3-yl) pyrrole-2,5-dione (100 mg, see Example 1) in anhydrous dimethylformamide (5 mL) was added potassium carbonate (0.5 g) and methyl iodide (0.1 mL). The mixture was stirred at room temperature for 48 hours then poured into ethyl acetate (100 mL), washed with water (100 mL), dried over anhydrous sodium sulfate and evaporated to give 3-(5,6-dihydro-4H-pyrrolo[3,2,1-ij]quinolin-1-yl)-4-(1-methylindol-3-yl)-1-methyl pyrrole-2,5-dione as a red solid (93 mg).

Step 2:
To a solution of 3-(5,6-dihydro-4H-pyrrolo[3,2,1-j]quinolin-1-yl)-4-(1-methylindol-3-yl)-1-methyl pyrrole-2,5-dione (93 mg) in methanol (5 mL) and ethylacetate (5 mL) was added 10% Pd—C (50 mg) and the mixture stirred at room temperature under 1 atmosphere of hydrogen for 48 hours. Toluene (50 mL) was added and the mixture again stirred at room temperature under 1 atmosphere of hydrogen for 2 hours. The mixture was then filtered through a pad of celite and evaporated to dryness to yield a residue. The residue was purified using silica gel chromatography eluting with 35-40% ethylacetate in hexanes to give (±)-cis-3-(5,6-dihydro-4H-pyrrolo[3,2,1-ij]quinolin-1-yl)-4-(1-methylindol-3-yl)-1-methyl pyrrolidine-2,5-dione as a pale yellow solid (53 mg). $^1$H NMR (CDCl$_3$) 400 MHz δ: 7.23 (s, 1H), 7.05-7.07 (m, 2H), 7.01 (d, 1H, J=7.2 Hz), 6.92-6.97 (m, 1H), 6.85 (t, 1H, J=7.2 Hz), 6.74 (d, 1H, J=6.8 Hz), 6.64 (d, 2H, J=6.4 Hz), 4.78 (m, 2H), 3.75-3.84 (m, 2H), 3.45 (s, 3H), 3.27 (s, 3H), 2.79 (t, 2H, J=5.6 Hz), 1.98 (m, 2H).

Example 62

Preparation of (±)-Trans-3-(5,6-dihydro-4H-pyrrolo[3,2,1-ij]quinolin-1-yl)-4-(1H-indol-3-yl) pyrrolidine-2,5-dione (±)-Trans-3-(5,6-dihydro-4H-pyrrolo[3,2,1-ij]quinolin-1-yl)-4-(1H-indol-3-yl) pyrrolidine-2,5-dione may be prepared by reacting 1H-indole and 3,4-dibromo-1-phenyl-pyrrole-2,5-dione in the presence of methyl magnesium bromide to yield 3-bromo-4-(1H-indol-3-yl)-1-phenyl-pyrrole-2,5-dione. The 3-bromo-4-(1H-indol-3-yl)-1-phenyl-pyrrole-2,5-dione is subsequently reacted with 5,6-dihydro-4H-pyrrolo[3,2,1-ij]quinoline and LiHMDS (lithium hexamethyldisilane) in toluene or (5,6-dihydro-4H-pyrrolo[3,2,1-ij]quinolin-1-yl)-boranediol and Pd(PPh$_3$)$_4$ (tetrakis(triphenylphosphine)palladium) to yield 3-(5,6-dihydro-4H-pyrrolo[3,2,1-ij]quinolin-1-yl)-4-(1H-indol-3-yl)-1-phenyl-pyrrole-2,5-dione, which is reduced and deprotected by treatment with Mg in methanol, as in Example 2 procedure C, followed by catalytic hydrogenation over palladium on carbon to yield (±)-trans-3-(5,6-dihydro-4H-pyrrolo[3,2,1-ij]quinolin-1-yl)-4-(1H-indol-3-yl) pyrrolidine-2,5-dione. Bnz is benzyl.

Example 63

Preparation of (±)-Trans-3-(5,6-dihydro-4H-pyrrolo[3,2,1-ij]quinolin-1-yl)-4-(1H-indol-3-yl) pyrrolidine-2,5-dione (±)-Trans-3-(5,6-dihydro-4H-pyrrolo[3,2,1-ij]quinolin-1-yl)-4-(1H-indol-3-yl) pyrrolidine-2,5-dione may be prepared by reacting 1-allyl-7-bromo-1H-indole with (COCl)$_2$ (oxalyl chloride) and sodium methoxide in a polar aprotic solvent such as dichloromethane to yield (1-allyl-7-bromo-1H-indol-3-yl)-oxo-acetic acid methyl ester, which is subsequently reacted with 2-(1H-indol-3-yl)-acetamide and tBuOK (potassium tert-butoxide) in THF to yield 3-(1-allyl-7-bromo-1H-indol-3-yl)-4-(1H-indol-3-yl)-pyrrole-2,5-dione. Reduction of the 3-(1-allyl-7-bromo-1H-indol-3-yl)-4-(1H-indol-3-yl)-pyrrole-2,5-dione by Mg in refluxing methanol, as in Example 2 procedure C, yields 3-(1-allyl-7-bromo-1H-indol-3-yl)-4-(1H-indol-3-yl)-pyrrolidine-2,5-dione, which is treated with 9-BBN (9-borabicyclo[3.3.1]nonane) and Pd(PPh$_3$)$_4$ (tetrakis(triphenylphosphine) palladium) to yield (±)-trans-3-(5,6-dihydro-4H-pyrrolo[3,2,1-ij]quinolin-1-yl)-4-(1H-indol-3-yl) pyrrolidine-2,5-dione.

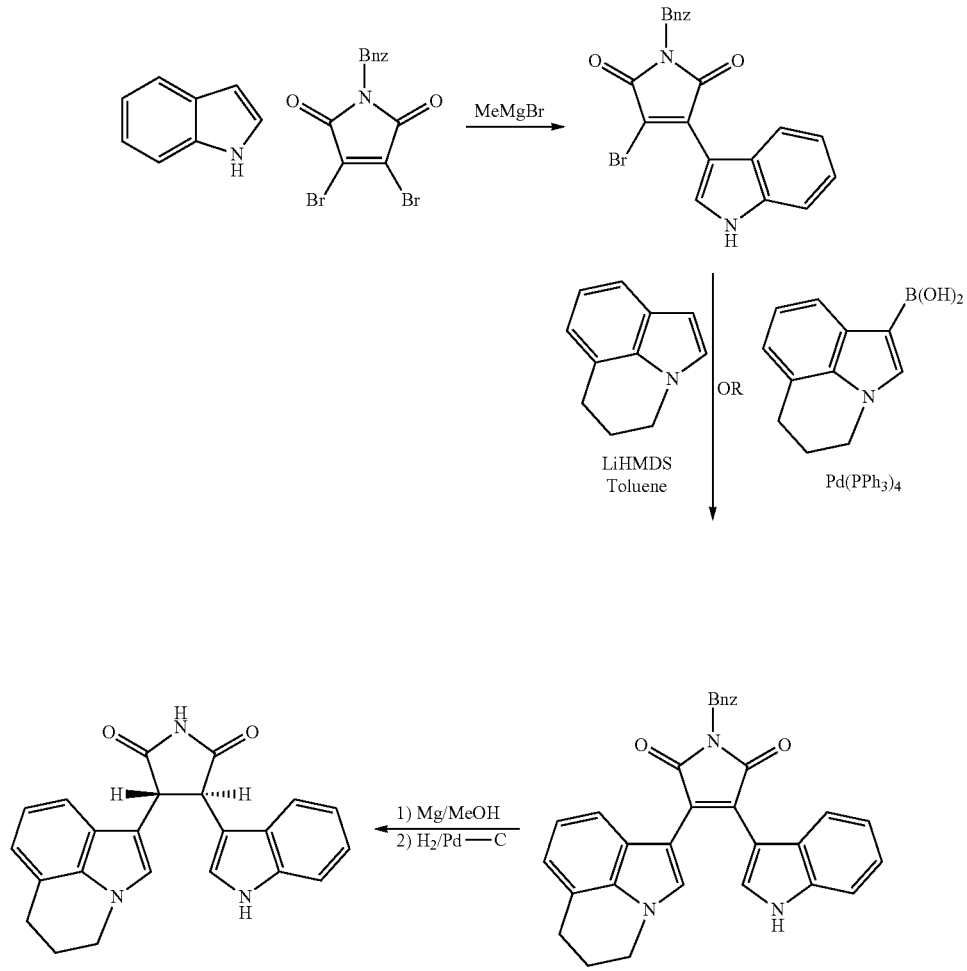

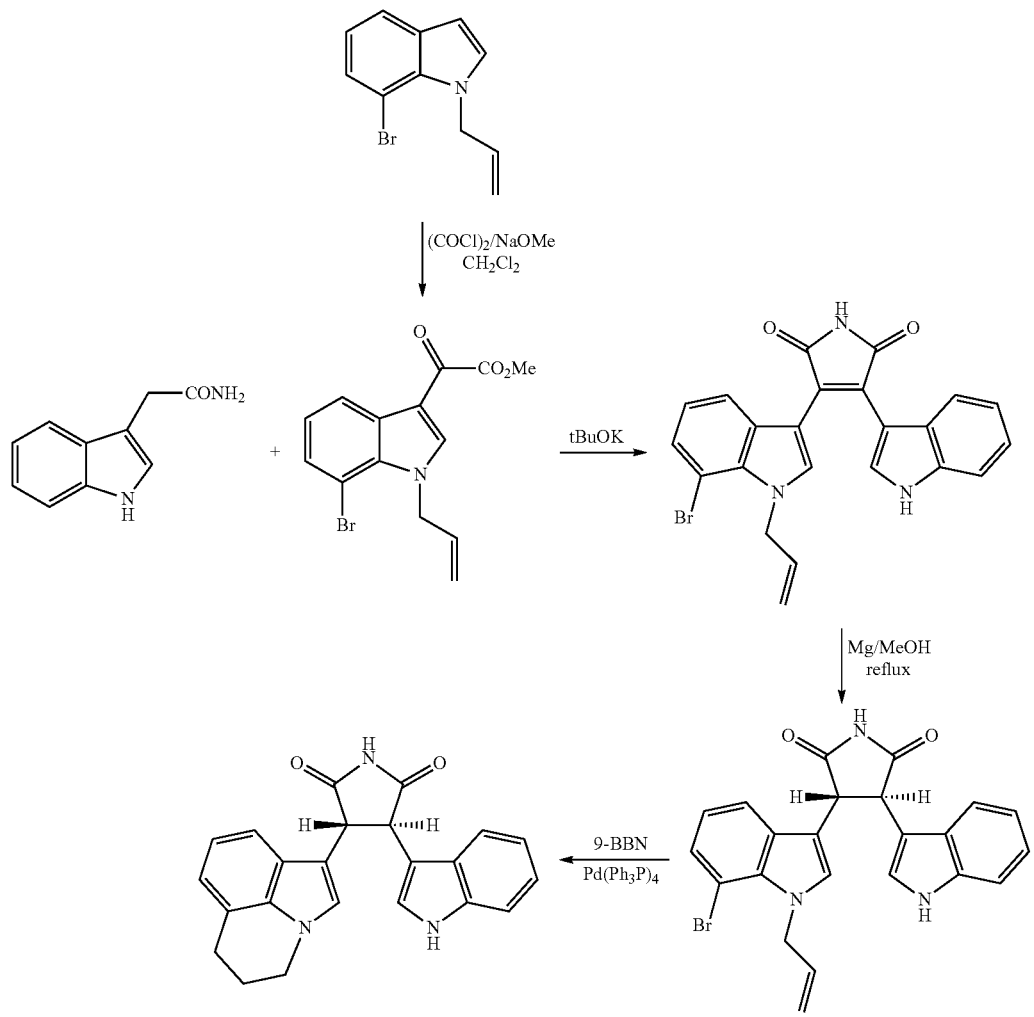

Example 64

Preparation of (±)-Cis-3-(5,6-dihydro-4H-pyrrolo[3,2,1-ij]quinolin-1-yl)-4-(1H-indol-3-yl) pyrrolidine-2,5-dione and (±)-Trans-3-(5,6-dihydro-4H-pyrrolo[3,2,1-ij]quinolin-1-yl)-4-(1H-indol-3-yl) pyrrolidine-2,5-dione The cis and trans isomers of 3-(5,6-dihydro-4H-pyrrolo[3,2,1-ij]quinolin-1-yl)-4-(1H-indol-3-yl) pyrrolidine-2,5-dione may be prepared beginning with the reaction of (1H-indol-3-yl)-oxo-acetic acid methyl ester and (5,6-dihydro-4H-pyrrolo[3,2,1-ij]quinolin-1-yl)-acetic acid methyl ester in the presence of a base such as LDA (lithium diisopropylamide) in a polar aprotic solvent such as THF to yield 2-(5,6-dihydro-4H-pyrrolo[3,2,1-ij]quinolin-1-yl)-3-(1H-indol-3-yl)-but-2-enedioic acid dimethyl ester. Alternatively, 2-(5,6-dihydro-4H-pyrrolo[3,2,1-ij]quinolin-1-yl)-3-(1H-indol-3-yl)-but-2-enedioic acid dimethyl ester may be prepared by reaction of (1H-indol-3-yl)-acetic acid methyl ester and (5,6-dihydro-4H-pyrrolo[3,2,1-ij]quinolin-1-yl)-oxo-acetic acid methyl ester in the presence of a base (e.g., LDA) in THF. The 2-(5,6-dihydro-4H-pyrrolo[3,2,1-ij]quinolin-1-yl)-3-(1H-indol-3-yl)-but-2-enedioic acid dimethyl ester is reduced by catalytic hydrogenation over a noble metal catalyst (e.g., Pd on charcoal) to give 2-(5,6-dihydro-4H-pyrrolo[3,2,1-ij]quinolin-1-yl)-3-(1H-indol-3-yl)-succinic acid dimethyl ester, which is reacted with benzylamine ($PhCH_2NH_2$) to yield a mixture of cis and trans 3-(5,6-dihydro-4H-pyrrolo[3,2,1-ij]quinolin-1-yl)-4-(1H-indol-3-yl)-1-phenyl-pyrrolidine-2,5-dione. The mixture of cis and trans isomers may be deprotected by catalytic hydrogenation over Pd on charcoal (Pd—C) to give rise to a mixture of cis and trans 3-(5,6-dihydro-4H-pyrrolo[3,2,1-ij]quinolin-1-yl)-4-(1H-indol-3-yl)-pyrrolidine-2,5-dione. The cis and trans isomers may be separated to give all four cis and trans isomers (e.g., by chromatography as in Examples 4 and 5). The deprotected mixture of cis and trans isomers may be treated with potassium tert-butoxide in tert-butanol (as in Example 3) or a mixture of THF and tert-butanol at 50° C. to yield a mixture with a predominance of the trans isomers. Alternatively, the 2-(5,6-dihydro-4H-pyrrolo[3,2,1-ij]quinolin-1-yl)-3-(1H-indol-3-yl)-succinic acid dimethyl ester can be reacted with ammonia in methanol at elevated temperatures to yield predominantly the cis isomers of 3-(5,6-dihydro-4H-pyrrolo[3,2,1-ij]quinolin-1-yl)-4-(1H-indol-3-yl)-pyrrolidine-2,5-dione, which may be isomerized to yield predominately the trans isomers of 3-(5,6-dihydro-4H-pyrrolo[3,2,1-ij]quinolin-1-yl)-4-(1H-indol-3-yl)-pyrrolidine-2,5-dione with potassium tert-butoxide in tert-butanol (as in Example 3) or a mixture of THF and tert-butanol at 50° C.

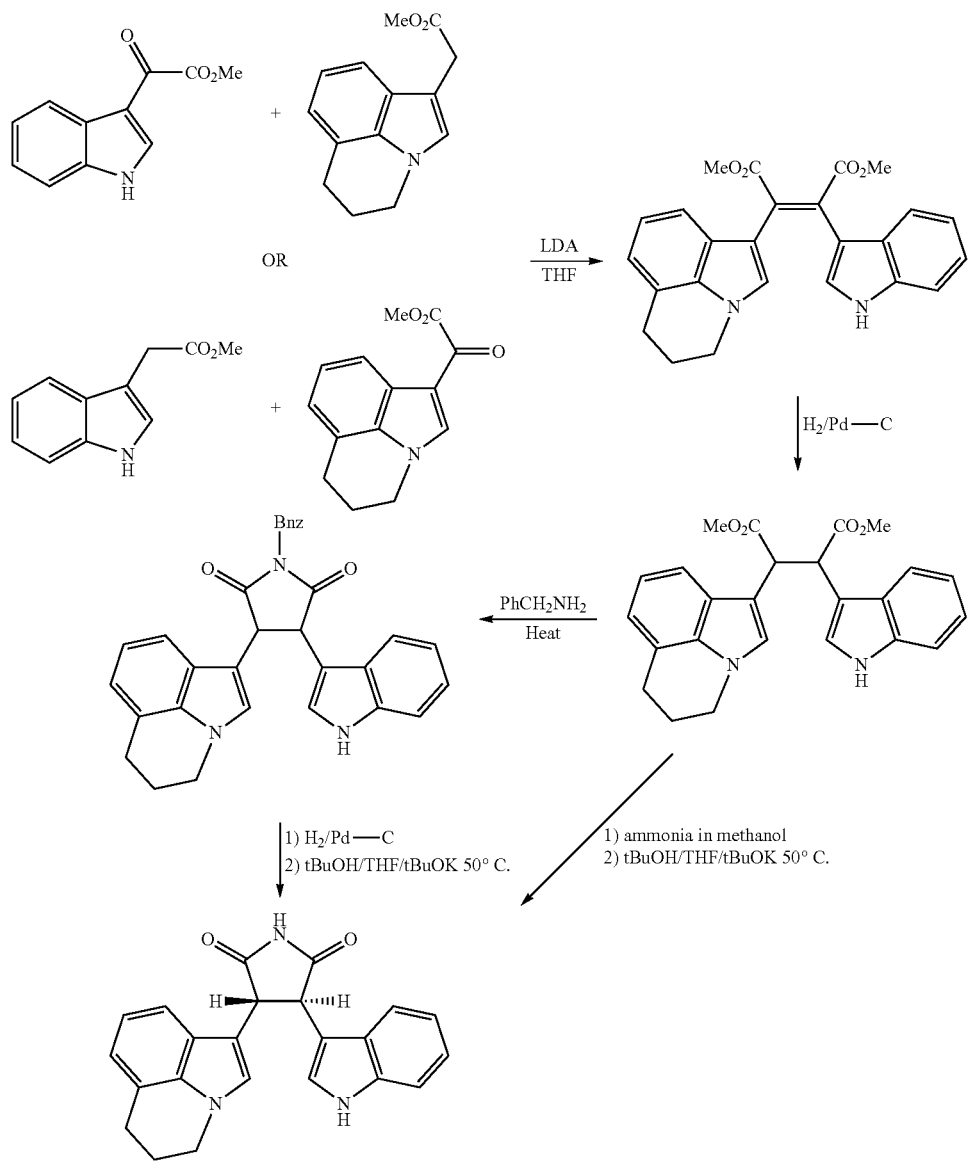

Example 65

Preparation of 3-(5,6-dihydro-4H-pyrrolo[3,2,1-ij] quinolin-1-yl)-4-(3-methoxyphenyl)-1H-pyrrole-2,5-dione To a mixture of 5,6-dihydro-4H-pyrrolo[3,2,1-ij]quinolin-1-yl) oxoacetic acid methyl ester (0.50 g, 2.05 mmol) and 2-(3-methoxyphenyl)acetamide (0.37 g, 2.26 mmol) in anhydrous tetrahydrofuran (5 mL) was added potassium tert-butoxide (1.0 M in tetrahydrofuran, 6.17 mL, 6.17 mmol) dropwise at 0° C. The mixture was stirred at 0° C. for 3 hours then concentrated hydrochloric acid (1.5 mL) was added at 0° C. The resulting mixture was stirred for 1 hour, diluted with ethyl acetate (150 mL), washed with water (2×50 mL), dried over anhydrous sodium sulfate and concentrated to give 0.91 g of an orange solid. The residue was purified by column chromatography eluting with 20-40% ethyl acetate in hexane to give 3-(5,6-dihydro-4H-pyrrolo[3,2,1-ij]quinolin-1-yl)-4-(3-methoxyphenyl)-1H-pyrrole-2,5-dione. Mp 99-101° C.; $^1$H NMR (CDCl$_3$) 400 MHz δ: 8.01 (s, 1H), 7.81 (bs, 1H), 7.20-7.25 (m, 1H), 7.06-7.08 (m, 2H), 6.85-6.91 (m, 2H), 7.25 (t, 1H), 6.13 (d, J=8.0 Hz, 1H), 4.24 (t, 2H), 3.66 (s, 3H), 2.97 (t, J=6.0 Hz, 2H), 2.22-2.26 (m, 2H).

Example 66

Preparation of 3-[4-(benzyloxy)phenyl]-4-(5,6-dihydro-4H-pyrrolo[3,2,1-ij]quinolin-1-yl)-1H-pyrrole-2,5-dione 3-[4-(benzyloxy)phenyl]-4-(5,6-dihydro-4H-pyrrolo[3,2,1-ij]quinolin-1-yl)-1H-pyrrole-2,5-dione was prepared according to Example 65, employing 2-(4-(benzyloxy)phenyl)acetamide in place of 2-(3-methoxyphenyl)acetamide. Mp 262-265° C.; $^1$H NMR (DMSO-d$_6$) 400 MHz δ: 10.96 (s. 1H), 8.01 (d, 1H), 7.33-7.45 (m, 7H), 6.99 (d, J=6.8 Hz, 2H), 6.83 (d, J=7.2 Hz, 1H), 6.63 (t, 1H), 6.09 (d, J=8.4 Hz, 1H), 5.13 (s, 2H), 4.27 (m, 2H), 2.92 (m, 2H), 2.15 (m, 2H).

Example 67

Preparation of 3-(5,6-dihydro-4H-pyrrolo[3,2,1-ij]quinolin-1-yl)-4-(4-fluorophenyl)-1H-pyrrole-2,5-dione 3-(5,6-dihydro-4H-pyrrolo[3,2,1-ij]quinolin-1-yl)-4-(4-fluorophenyl)-1H-pyrrole-2,5-dione was prepared according to Example 65, employing 2-(4-fluorophenyl)acetamide in place of 2-(3-methoxyphenyl)acetamide. Mp 234-235° C.; $^1$H NMR (DMSO-$d_6$) 400 MHz δ: 11.05 (s. 1H), 8.07 (d, 1H), 7.42-7.46 (m, 2H), 7.71-7.22 (m, 2H), 6.83 (d, J=7.2 Hz, 1H), 6.65-6.69 (m, 1H), 6.00 (d, J=8.0 Hz, 1H), 4.21 (s, 2H), 2.92 (bs, 2H), 2.15 (bs, 2H).

Example 68

Preparation of (±)-Trans-3-(5,6-dihydro-4H-pyrrolo[3,2,1-ij]quinolin-1-yl)-4-(3-methoxyphenyl)pyrrolidine-2,5-dione A mixture of 3-(5,6-dihydro-4H-pyrrolo[3,2,1-ij]quinolin-1-yl)-4-(3-methoxyphenyl)-1H-pyrrole-2,5-dione (0.73 g, 2.04 mmol), magnesium (0.89 g, 36.7 mmol) in anhydrous methanol was heated to reflux for 1.5 h. After cooling to room temperature, the light yellow solution was diluted with ethyl acetate (200 mL), washed with 1.0 M hydrochloric acid (2×50 mL), water (100 mL), dried over sodium sulfate and concentrated to provide a light brown solid. The residue was purified by column chromatography on silica gel eluting with 40-50% ethyl acetate in hexane to yield (±)-trans-3-(5,6-dihydro-4H-pyrrolo[3,2,1-ij]quinolin-1-yl)-4-(3-methoxyphenyl)pyrrolidine-2,5-dione as a light yellow solid. Mp 87-91° C.; $^1$H NMR (CDCl$_3$) 400 MHz δ: 8.73 (s. 1H), 7.25-7.30 (m, 1H), 7.14 (d, J=7.6 Hz, 1H), 6.93-7.01 (m, 3H), 6.77-6.86 (m, 3H), 4.36 (d, J=6.4 Hz, 1H), 4.24 (d, J=6.4 Hz, 1H), 4.18 (t J=5.5 Hz, 2H), 3.78 (s, 3H), 2.97 (t, J=5.6 Hz, 2H), 2.19-2.24 (m, 2H).

Example 69

Preparation of (±)-Trans-3-(5,6-dihydro-4H-pyrrolo[3,2,1-ij]quinolin-1-yl)-4-(3-hydroxyphenyl)pyrrolidine-2,5-dione To a solution of (±)-trans-3-(5,6-dihydro-4H-pyrrolo[3,2,1-ij]quinolin-1-yl)-4-(3-methoxyphenyl)pyrrolidine-2,5-dione in dichloromethane (10 mL) at −78° C. under an atmosphere of nitrogen was slowly added boron tribromide (1.0 M in dichloromethane) (5.2 mL). The resulting mixture was stirred at −78° C. for 30 minutes and at room temperature for 3 hours. The reaction mixture was cooled to −78° C. then quenched by the addition of methanol (5 mL). The mixture was allowed to warm to room temperature and maintained at room temperature for 30 minutes. The reaction mixture was diluted with dichloromethane (80 mL), washed with saturated aqueous sodium bicarbonate (15 mL), water (15 mL) and saturated sodium chloride (15 mL). The organic layer was dried over anhydrous sodium sulfate and concentrated to dryness. The residue was purified by flash chromatography on silica gel eluting with ethyl acetate:hexane:dichloromethane (5:5:1, v/v) to give (±)-trans-3-(5,6-dihydro-4H-pyrrolo[3,2,1-ij]quinolin-1-yl)-4-(3-hydroxyphenyl)pyrrolidine-2,5-dione as a brown solid (1.15 g, 63%); Mp 108-110° C. 1H NMR (CDCl3) 400 MHz δ: 8.69 (s, 1H), 7.18 (t, 1H, J=8.0 Hz), 7.12 (d, 1H, J=8.0 Hz), 6.99 (d, 1H, J=6.8 Hz), 6.97 (d, 1H, J=2.0 Hz), 6.93 (d, 1H, J=6.4 Hz), 6.76 (m, 1H), 6.69 (d, 1H, J=1.6 Hz), 5.67 (brs, 1H), 4.32 (d, 1H, J=6.0 Hz), 4.20 (d, 1H, J=6.0 Hz), 4.07 (t, 2H, J=5.6 Hz), 2.96 (t, 2H, J=6.0 Hz), 2.19 (m, 2H), LC/MS: 347.3 [M+H].

Example 70

Preparation of (±)-Trans-3-(5,6-dihydro-4H-pyrrolo[3,2,1-ij]quinolin-1-yl)-4-(4-fluorophenyl)pyrrolidine-2,5-dione 3-(5,6-dihydro-4H-pyrrolo[3,2,1-ij]quinolin-1-yl)-4-(4-fluorophenyl)-1H-pyrrole-2,5-dione prepared according to Example 67, was reduced by employing the method of Example 68 to yield (±)-trans-3-(5,6-dihydro-4H-pyrrolo[3,2,1-ij]quinolin-1-yl)-4-(4-fluorophenyl)pyrrolidine-2,5-dione 1-ij]quinolin-1-yl)-4-(4-fluorophenyl)-1H-pyrrole-2,5-dione. Mp 208-210° C.; $^1$H NMR (DMSO-$d_6$) 400 MHz δ: 11.52 (s. 1H), 7.40-7.43 (m, 2H), 7.32 (m, 1H), 7.13-7.17 (m, 3H), 6.82-6.89 (m, 2H), 4.53 (m, 1H), 4.36 (m, 1H), 4.09 (t, J=5.2 Hz, 2H), 2.89 (t, J=6.0 Hz, 2H), 2.09-2.11 (m, 2H).

Example 71

Preparation of (±)-Trans-3-[4-(benzyloxy)phenyl]-4-(5,6-dihydro-4H-pyrrolo[3,2,1-ij]quinolin-1-yl)pyrrolidine-2,5-dione 3-[4-(benzyloxy)phenyl]-4-(5,6-dihydro-4H-pyrrolo[3,2,1-ij]quinolin-1-yl)-1H-pyrrole-2,5-dione prepared according to Example 66, was reduced by employing the method of Example 68 to yield (±)-trans 3-[4-(benzyloxy)phenyl]-4-(5,6-dihydro-4H-pyrrolo[3,2,1-ij]quinolin-1-yl)pyrrolidine-2,5-dione. Mp 91-93° C.; $^1$H NMR (DMSO-$d_6$) 400 MHz δ: 11.47 (s. 1H), 7.25-7.43 (m, 8H), 7.15 (d, J=7.6 Hz, 2H), 6.82-6.96 (m, 4H), 5.07 (s, 2H), 4.45 (d, J=7.6 Hz, 1H), 4.24 (d, J=7.6 Hz, 1H), 4.07-4.10 (m, 2H), 2.87-2.90 (m, 2H), 2.09-2.10 (m, 2H).

Example 72

Preparation of (±)-Trans-3-(5,6-dihydro-4H-pyrrolo[3,2,1-ij]quinolin-1-yl)-4-(4-hydroxyphenyl)pyrrolidine-2,5-dione A mixture of (±)-trans-3-[4-(benzyloxy)phenyl]-4-(5,6-dihydro-4H-pyrrolo[3,2,1-ij]quinolin-1-yl)pyrrolidine-2,5-dione (0.2 g) and Pd/C (10% w/w, 0.076 g) was stirred under 1 atmosphere of hydrogen gas overnight. The catalyst was filtered off through a pad of celite and concentrated. The residue was purified by column chromatography on silica gel eluting with 30-40% ethyl acetate in hexane to provide (±)-trans-3-(5,6-dihydro-4H-pyrrolo[3,2,1-ij]quinolin-1-yl)-4-(4-hydroxyphenyl)pyrrolidine-2,5-dione 0.07 g as a light yellow solid. Mp 105-107° C.; $^1$H NMR (acetone-$d_6$) 400 MHz δ: 10.27 (s. 1H), 8.34 (s, 1H), 7.17-7.21 (m, 4H), 6.80-6.91 (m, 4H), 4.39 (d, J=7.0 Hz, 1H), 4.22 (d, J=7.0 Hz, 1H), 4.13 (d, J=5.6 Hz, 2H), 2.92 (d, J=5.2 Hz, 2H), 2.15-2.19 (m, 2H).

Example 73

Preparation of 7-[4-(1H-indol-3-yl)-2,5-dioxo-2,5-dihydro-1H-pyrrol-3-yl]-3,4-dihydro-1H-[1,4]diazepino[6,7,1-hi]indole-2-carboxylic acid benzyl ester Step 1

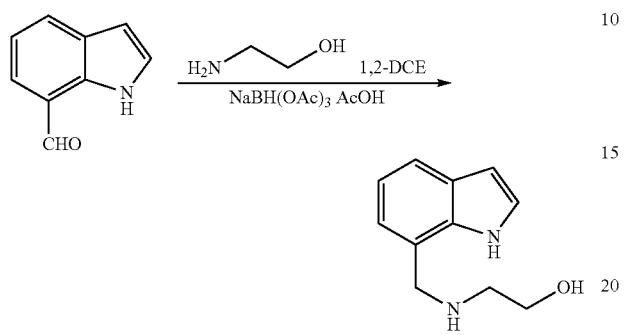

To a solution of 7-formyl indole (2.4 g, 16.6 mmol) in 1,2-dichloroethane (60 mL) was added aminoethanol (1.2 mL, 19.8 mmol) followed by glacial acetic acid (2.0 mL) and sodium triacetoxyborohydride (3.5 g, 16.6 mmol). The reaction mixture was allowed to stir at room temperature for 16 hours. The reaction mixture was quenched by addition of water (10 mL) and 1.0 M sodium hydroxide (10 mL). The organic layer was then separated and the aqueous layer extracted with 1,2-dichloroethane (40 mL). The combined organic extracts were washed with saturated sodium bicarbonate (2×30 mL), water (2×50 mL), dried over anhydrous sodium sulfate and evaporated to dryness. 2-[(1H-indol-7-ylmethyl)-amino]-ethanol (4.4 g) was obtained as an oil LCMS (M+H)=189.

Step 2

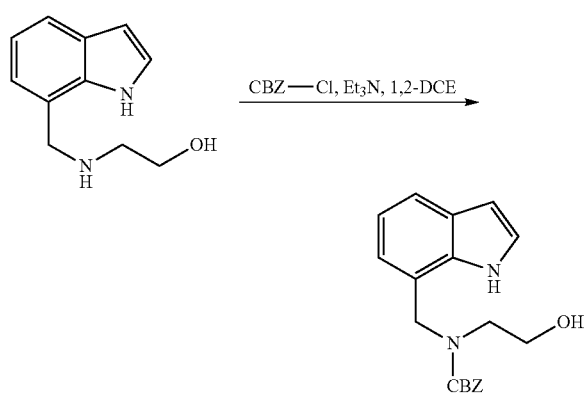

To a solution of 2-[(1H-indol-7-ylmethyl)-amino]-ethanol (4.4 g) in 1,2-dichloroethane (40 mL) was added triethylamine (4.85 mL, 34.6 mmol) followed by benzyl chloroformate (3.57 mL, 25.34 mmol). The mixture was allowed to stir at room temperature for 2 hours. The mixture was quenched by addition of water (20 mL), and 1.0 M sodium hydroxide (10 mL). The organic layer was separated and the aqueous layer extracted with 1,2-dichloroethane (20 mL). The combined organic extracts were washed with 1.0 M hydrochloric acid (20 mL), water (20 mL), dried over anhydrous sodium sulfate and evaporated to dryness. The residue was purified by silica gel chromatography, eluting with 20% ethyl acetate in hexanes to 40% ethyl acetate in hexanes to afford (2-hydroxy-ethyl)-(1H-indol-7-ylmethyl)-carbamic acid benzyl ester (2.79 g, 52% combined yield for two steps) as a colorless oil. $^1$H NMR (CDCl$_3$) 400 MHz δ: 9.97 (br s, 1H), 7.75-6.9 (m, 8H), 6.54 (br s, 1H), 5.21 (s, 2H), 4.9-4.6 (m, 3H), 3.85-3.57 (m, 2H), 3.55-3.23 (m, 3H); LCMS M+H=325.

Step 3

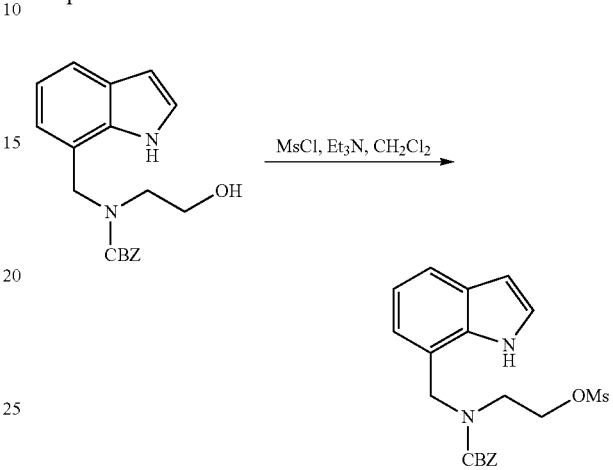

To a solution of (2-hydroxy-ethyl)-(1H-indol-7-ylmethyl)-carbamic acid benzyl ester (2.79 g, 8.61 mmol) in dichloromethane (50 mL) was added triethylamine (1.56 mL, 11.2 mmol). The mixture was cooled to 0° C. and methanesulfonyl chloride (0.74 mL, 9.47 mmol) added in a dropwise manner. The mixture was warmed to room temperature and allowed to stir for 2 hours. The mixture was then quenched with water (30 mL) and 1.0 M sodium hydroxide (10 mL). The organic layer was separated and the aqueous layer extracted with dichloromethane (20 mL). The combined extracts were washed with 1.0 M hydrochloric acid (20 mL), water (30 mL), dried over anhydrous sodium sulfate and evaporated to dryness. Methanesulfonic acid 2-[benzyloxycarbonyl-(1H-indol-7-ylmethyl)-amino]-ethyl ester (3.46 g) was obtained as an oil Step 4

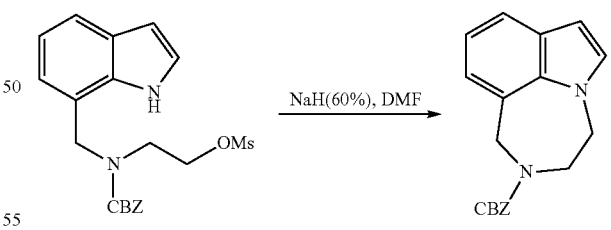

To a solution of methanesulfonic acid 2-[benzyloxycarbonyl-(1H-indol-7-ylmethyl)-amino]-ethyl ester (3.46 g, 8.61 mmol) in dimethylformamide (20 mL), which has been cooled to 0° C. was added sodium hydride (60%) in mineral oil. The reaction mixture was allowed to stir at 0° C. for 1 hour and then quenched by the addition of water (40 mL). The aqueous layer was extracted with ethyl acetate (4×20 mL). The combined organic extracts were washed with water (3×30 mL), dried over anhydrous sodium sulfate and evaporated to dryness. The residue was purified by silica gel chromatography, eluting with dichloromethane to afford 3,4-dihydro-1H-[1,4]diazepino[6,7,1-hi]indole-2-carboxylic acid benzyl ester (1.95 g, 74% combined yield for two steps) as a colorless oil. $^1$H NMR (CDCL$_3$) 400 MHz δ: 7.6-7.45 (m, 1H), 7.4-7.2 (m, 5H), 7.17-6.9 (m, 3H), 6.6-6.48 (m, 1H), 5.2-5.05 (m, 2H), 5.0-4.82 (m, 2H), 4.4-4.2 (m, 2H), 4.1-3.95 (m, 2H); LCMS (M+H)=307.

Step 5

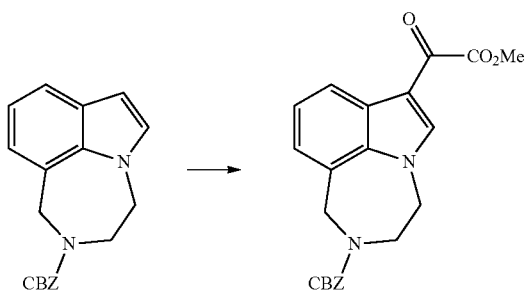

To a solution of 3,4-dihydro-1H-[1,4]diazepino[6,7,1-hi]indole-2-carboxylic acid benzyl ester (557 mg, 1.8 mmol), in anhydrous tetrahydrofuran (10 mL) at 0° C., was added oxalyl chloride (238 µl, 2.7 mmol) followed by a further portion of oxalyl chloride (340 µl, 3.85 mmol). The mixture was stirred at 0° C. until all the starting material has been consumed before being cooled to −78° C. Sodium methoxide in methanol (0.5M) (10 mL) was then added slowly and the mixture allowed to warm to room temperature. After 1 hour at room temperature the mixture was then diluted with ethyl acetate (200 mL) and washed with water (300 mL). The organic layer was dried over anhydrous sodium sulfate and evaporated to dryness. The residue was purified by silica gel chromatography, eluting with a ethyl acetate/hexanes (1:1) to afford 7-methoxyoxalyl-3,4-dihydro-1H-[1,4]diazepino[6,7,1-hi]indole-2-carboxylic acid benzyl ester as a pale yellow solid (481 mg, 67%). $^1$H NMR (CDCl$_3$) 400 MHz δ: 8.26-8.36 (m, 2H), 7.22-7.37 (m, 6H), 7.10 (dd, 1H, J=32.8 and 7.2 Hz), 5.11 (d, 2H, J=8.0 Hz), 4.94 (d, 2H, J=22.4 Hz), 4.41-4.48 (m, 2H), 4.01-4.05 (m, 2H), 3.93 (m, 3H).

Step 6

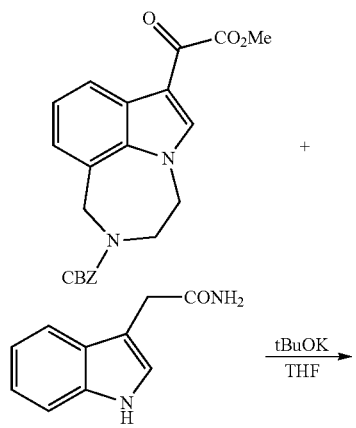

To a solution of 7-methoxyoxalyl-3,4-dihydro-1H-[1,4]diazepino[6,7,1-hi]indole-2-carboxylic acid benzyl ester (481 mg, 1.22 mmol) and indole-3-acetamide (234 mg, 1.34 mmol) in anhydrous tetrahydrofuran (14 mL) at 0° C. was added potassium t-butoxide (412 mg, 3.67 mmol). The mixture was stirred at 0° C. for 2 hours. Concentrated hydrochloric acid (5 mL) was then added and the mixture stirred for 2 hours at room temperature. The mixture was then diluted with ethyl acetate (300 mL), washed with water (500 mL), and the organic layer dried over anhydrous sodium sulfate. The residue was purified by silica gel chromatography, eluting with a ethyl acetate/hexanes (1:1) to afford 7-[4-(1H-indol-3-yl)-2,5-dioxo-2,5-dihydro-1H-pyrrol-3-yl]-3,4-dihydro-1H-[1,4]diazepino[6,7,1-hi]indole-2-carboxylic acid benzyl ester as a bright orange/red solid (1.2 g, 80%). $^1$H NMR (DMSO-d$_6$) 400 MHz δ: 11.66 (d, 1H, J=2.4 Hz), 10.94 (s, 1H), 7.69-7.75 (m, 2H), 7.19-7.38 (m, 6H), 6.98 (t, 1H, J=7.2 Hz), 6.73-6.89 (m, 3H), 6.60-6.66 (m, 2H), 4.90-5.08 (m, 2H), 4.50 (m, 2H), 3.95 (m, 2H).

Example 74

Preparation of (±)-Trans-7-[4-(1H-indol-3-yl)-2,5-dioxo-pyrrolidin-3-yl]-3,4-dihydro-1H-[1,4]diazepino[6,7,1-hi]indole-2-carboxylic acid benzyl ester

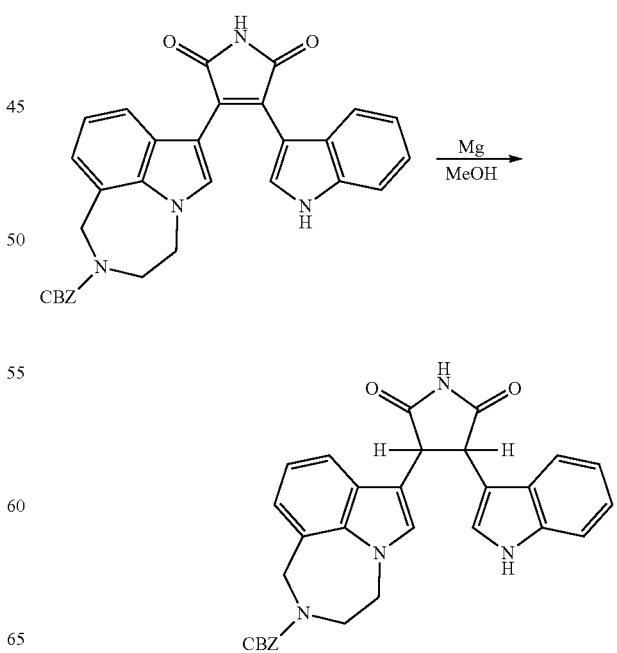

Magnesium turnings (195 mg, 8.0 mmol) were added to a solution of 7-[4-(1H-indol-3-yl)-2,5-dioxo-2,5-dihydro-1H-pyrrol-3-yl]-3,4-dihydro-1H-[1,4]diazepino[6,7,1-hi]indole-2-carboxylic acid benzyl ester (230 mg, 0.44 mmol) in anhydrous methanol (20 mL) and heated to reflux under an atmosphere of nitrogen for 1.5 hours. After cooling to room temperature the mixture was poured into ethyl acetate (200 mL) and washed with 1 M hydrochloric acid (100 mL). The organic layer was dried over anhydrous sodium sulfate and evaporated to dryness. The residue was then purified by silica gel chromatography using 50-60% ethyl acetate in hexanes to yield (±)-trans-7-[4-(1H-indol-3-yl)-2,5-dioxo-pyrrolidin-3-yl]-3,4-dihydro-1H-[1,4]diazepino[6,7,1-hi]indole-2-carboxylic acid benzyl ester as an off white solid (205 mg). $^{1}$H NMR (DMSO-$d_6$) 400 MHz δ: 11.56 (s, 1H), 11.03 (d, 1H, J=2 Hz), 7.21-7.43 (m, 10H), 7.09 (t, 1H, J=7.2 Hz), 6.92-7.00 (m, 2H), 6.82-6.89 (m, 3H), 5.04 (s, 2H), 4.87 (d, 2H, J=7.6 Hz), 4.54 (dd, 2H, J=7.6 and 28.8 Hz), 4.30 (m, 2H), 3.92 (m, 2H).

Example 75

Preparation of (±)-Trans-3-(1H-indol-3-yl)-4-(1,2,3,4-tetrahydro-[1,4]diazepino[6,7,1-hi]indol-7-yl)-pyrrolidine-2,5-dione

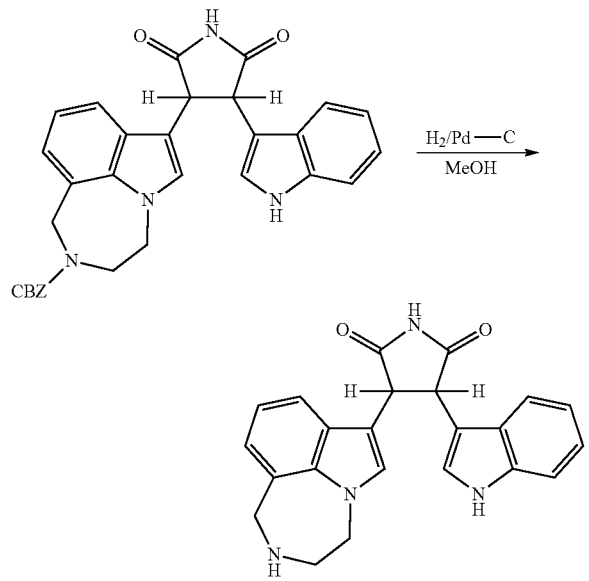

(±)-Trans-7-[4-(1H-indol-3-yl)-2,5-dioxo-pyrrolidin-3-yl]-3,4-dihydro-1H-[1,4]diazepino[6,7,1-hi]indole-2-carboxylic acid benzyl ester (161 mg, 0.31 mmol) and 10% palladium on carbon (100 mg) in anhydrous methanol (15 mL) were stirred under 1 atmosphere of hydrogen for 16 hours. The catalyst was then filtered through a bed of Celite and the filtrate evaporated to dryness to yield (±)-trans-3-(1H-indol-3-yl)-4-(1,2,3,4-tetrahydro-[1,4]diazepino[6,7,1-hi]indol-7-yl)-pyrrolidine-2,5-dione as an off white solid (95 mg). $^{1}$H NMR (DMSO-$d_6$) 400 MHz δ: 11.04 (d, 1H, J=1.6 Hz), 7.35-7.42 (m, 4H), 7.24 (dd, 1H, J=2.8 and 5.6 Hz), 7.09 (t, 1H, J=7.2 Hz), 6.89-6.98 (m, 3H), 4.52 (dd, 2H, J=7.2 and 24.8 Hz), 4.11 (s, 2H), 4.07-4.10 (m, 2H), 3.14-3.17 (m, 2H).

Example 76

Combination of c-Met Inhibitors with Sorafenib and Sunitinib for the Treatment of Various Anti-Proliferative Disorders and Cancer Materials and Methods Unless otherwise stated, the following materials and methods apply to the biological assays described herein.

Cell culture and reagents: NCI-H441, PC-3, MIA PaCa-2, HeLa, HT-29 and A549 cancer cell lines (American Type Culture Collection) were cultured in Dulbecco's modified Eagle's medium containing 10% fetal bovine serum, 100 units/mL penicillin, 100 g/mL streptomycin, and 2 mM L-glutamine.

Isobologram analysis: For each cell line and drug combination, the 72 hour $IC_{50}$ values were determined for each individual drug and in combination at the equipotent fixed ratio by MTT proliferation endpoint assay or by colony formation assay. For example, in the case of drugs A and B, where the $IC_{50}$ values are 1 M and 5 M, respectively, the equipotent ratio is 1:5. Therefore, a serial dilution of the highest combination concentration (8X to 0.125X, where X is the $IC_{50}$ ratio concentration) was used to generate a dose response curve. The degree of inhibition of cell proliferation in this assay relative to unexposed controls was designated the "effect", which ranged from 0.0 (no inhibition) to 1.0 (no cellular conversion of the MTT or MTS reagent, denoting complete cell death). Duplicate independent experiments were performed for each cell line/drug combination. Data were then analyzed by Calcusyn™ (Biosoft, Cambridge, UK) data analysis software.

Cell survival analysis. In some experiments, cell survival was determined by the 3-(4,5-dimethylthiazol-2-yl)-2,5-diphenyl tetrazolium bromide (MTT) assay. Briefly, cells were plated in a 96-well plate at 5-10,000 cells per well, cultured for 24 hours in complete growth medium, and then treated with various drugs and drug combinations for 72 hours. MTT was added to a final concentration of 0.5 mg/mL, and incubated for 1 hour, followed by assessment of cell viability using the microplate reader at 570 nm. Data were normalized to untreated controls and analyzed with Microsoft Excel.

Cell proliferation assay. Exponentially growing cells were seeded at 2,000 cells per well in 6-well plates and allowed to attach for 24 hours. Increasing concentrations of individual drugs and those in combination were then added to the media for another 24 hours. After 24 hours exposure, the drug was removed and fresh media was added for the next 14-21 days, allowing for colony formation. Cells were fixed and stained with GIEMSA (Gibco BRL). Colonies of greater than 50 cells were scored as survivors and the percentage of cell survival was plotted to determine the $IC_{50}$ values.

The studies described herein used a compound of Formula Va shown herein, namely, (−)-trans-3-(5,6-dihydro-4H-pyrrolo[3,2,1-ij]quinolin-1-yl)-4-(1H-indol-3-yl) pyrrolidine-2,5,-dione, a small molecule inhibitor of the c-Met receptor tyrosine kinase, in combination with the multi-targeted kinase inhibitor, sorafenib.

A panel of 64 human cancer cell lines encompassing a spectrum of genotypes and tissue origins were surveyed in 72 h MTS cytotoxicity assays across a wide range of compound concentrations. (−)-trans-3-(5,6-dihydro-4H-pyrrolo[3,2,1-ij]quinolin-1-yl)-4-(1H-indol-3-yl) pyrrolidine-2,5-dione and sorafenib were configured in checkerboard 3-fold dilutions for a 72-hr MTS assay.

In the instant example, two independent experiments were performed in parallel. The Chou algorithm was employed to calculate the Combination Index (CI) which is shown in Table 1.

TABLE 1

Criteria for Combination Index (CI)

| | |
|---|---|
| CI ≤ 0.3 | Strong Synergy |
| 0.3 < CI ≤ 0.85 | Synergy |
| 0.85 < CI ≤ 1.2 | Additive |
| 1.2 < CI ≤ 3.3 | Antagonism |
| CI ≥ 3.3 | Strong Antagonism |

Figures 2A, 2B:
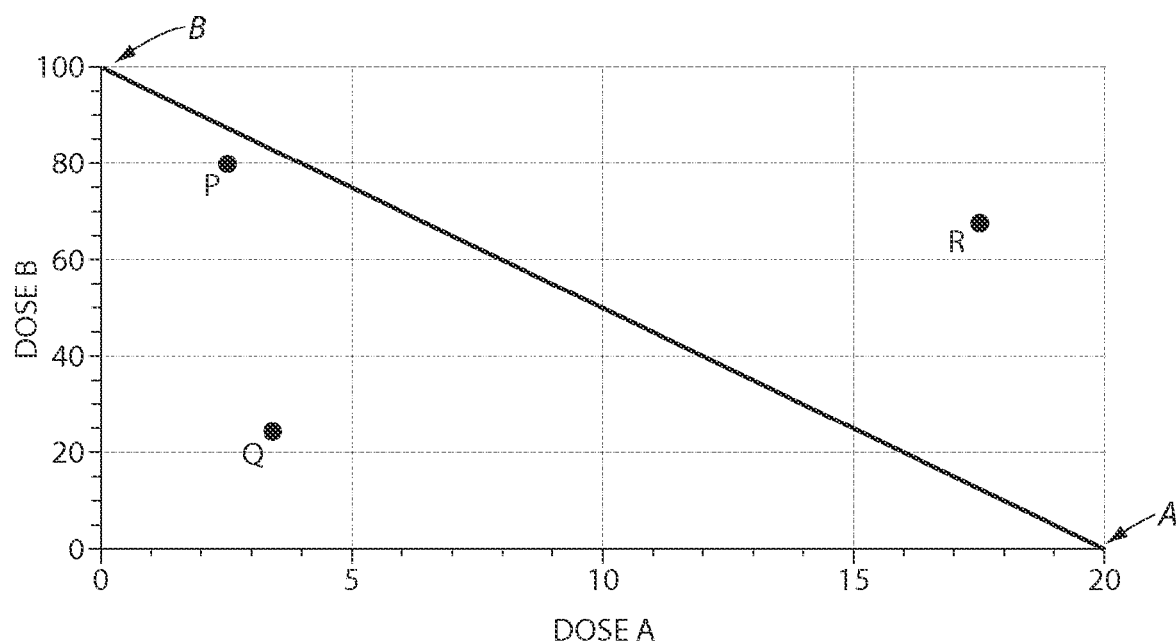
FIGS. 2A-B is a depiction of the computational tools used to assess pharmacologic synergy.

Combination indices were determined according to the method of Chou. {Chou, T.-C. 1991. The median-effect principle and the combination index for quantitation of synergism and antagonism, p. 61-102. In T.-C. Chou and D. C. Rideout (ed.), Synergism and antagonism in chemotherapy. Academic Press, San Diego, Calif}. FIG. 2, panel A, shows where $C_A^Q$ and $C_B^Q$ are the separate concentrations of drug A and B respectively that achieve the same effect as the mixture of drug A and of drug B. Isobologram analyses categorized drug combinations as synergistic, additive, or antagonistic. Specifically, FIG. 2, panel B, shows isobologram analyses for a particular effect (e.g., 50% of the maximum) in which the dose of drug A alone is A=20 and drug B alone is B=100. The straight line connecting these intercept points is the additivity line which, based on these potencies, should give the same effect. An actual dose pair such as point Q attains this effect with lesser quantities and is supra-additive or synergistic, while the dose pair denoted by point R means greater quantities are required and is therefore sub-additive. A point such as P that appears below the line would be simply additive.

The combination data of (–)-trans-3-(5,6-dihydro-4H-pyrrolo[3,2,1-ij]quinolin-1-yl)-4-(1H-indol-3-yl) pyrrolidine-2,5-dione with sorafenib are shown in Table 2 and the combination data with sunitinib are shown in Table 3. The compound (–)-trans-3-(5,6-dihydro-4H-pyrrolo[3,2,1-ij]quinolin-1-yl)-4-(1H-indol-3-yl) pyrrolidine-2,5,-dione is identified as "Agent A" in these tables. The identity and tissue origin of cancer cell lines are indicated. The results show that the combination (–)-trans-3-(5,6-dihydro-4H-pyrrolo[3,2,1-ij]quinolin-1-yl)-4-(1H-indol-3-yl) pyrrolidine-2,5-dione and sorafenib revealed synergistic cytotoxicity in 3 NSCLC cell lines (NCI-H522, NCI-H358, NCI-H460), MDA-MB-231 (breast), A375 (melanoma), the HCC1395 breast cancer line, the Caki-1 renal cell carcinoma, the HeLa cervical carcinoma cell line, and the A431 epidermoid carcinoma and showed additive cytotoxicity in 40 other cell lines including, but not limited to, the Colo205 and SW480 colon cancer lines, the NCI-H358 (NSCLC) cell line, and 3 hepatocellular carcinomas (JHH-4, PLC/PRF/5, SK-Hep-1). Table 2 shows the combination cytotoxicity of (–)-trans-3-(5,6-dihydro-4H-pyrrolo[3,2,1-ij]quinolin-1-yl)-4-(1H-indol-3-yl) pyrrolidine-2,5-dione and sorafenib in human cancer cell lines in which either additivity or synergism (supra-additivity) were observed. Table 3 shows the combination cytotoxicity of (–)-trans-3-(5,6-dihydro-4H-pyrrolo[3,2,1-ij]quinolin-1-yl)-4-(1H-indol-3-yl) pyrrolidine-2,5-dione and sunitinib in human cancer cell lines in which either additivity or synergism (supra-additivity) were observed.

TABLE 2

| Human Cancer Cell Line | Tissue of Origin | Combination Effect (Combination Index) |
|---|---|---|
| | | Agent A and sorafenib |
| MDA-MB-231 | Breast | Synergistic (0.61) |
| A375 | Melanoma | Synergistic (0.63) |
| NCI-H522 | Lung (NSCLC) | Synergistic (0.65) |
| HeLa | Cervix | Synergistic (0.66) |
| Caki-1 | Renal | Synergistic (0.71) |
| NCI-H358 | Lung (NSCLC) | Synergistic (0.74) |
| NCI-H460 | Lung (NSCLC) | Synergistic (0.80) |
| A431 | Skin | Synergistic (0.83) |
| HCC1395 | Breast | Synergistic (0.85) |
| NCI-H1299 | Lung (NSCLC) | Additive (0.87) |
| COLO205 | Colon | Additive (0.88) |
| HeLa S3 | Cervix | Additive (0.92) |
| SNU-16 | Stomach | Additive (0.93) |
| SW480 | Colon | Additive (0.94) |
| PLC/PRF/5 | Liver (hepatoma) | Additive (0.94) |
| NCI-H1993 | Lung (NSCLC) | Additive (0.96) |
| KATO III | Stomach | Additive (0.96) |
| SCH | Stomach | Additive (0.98) |
| A549 | Lung (NSCLC) | Additive (0.98) |
| MKN45 | Stomach | Additive (1.00) |
| K562 | Blood | Additive (1.01) |
| HCT116 | Colon | Additive (1.02) |
| SK-OV-3 | Ovary | Additive (1.02) |
| DMS 53 | Lung | Additive (1.05) |
| 786-O | Renal | Additive (1.05) |
| WI-26 VA4 | Lung | Additive (1.05) |
| MDA-MB-453 | Breast | Additive (1.06) |
| T98G | Brain | Additive (1.06) |
| MDA-MB-361 | Breast | Additive (1.07) |
| SK-Hep-1 | Liver (hepatoma) | Additive (1.07) |
| DU145 | Prostate | Additive (1.08) |
| NCI-H1581 | Lung (NSCLC) | Additive (1.09) |
| LN-18 | Brain | Additive (1.10) |
| DLD-1 | Colon | Additive (1.10) |
| WM-266-4 | Skin | Additive (1.11) |
| C-33A | Cervix | Additive (1.12) |
| LoVo | Intestine | Additive (1.12) |
| JHH-4 | Liver (hepatoma) | Additive (1.13) |
| AGS | Stomach | Additive (1.13) |
| G-361 | Skin | Additive (1.13) |
| ZR-75-1 | Breast | Additive (1.14) |
| MDA-MB-468 | Breast | Additive (1.16) |
| Mia PaCa-2 | Pancreas | Additive (1.17) |
| HLF | Liver (hepatoma) | Additive (1.17) |
| U937 | Blood | Additive (1.18) |
| SNU-398 | Liver (hepatoma) | Additive (1.18) |
| SW620 | Colon | Additive (1.19) |
| NCI-H69 | Lung | Additive (1.19) |
| SK-BR-3 | Breast | Additive (1.19) |

TABLE 3

| Human Cancer Cell Line | Tissue of Origin | Combination Effect (Combination Index) |
|---|---|---|
| | | Agent A & sunitinib |
| SCH | Stomach | Synergistic (0.78) |
| SNU-16 | Stomach | Synergistic (0.84) |
| KATO III | Stomach | Additive (1.02) |
| NCI-H1581 | Lung (NSCLC) | Additive (1.04) |
| DLD-1 | Colon | Additive (1.07) |
| LoVo | Intestine | Additive (1.08) |
| G-402 | Kidney | Additive (1.09) |
| K562 | blood | Additive (1.12) |
| MDA-MB-453 | Breast | Additive (1.12) |
| DMS 53 | Lung | Additive (1.15) |
| LN-18 | Brain | Additive (1.15) |
| U937 | blood | Additive (1.15) |
| HCT116 | Colon | Additive (1.16) |
| NCI H1703 | Lung (NSCLC) | Additive (1.19) |
| HeLa | Cervix | Additive (1.20) |
| SNU-5 | Stomach | Additive (1.20) |

The anti-proliferative effect of (−)-trans-3-(5,6-dihydro-4H-pyrrolo[3,2,1-ij]quinolin-1-yl)-4-(1H-indol-3-yl) pyrrolidine-2,5-dione and sorafenib on the NCI-H522 NSCLC cell line in vitro was also assessed. Cells were treated with increasing concentrations of (−)-trans-3-(5,6-dihydro-4H-pyrrolo[3,2,1-ij]quinolin-1-yl)-4-(1H-indol-3-yl) pyrrolidine-2,5-dione from 0.14 to 33 M and sorafenib from 0.015 to 100 M for 72 hr. Cell growth was assessed using a standard commercially available MTS reagent [3-(4,5-dimethylthiazol-2-yl)-5-(3 carboxymethoxyphenyl)-2-(4-sulfophenyl)-2H-tetrazolium, inner salt from Promega, Madison, Wis.]assay. An isobologram was plotted and the combination index was determined which showed the synergism of (−)-trans-3-(5,6-dihydro-4H-pyrrolo[3,2,1-ij]quinolin-1-yl)-4-(1H-indol-3-yl) pyrrolidine-2,5-dione and sorafenib.

Figure 3:
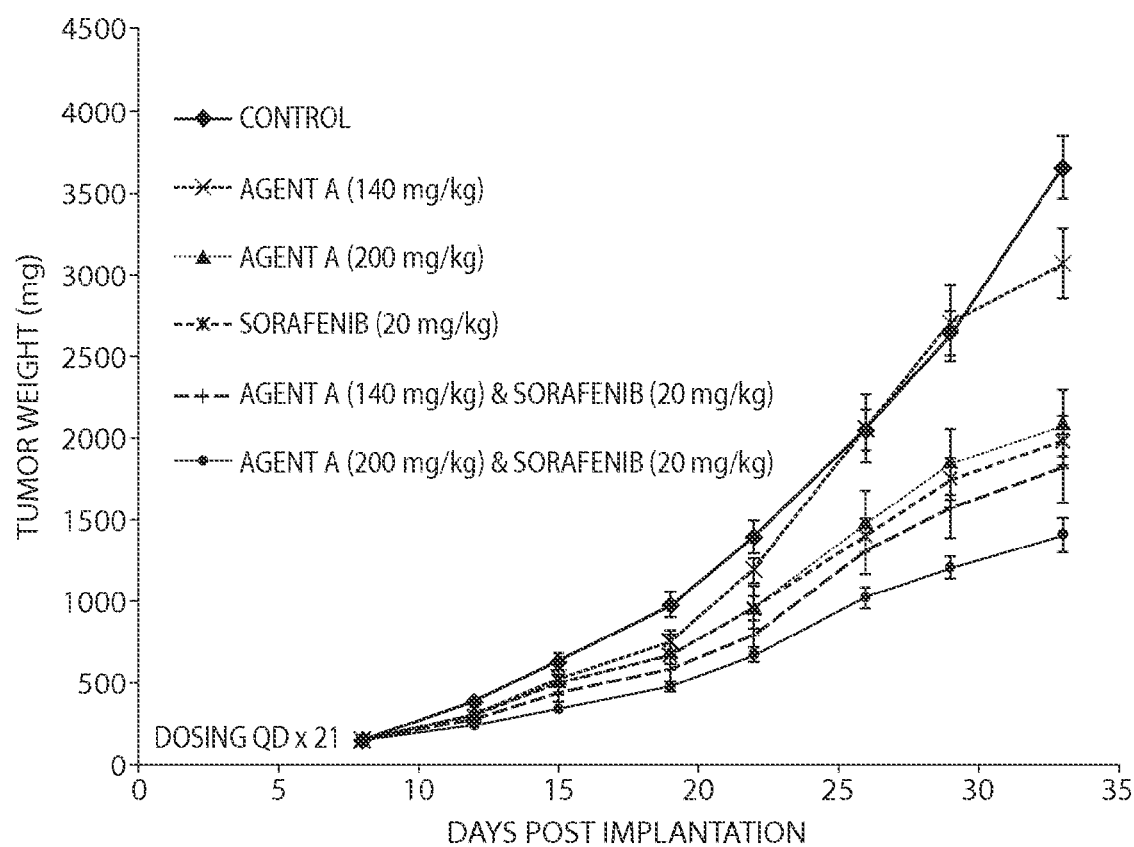
FIG. 3 is a graph showing the anti-proliferative effect of (−)-trans-3-(5,6-dihydro-4H-pyrrolo[3,2,1-ij]quinolin-1-yl)-4-(1H-indol-3-yl) pyrrolidine-2,5-dione and sorafenib in the NCI-H522 NSCLC xenograft model.

The in vivo anti-proliferative effect of (−)-trans-3-(5,6-dihydro-4H-pyrrolo[3,2,1-ij]quinolin-1-yl)-4-(1H-indol-3-yl) pyrrolidine-2,5-dione and sorafenib was also assessed. Female Ncr nu/nu mice with established subcutaneous NCI-H522 NSCLC tumors were treated by oral gavage with the indicated doses of (−)-trans-3-(5,6-dihydro-4H-pyrrolo[3,2,1-ij]quinolin-1-yl)-4-(1H-indol-3-yl) pyrrolidine-2,5-dione, sorafenib, both agents, or vehicle control for 21 days (days 8-29). All regimens were orally administered once daily for 21 days. Tumor sizes were evaluated periodically during treatment at the indicated days post-inoculation. FIG. 3 is a graphical representation of the combination treatment of (−)-trans-3-(5,6-dihydro-4H-pyrrolo[3,2,1-ij]quinolin-1-yl)-4-(1H-indol-3-yl) pyrrolidine-2,5-dione (shown as Agent A) and sorafenib demonstrating an effect in the NCI-H522 NSCLC xenograft model. These results are represented as the mean of tumor weight±SEM of 10 tumors during the treatment period. Both compounds were well-tolerated in all cohorts, and no adverse effects on body weight gain were observed, showing that these two agents are eminently combinable in vivo.

Taken together, these pre-clinical data demonstrate that the combinational therapy of c-Met inhibitors, such as (−)-trans-3-(5,6-dihydro-4H-pyrrolo[3,2,1-ij]quinolin-1-yl)-4-(1H-indol-3-yl) pyrrolidine-2,5-dione, and kinase inhibitors, such as sorafenib, shows highly encouraging anti-proliferative activity against a wide range of cancer cell lines, in vitro and in vivo.

Example 77

Combination of c-Met Inhibitors and Sorafenib for the Treatment of Microphthalmia Transcription Factor-Associated Tumors In clinical studies, monotherapy treatment with (−)-trans-3-(5,6-dihydro-4H-pyrrolo[3,2,1-ij]quinolin-1-yl)-4-(1H-indol-3-yl) pyrrolidine-2,5-dione has been well tolerated and has resulted in tumor responses and prolonged stable disease across broad ranges of tumors and doses. Indications with favorable clinical treatment include, MiT (Microphthalmia Transcription Factor)-associated tumors, non-small cell lung cancer and pancreatic adenocarcinoma. MiT tumors, which include clear cell sarcoma (CCS), alveolar soft part sarcoma (ASPS) and translocation-associated renal cell carcinoma (RCC), are linked biologically through a common chromosomal abnormality that is responsible for the over-expression of c-Met resulting in the development of these tumors. Similar clinical studies are directed to hepatocellular carcinoma (HCC) both for monotherapy treatment and combinational therapy with kinases inhibitors, such as sorafenib.

According to the National Cancer Institute, 21,370 new cases of HCC in the United States were projected in 2008, and 18,410 deaths were projected to be caused by the disease. In the U.S., the increasing incidence of HCC is related primarily to hepatitis C infection and cirrhosis. The first drug to be approved for patients with unresectable HCC was sorafenib. For patients who experience disease progression following sorafenib treatment or for those patients unable to tolerate sorafenib, no alternative therapy with proven clinical benefit is available. Thus, there is a high unmet medical need for novel treatment approaches in patients with advanced HCC for whom sorafenib treatment is not an option.

Over-expression of c-Met and its ligand, hepatocyte growth factor (HGF), is associated with poor prognoses in patients with HCC. When abnormally activated, c-Met plays multiple roles in aspects of human cancer, including cancer cell growth, survival, angiogenesis, invasion and metastasis. Scientific literature related to HCC provides evidence of the aberrant activation of the c-Met pathway. In addition, the dysregulation of c-Met and HGF has been shown to be common in this disease. Cell proliferation is a central mechanism responsible for liver cancer progression, and c-Met is believed to play an important role in this process.

In these clinical studies combining (−)-trans-3-(5,6-dihydro-4H-pyrrolo[3,2,1-ij]quinolin-1-yl)-4-(1H-indol-3-yl) pyrrolidine-2,5-dione and sorafenib, Patients are treated with (−)-trans-3-(5,6-dihydro-4H-pyrrolo[3,2,1-ij]quinolin-1-yl)-4-(1H-indol-3-yl) pyrrolidine-2,5-dione at 360 mg twice daily (bid) and sorafenib at 200 mg bid. Patients are also screened to valuate dynamic changes of hepatocyte growth factor (HGF), vascular endothelial growth factor (VEGF), and soluble c-Met in patients' peripheral blood that are associated with treatment of (−)-trans-3-(5,6-dihydro-4H-pyrrolo[3,2,1-ij]quinolin-1-yl)-4-(1H-indol-3-yl) pyrrolidine-2,5-dione and sorafenib. The results of the combinational treatment show additive and synergistic anti-proliferative effects when compared to monotherapy treatment with (−)-trans-3-(5,6-dihydro-4H-pyrrolo[3,2,1-ij]quinolin-1-yl)-4-(1H-indol-3-yl) pyrrolidine-2,5-dione.

Example 78

Combination of c-Met Inhibitors and Kinase Inhibitors for the Treatment of Various Anti-Proliferative Disorders and Cancer To complement Phase I data showing clinical response as a single agent, the potential synergy of (−)-trans-3-(5,6- dihydro-4H-pyrrolo[3,2,1-ij]quinolin-1-yl)-4-(1H-indol-3-yl) pyrrolidine-2,5-dione with two marketed tyrosine kinsase inhibitors (TKIs), sorafenib (also shown in Examples 76 and 77) and sunitinib was assessed. A panel of 64 human cancer cell lines encompassing a spectrum of genotypes and tissue origins were surveyed in 72 hour MTS cytotoxicity assays across a wide range of compound concentrations. Isobologram analyses categorized drug combinations as synergistic, additive, or antagonistic. The combination of (−)-trans-3-(5,6-dihydro-4H-pyrrolo[3,2,1-ij]quinolin-1-yl)-4-(1H-indol-3-yl) pyrrolidine-2,5-dione and sorafenib revealed synergistic cytotoxicity in 3 NSCLC cell lines (NCI-H522, NCI-H358, NCI-H460), MDA-MB-231 (breast), A375 (melanoma), the HCC1395 breast cancer line, the Caki-1 renal cell carcinoma, the HeLa cervical carcinoma cell line, and the A431 epidermoid carcinoma (see Example 89). Additivity was seen in 40 human cancer cell lines with the (−)-trans-3-(5,6-dihydro-4H-pyrrolo[3,2,1-ij]quinolin-1-yl)-4-(1H-indol-3-yl) pyrrolidine-2,5-dione/sorafenib combination including, but not limited to the Colo205 and SW480 colon cancer lines, the NCI-H358 (NSCLC) cell line, and 3 hepatocellular carcinomas (JHH-4, PLC/PRF/5, SK-Hep-1). This data may be informative in the design of combination therapy regimens for (−)-trans-3-(5,6-dihydro-4H-pyrrolo[3,2,1-ij]quinolin-1-yl)-4-(1H-indol-3-yl) pyrrolidine-2,5-dione.

In vitro combination cytotoxicity studies were conducted with (−)-trans-3-(5,6-dihydro-4H-pyrrolo[3,2,1-ij]quinolin-1-yl)-4-(1H-indol-3-yl) pyrrolidine-2,5-dione, in combination with sorafenib and sunitinib against a large panel of human cancer cell lines. A wide range of combination effects was observed, with a higher incidence of either synergistic or additive cytotoxic effects documented with (−)-trans-3-(5,6-dihydro-4H-pyrrolo[3,2,1-ij]quinolin-1-yl)-4-(1H-indol-3-yl) pyrrolidine-2,5-dione and sorafenib as compared with (−)-trans-3-(5,6-dihydro-4H-pyrrolo[3,2,1-ij]quinolin-1-yl)-4-(1H-indol-3-yl) pyrrolidine-2,5-dione and sunitinib. Interestingly, the two cell lines where (−)-trans-3-(5,6-dihydro-4H-pyrrolo[3,2,1-ij]quinolin-1-yl)-4-(1H-indol-3-yl) pyrrolidine-2,5-dione and sunitinib showed synergistic cytotoxicity are both known to express activated c-Met due to c-Met gene amplification (the SNU-16 gastric carcinoma and the SCH gastric choriocarcinoma cell line) (Table 3). The compound (−)-trans-3-(5,6-dihydro-4H-pyrrolo[3,2,1-ij]quinolin-1-yl)-4-(1H-indol-3-yl) pyrrolidine-2,5,-dione is identified as "Agent A" is this table. While the effects observed were not tissue-type specific, the cell lines exhibiting synergy with (−)-trans-3-(5,6-dihydro-4H-pyrrolo[3,2,1-ij]quinolin-1-yl)-4-(1H-indol-3-yl) pyrrolidine-2,5-dione and sorafenib included two c-Met expressing breast carcinoma cell lines (HCC1395 and MDA-MB-231) and three non-small cell lung carcinomas (NSCLC), NCI-H460, NCI-H358 and NCI-H522, all with documented c-Met expression or gene amplification. The NCI-H522 NSCLC cell line is known to exhibit c-Met gene amplification and secrete high levels of HGF, but it does not exhibit high constitutive levels of phospho-c-Met upon serum starvation. Nonetheless, (−)-trans-3-(5,6-dihydro-4H-pyrrolo[3,2,1-ij]quinolin-1-yl)-4-(1H-indol-3-yl) pyrrolidine-2,5-dione and sorafenib demonstrated augmented antitumor efficacy when co-administered orally in an athymic mouse xenograft model (FIG. 3). (−)-trans-3-(5,6-dihydro-4H-pyrrolo[3,2,1-ij]quinolin-1-yl)-4-(1H-indol-3-yl) pyrrolidine-2,5-dione and sorafenib showed additive cytotoxicity in 5 hepatocellular carcinomas (HCC) tested, a clinical indication for which sorafenib is currently approved. Recapitulation of the synergistic or additive cytotoxic effects of (−)-trans-3-(5,6-dihydro-4H-pyrrolo[3,2,1-ij]quinolin-1-yl)-4-(1H-indol-3-yl) pyrrolidine-2,5-dione and marketed TKIs in relevant animal models guide potential clinical development strategies for (−)-trans-3-(5,6-dihydro-4H-pyrrolo[3,2,1-ij]quinolin-1-yl)-4-(1H-indol-3-yl) pyrrolidine-2,5-dione, a novel, orally administered and well-tolerated anti-cancer drug candidate that demonstrates indications of clinical activity.

Figure 4:
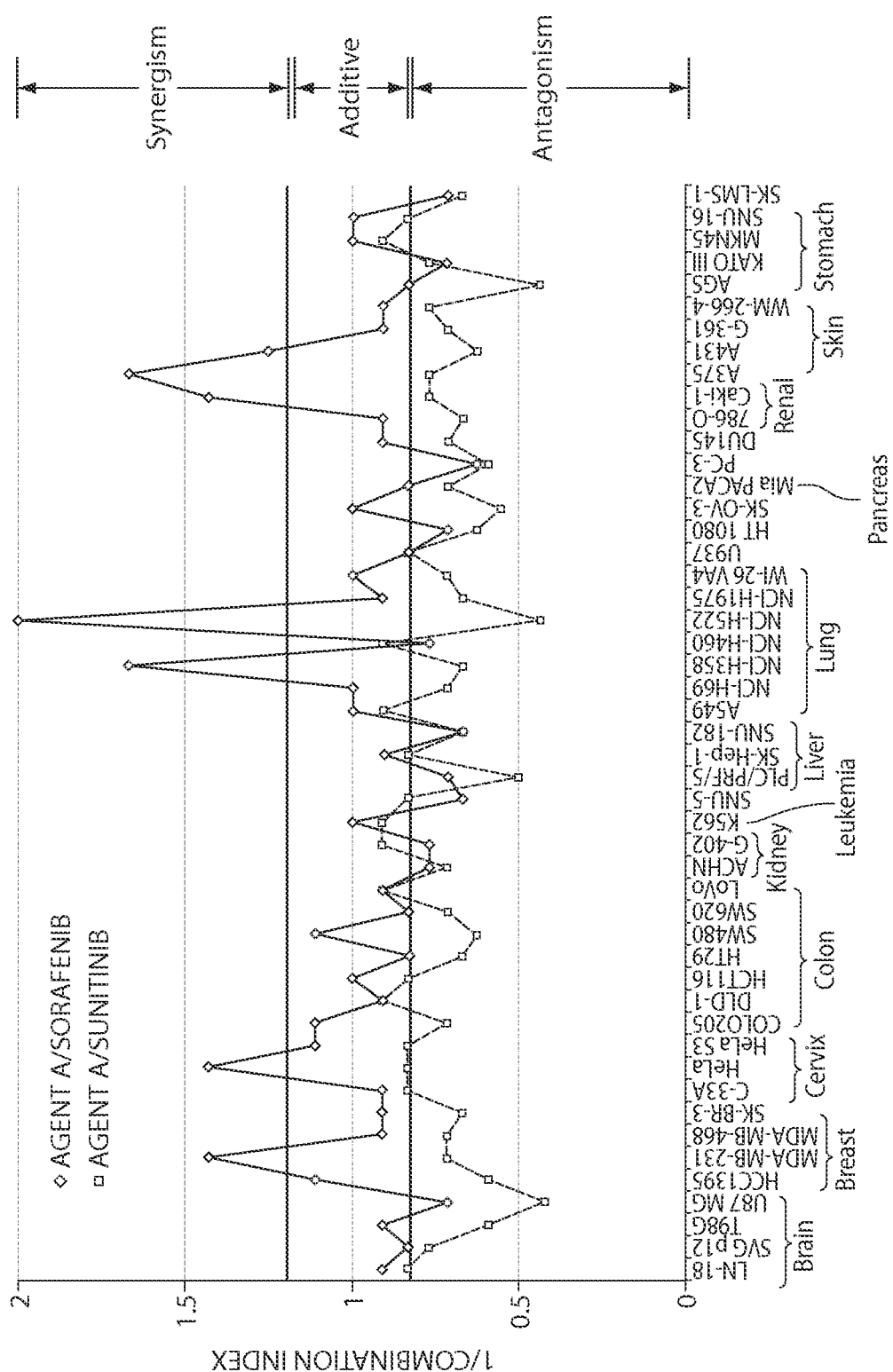
FIG. 4 is a graph showing the combinatorial anti-proliferative effect of (−)-trans-3-(5,6-dihydro-4H-pyrrolo[3,2,1-ij]quinolin-1-yl)-4-(1H-indol-3-yl) pyrrolidine-2,5-dione in combination with sorafenib and sunitinib on various cancer cell lines.
Figure 5:
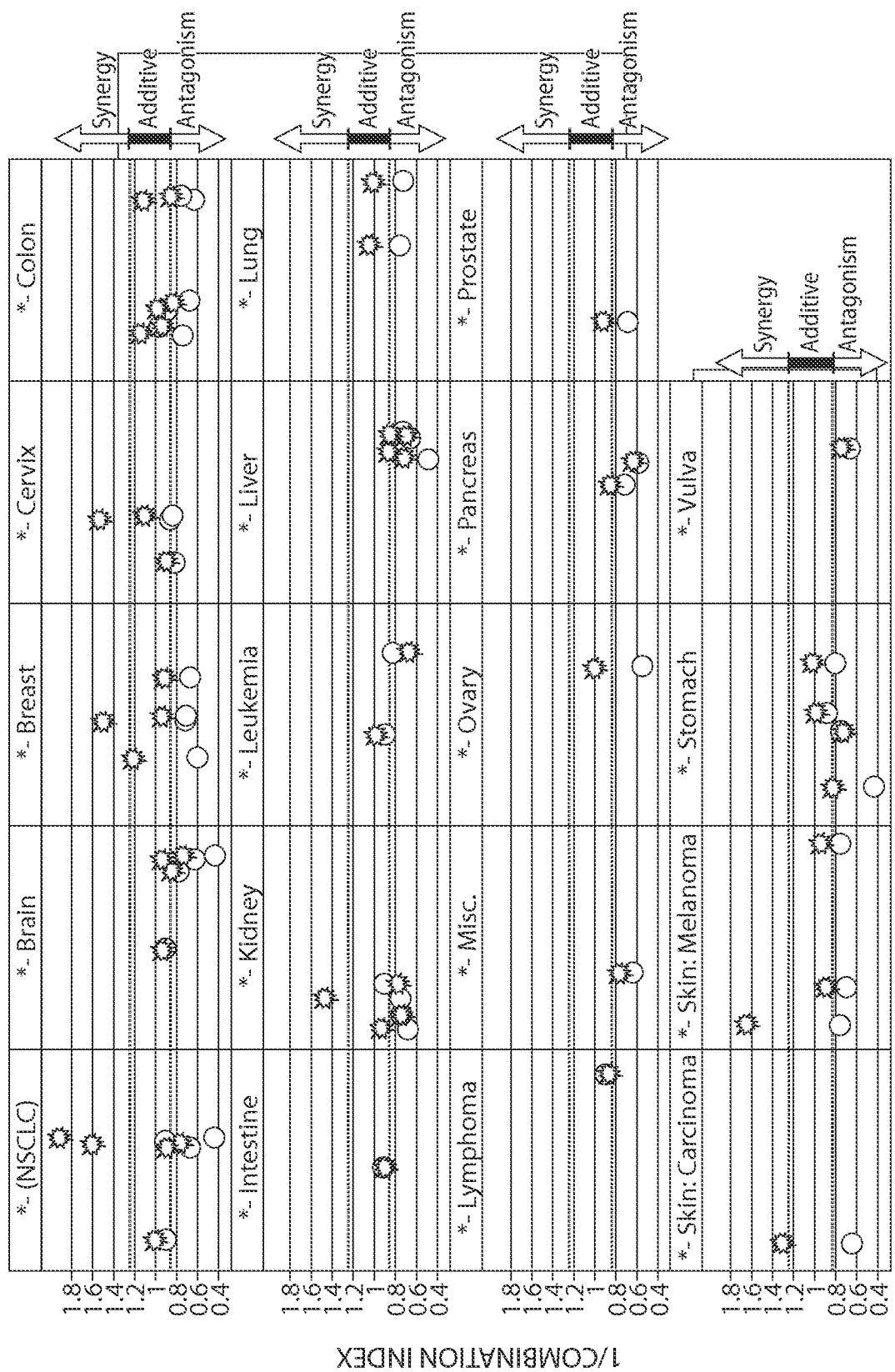
FIG. 5 is an illustration showing the combinatorial anti-proliferative effect of (−)-trans-3-(5,6-dihydro-4H-pyrrolo[3,2,1-ij]quinolin-1-yl)-4-(1H-indol-3-yl) pyrrolidine-2,5-dione in combination with sorafenib and sunitinib on various cancer cell lines.

The combination data of (−)-trans-3-(5,6-dihydro-4H-pyrrolo[3,2,1-ij]quinolin-1-yl)-4-(1H-indol-3-yl) pyrrolidine-2,5-dione (shown as Agent A in FIG. 4) with either sorafenib or sunitinib were expressed as 1/Combination Index as shown in FIGS. 4 and 5.

Example 79

Combination of c-Met Inhibitors and Erlotinib for the Treatment of Non-Small Cell Lung and Colon Cancer The effects of (−)-trans-3-(5,6-dihydro-4H-pyrrolo[3,2,1-ij]quinolin-1-yl)-4-(1H-indol-3-yl) pyrrolidine-2,5,-dione with erlotinib were tested in NCI-H441 non-small cell lung cancer cells (NSCLC). Erlotinib is an inhibitor of the epidermal growth factor receptor and is indicated for the treatment of patients with locally advanced or metastatic non-small cell lung cancer after failure of at least one prior chemotherapy regimen, and is indicated for the first-line treatment of patients with locally advanced, unresectable or metastatic pancreatic cancer. The $IC_{50}$ of erlotinib was predicted to be approximately 1 M, while the $IC_{50}$ of (−)-trans-3-(5,6-dihydro-4H-pyrrolo[3,2,1-ij]quinolin-1-yl)-4-(1H-indol-3-yl) pyrrolidine-2,5,-dione was predicted to be 300 nM for NCI-H441 NSCLC cells and therefore an (−)-trans-3-(5,6-dihydro-4H-pyrrolo[3,2,1-ij]quinolin-1-yl)-4-(1H-indol-3-yl) pyrrolidine-2,5,-dione:erlotinib ratio of 1:3 was used. A 1:33 (−)-trans-3-(5,6-dihydro-4H-pyrrolo[3,2,1-ij]quinolin-1-yl)-4-(1H-indol-3-yl) pyrrolidine-2,5,-dione:erlotinib was used for HT29 colon cancer cells. The CI ranged between 0.45-1 at the $ED_{50}$ for the NCI-H441 cell line as determined by independent experiments, and the CI was 0.72 for the Ht29 cell line (Table 4). The compound (−)-trans-3-(5,6-dihydro-4H-pyrrolo[3,2,1-ij]quinolin-1-yl)-4-(1H-indol-3-yl) pyrrolidine-2,5,-dione is identified as "Agent A" in this table. Median effect plots and isobolograms were performed for each experiment. This data demonstrates an additive to synergistic anti-proliferative effects of (−)-trans-3-(5,6-dihydro-4H-pyrrolo[3,2,1-ij]quinolin-1-yl)-4-(1H-indol-3-yl) pyrrolidine-2,5,-dione and erlotinib in both non-small cell lung cancer cells (NSCLC) and colon cancer cells.

TABLE 4

| Cell Lines and Agent(s) | Combination Index values at | | | $IC_{50}$ | r |
|---|---|---|---|---|---|
| | ED25 | ED50 | ED75 | | |
| NCI-H441 | | | | | |
| Agent A & Erlotinib (1:3) | 0.96 | 0.45 | 0.30 | 277 nM | 0.98 |
| Agent A | N/A | N/A | N/A | 1477 nM | 0.94 |
| Erlotinib | N/A | N/A | N/A | 3159 nM | 0.99 |
| NCI-H441 | | | | | |
| Agent A & Erlotinib (1:3) | 2.02 | 1.01 | 0.52 | 881 nM | 0.98 |
| Agent A | N/A | N/A | N/A | 3305 nM | 0.97 |
| Erlotinib | N/A | N/A | N/A | 3562 nM | 0.98 |

TABLE 4-continued

| Cell Lines and Agent(s) | Combination Index values at | | | IC$_{50}$ | r |
|---|---|---|---|---|---|
| | ED25 | ED50 | ED75 | | |
| HT29 | | | | | |
| Agent A & Erlotinib (1:33) | 1.03 | 0.72 | 0.51 | 117 nM | 0.96 |
| Agent A | N/A | N/A | N/A | 179 nM | 0.97 |
| Erlotinib | N/A | N/A | N/A | 56334 nM | 0.98 |

Figure 6:
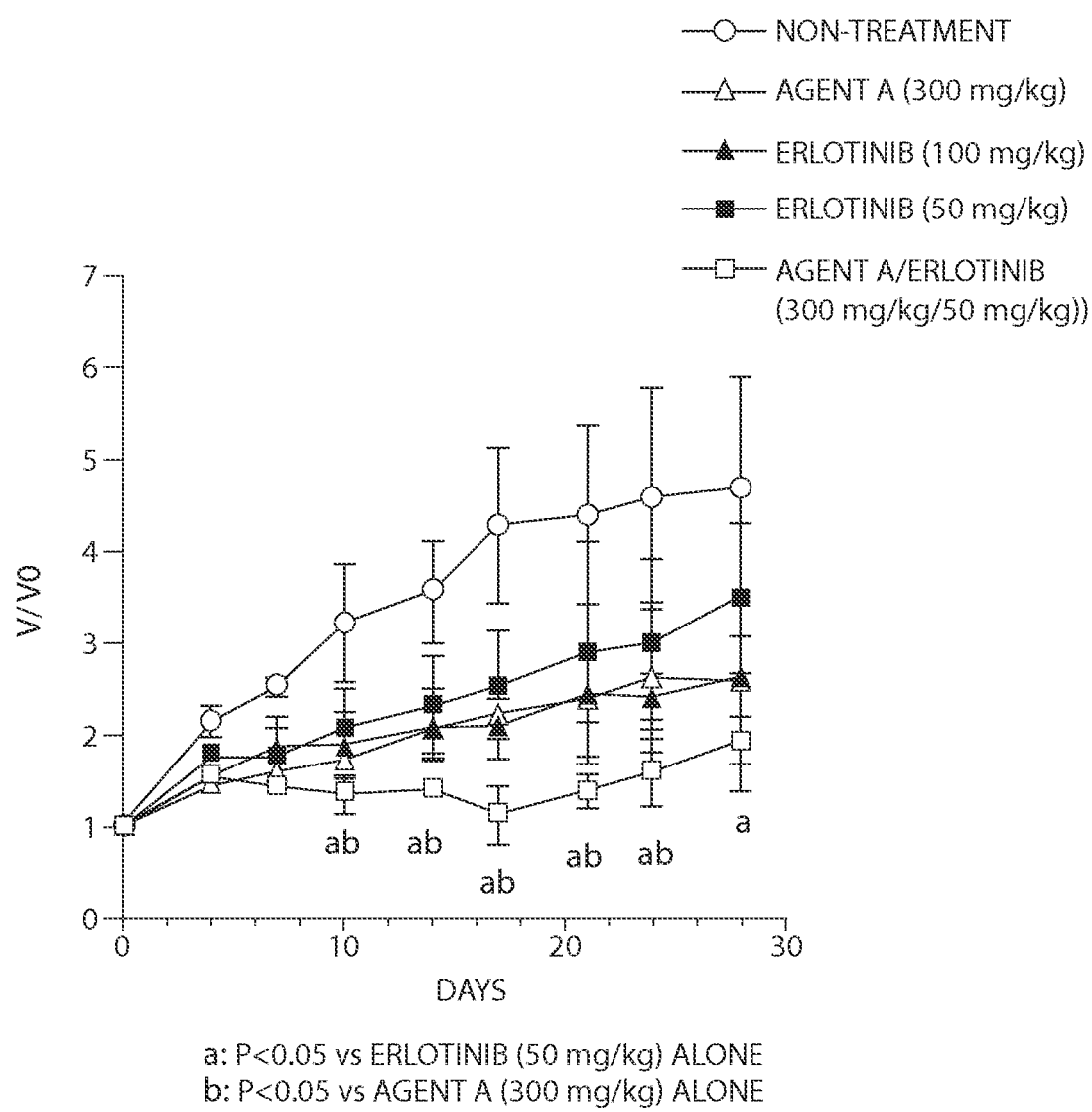
FIG. 6 is a graph showing the anti-proliferative effect of (−)-trans-3-(5,6-dihydro-4H-pyrrolo[3,2,1-ij]quinolin-1-yl)-4-(1H-indol-3-yl) pyrrolidine-2,5-dione in combination with erlotinib in a NCI-H441 human lung tumor xenograft model.

The effects of (−)-trans-3-(5,6-dihydro-4H-pyrrolo[3,2,1-ij]quinolin-1-yl)-4-(1H-indol-3-yl) pyrrolidine-2,5,-dione with erlotinib were tested in a NCI-H441 NSCLC human tumor xenograft model. (−)-trans-3-(5,6-dihydro-4H-pyrrolo[3,2,1-ij]quinolin-1-yl)-4-(1H-indol-3-yl) pyrrolidine-2,5,-dione was administered daily at 300 mg/kg orally, five days a week for four weeks (qd×5×4). Erlotinib was administered daily at 100 mg/kg or 50 mg/kg orally, five days a week for four weeks. As shown in Table 5 and FIG. 6, in all studies, the combination of (−)-trans-3-(5,6-dihydro-4H-pyrrolo[3,2,1-ij]quinolin-1-yl)-4-(1H-indol-3-yl) pyrrolidine-2,5,-dione with erlotinib showed improved anti-proliferative effects over monotherapy treatment and the data demonstrates at least an additive, and possibly synergistic, effect of (−)-trans-3-(5,6-dihydro-4H-pyrrolo[3,2,1-ij]quinolin-1-yl)-4-(1H-indol-3-yl) pyrrolidine-2,5,-dione with erlotinib in non-small cell lung cancer. The compound (−)-trans-3-(5,6-dihydro-4H-pyrrolo[3,2,1-ij]quinolin-1-yl)-4-(1H-indol-3-yl) pyrrolidine-2,5,-dione is identified as "Agent A" Table 5 and FIG. 6.

TABLE 5

| | Dosage (mg/kg) | Route | Schedule | T/C Min (on day) | BW loss (g) | Mortality |
|---|---|---|---|---|---|---|
| Non-Treatment | — | — | — | 1.00 | — | 0/5 |
| Agent A | 300 | p.o. | qd × 5 × 4 | 0.52 (17) | — | 0/5 |
| Erlotinib | 100 | p.o. | qd × 5 × 4 | 0.50 (17) | −1.0 (4) | 0/5 |
| | 50 | p.o. | qd × 5 × 4 | 0.59 (17) | −0.6 (4) | 0/5 |
| Agent A + Erlotinib | 300 100 | p.o. p.o. | Day 0-4, Day 7* Day 0-4, Day 7* | 0.43 (10) | −3.5 (7) | 0/5 |
| Agent A + Erlotinib | 300 50 | p.o. p.o. | qd × 5 × 4 qd × 5 × 4 | 0.27 (17) | −1.2 (10) | 0/5 |

*Drug administration after day 8 was terminated due to >10% body weight loss.

Example 80

Combination of c-Met Inhibitors and Gefitnib for the Treatment of Colon Cancer and Lung Cancer The effects of (−)-trans-3-(5,6-dihydro-4H-pyrrolo[3,2,1-ij]quinolin-1-yl)-4-(1H-indol-3-yl) pyrrolidine-2,5,-dione with gefitinib were tested in HT29 colon cancer cells. Gefitinib is an inhibitor of the EGF receptor. The IC$_{50}$ of gefitinib was predicted to be approximately 5 M, while the IC$_{50}$ of (−)-trans-3-(5,6-dihydro-4H-pyrrolo[3,2,1-ij]quinolin-1-yl)-4-(1H-indol-3-yl) pyrrolidine-2,5,-dione was predicted to be 150 nM for HT29 colon carcinoma cells, therefore an (−)-trans-3-(5,6-dihydro-4H-pyrrolo[3,2,1-ij]quinolin-1-yl)-4-(1H-indol-3-yl) pyrrolidine-2,5,-dione:gefitinib ratio of 1:33 was used. The CI was 1.27 at the ED$_{50}$ (Table 6). The compound (−)-trans-3-(5,6-dihydro-4H-pyrrolo[3,2,1-ij]quinolin-1-yl)-4-(1H-indol-3-yl) pyrrolidine-2,5,-dione is identified as "Agent A" is this table. Median effect plots and isobolograms were performed for each experiment. This data demonstrates at least an additive anti-proliferative effect of (−)-trans-3-(5,6-dihydro-4H-pyrrolo[3,2,1-ij]quinolin-1-yl)-4-(1H-indol-3-yl) pyrrolidine-2,5,-dione and gefitinib in colon cancer cells.

TABLE 6

| Agent(s) | Combination Parameters | | |
|---|---|---|---|
| | CI at ED$_{50}$ | IC$_{50}$ | r |
| Agent A & Gefitinib (1:33) | 1.27 | 99 nM | 0.97 |
| Agent A | N/A | 116 nM | 0.93 |
| Gefitinib | N/A | 7803 nM | 0.97 |

Figure 7:
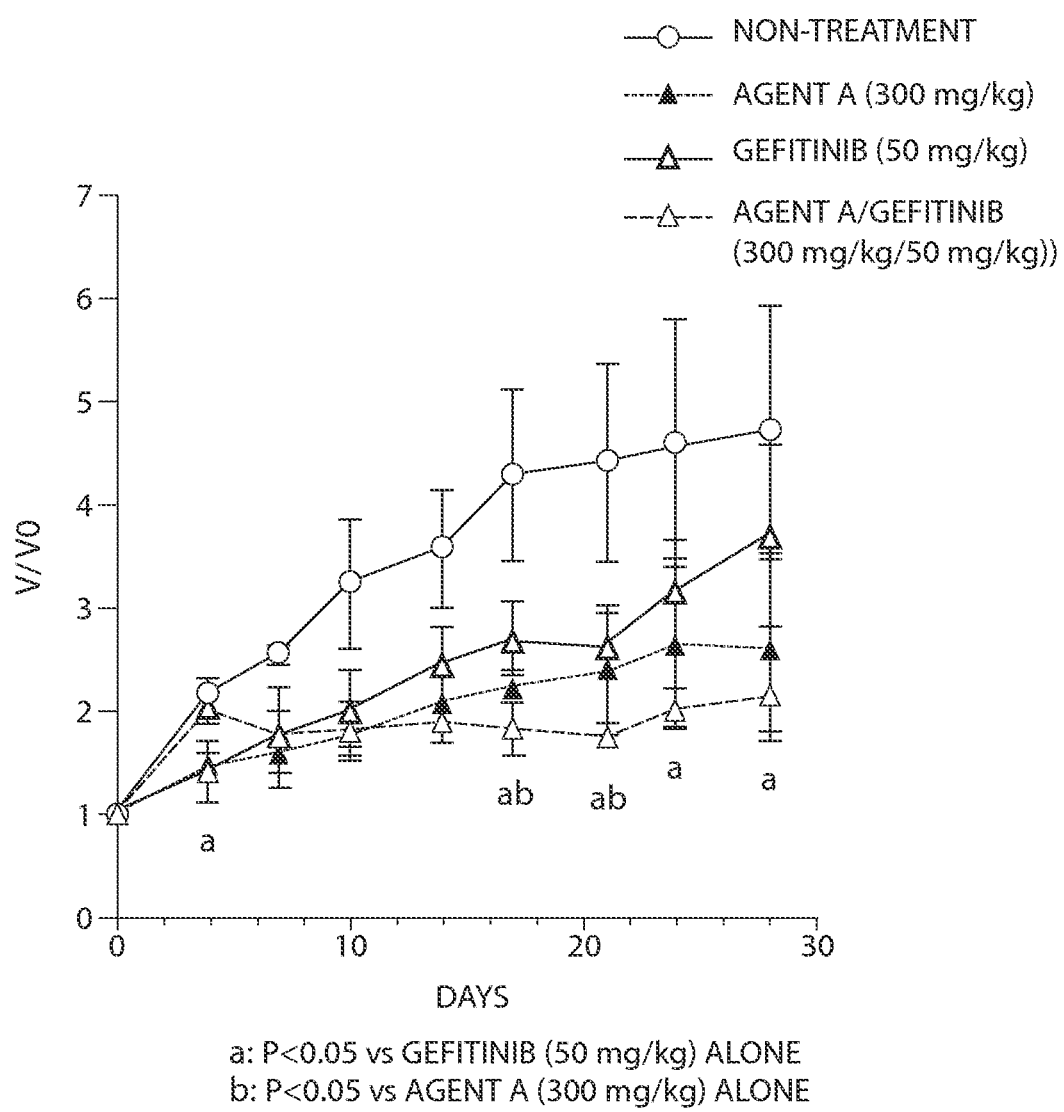
FIG. 7 is a graph showing the anti-proliferative effect of (−)-trans-3-(5,6-dihydro-4H-pyrrolo[3,2,1-ij]quinolin-1-yl)-4-(1H-indol-3-yl) pyrrolidine-2,5-dione in combination with gefitinib in a NCI-H441 human lung tumor xenograft model.

The effects of (−)-trans-3-(5,6-dihydro-4H-pyrrolo[3,2,1-ij]quinolin-1-yl)-4-(1H-indol-3-yl) pyrrolidine-2,5,-dione with gefitinib were tested in a NCI-H441 human lung tumor xenograft model. (−)-trans-3-(5,6-dihydro-4H-pyrrolo[3,2,1-ij]quinolin-1-yl)-4-(1H-indol-3-yl) pyrrolidine-2,5,-dione was administered daily at 300 mg/kg orally, five days a week for four weeks (qd×5×4). Gefitinib was administered daily at 50 mg/kg orally, five days a week for four weeks. As shown in Table 7 and FIG. 7, in all studies, the combination of (−)-trans-3-(5,6-dihydro-4H-pyrrolo[3,2,1-ij]quinolin-1-yl)-4-(1H-indol-3-yl) pyrrolidine-2,5,-dione with gefitinib showed improved anti-proliferative effects over monotherapy treatment and the data demonstrates at least an additive, and possibly synergistic, effect of (−)-trans-3-(5,6-dihydro-4H-pyrrolo[3,2,1-ij]quinolin-1-yl)-4-(1H-indol-3-yl) pyrrolidine-2,5,-dione with gefitinib in non-small cell lung cancer. The compound (−)-trans-3-(5,6-dihydro-4H-pyrrolo[3,2,1-ij]quinolin-1-yl)-4-(1H-indol-3-yl) pyrrolidine-2,5,-dione is identified as "Agent A" Table 7 and FIG. 7.

TABLE 7

| | Dosage (mg/kg) | Route | Schedule | T/C Min (on day) | BW loss (g) | Mortality |
|---|---|---|---|---|---|---|
| Non-Treatment | — | — | — | 1.00 | — | 0/5 |
| Agent A | 300 | p.o. | qd × 5 × 4 | 0.52 (17) | — | 0/5 |
| Gefitinib | 50 | p.o. | qd × 5 × 4 | 0.60 (21) | −0.5 (4) | 0/5 |
| Agent A + Gefitinib | 300 50 | p.o. p.o. | qd × 5 × 4 qd × 5 × 4 | 0.40 (21) | −1.0 (4) | 0/5 |

Example 81

Combination of c-Met Inhibitors and Carboplatin for the Treatment of Pancreatic Cancer The effects of (−)-trans-3-(5,6-dihydro-4H-pyrrolo[3,2,1-ij]quinolin-1-yl)-4-(1H-indol-3-yl) pyrrolidine-2,5,-dione with the DNA synthesis inhibitor carboplatin, was tested in MIA PaCa-2 pancreatic tumor cells. Carboplatin has been reported to be beneficial in both pancreatic and prostate cancer when combined with other therapeutic agents. The $IC_{50}$ of carboplatin was predicted to be approximately 25-50 M, while the $IC_{50}$ of (−)-trans-3-(5,6-dihydro-4H-pyrrolo[3,2,1-ij]quinolin-1-yl)-4-(1H-indol-3-yl) pyrrolidine-2,5,-dione was predicted to be 150 nM for MIA PaCa-2 cells. An (−)-trans-3-(5,6-dihydro-4H-pyrrolo[3,2,1-ij]quinolin-1-yl)-4-(1H-indol-3-yl) pyrrolidine-2,5,-dione:carboplatin ratio of 1:50 was used, unless otherwise indicated, due to the insolubility of carboplatin at higher concentrations. For MIA PaCa-2 cells the CI ranged between 1.09-1.45 at the 50% effective dose ($ED_{50}$) (Table 8). The compound (−)-trans-3-(5,6-dihydro-4H-pyrrolo[3,2,1-ij]quinolin-1-yl)-4-(1H-indol-3-yl) pyrrolidine-2,5,-dione is identified as "Agent A" is this table. Median effect plots and isobolograms were performed for each experiment. This data demonstrates at least an additive anti-proliferative effect of (−)-trans-3-(5,6-dihydro-4H-pyrrolo[3,2,1-ij]quinolin-1-yl)-4-(1H-indol-3-yl) pyrrolidine-2,5,-dione with carboplatin in pancreatic cancer cells. The mild variability observed in this drug combination is likely due to solubility issues of carboplatin at the higher dose ranges.

TABLE 8

| Agent(s) | Combination Parameters | | |
|---|---|---|---|
| | CI at $ED_{50}$ | $IC_{50}$ | R |
| Agent A & Carboplatin (1:80) | 1.09 | 0.11 μM | 0.99 |
| Agent A | N/A | 49 μM | 0.96 |
| Carboplatin | N/A | 0.12 μM | 0.97 |
| Agent A & Carboplatin (1:50) | 1.16 | 0.12 μM | 0.96 |
| Agent A | N/A | 0.13 μM | 0.96 |
| Carboplatin | N/A | 28 μM | 0.97 |
| Agent A & Carboplatin (1:50) | 1.45 | 0.18 μM | 0.98 |
| Agent A | N/A | 0.15 μM | 0.95 |
| Carboplatin | N/A | 37 μM | 0.98 |

Example 82

Combination of c-Met Inhibitors and Cisplatin for the Treatment of Pancreatic Cancer The effects of (−)-trans-3-(5,6-dihydro-4H-pyrrolo[3,2,1-ij]quinolin-1-yl)-4-(1H-indol-3-yl) pyrrolidine-2,5,-dione with the DNA synthesis inhibitor cisplatin were tested in MIA PaCa-2 pancreatic tumor cells. The $IC_{50}$ of cisplatin was predicted to be approximately 5-15 M, while the $IC_{50}$ of (−)-trans-3-(5,6-dihydro-4H-pyrrolo[3,2,1-ij]quinolin-1-yl)-4-(1H-indol-3-yl) pyrrolidine-2,5,-dione was predicted to be 150 nM for MIA PaCa-2 cells. An (−)-trans-3-(5,6-dihydro-4H-pyrrolo[3,2,1-ij]quinolin-1-yl)-4-(1H-indol-3-yl) pyrrolidine-2,5,-dione:cisplatin ratio of 1:50 was used unless otherwise indicated. For MIA PaCa-2 cells the CI ranged between 0.74-0.79 at the $ED_{50}$ (Table 9). The compound (−)-trans-3-(5,6-dihydro-4H-pyrrolo[3,2,1-ij]quinolin-1-yl)-4-(1H-indol-3-yl) pyrrolidine-2,5,-dione is identified as "Agent A" is this table. Median effect plots and isobolograms were performed for each experiment. This data demonstrates a synergistic anti-proliferative effect of (−)-trans-3-(5,6-dihydro-4H-pyrrolo[3,2,1-ij]quinolin-1-yl)-4-(1H-indol-3-yl) pyrrolidine-2,5,-dione and cisplatin in pancreatic cancer cells.

TABLE 9

| Agent(s) | Combination Parameters | | |
|---|---|---|---|
| | CI at $ED_{50}$ | $IC_{50}$ | r |
| Agent A & Cisplatin (1:50) | 0.79 | 0.040 μM | 0.95 |
| Agent A | N/A | 0.17 μM | 0.93 |
| Cisplatin | N/A | 3.79 μM | 0.97 |
| Agent A & Cisplatin (1:42) | 0.74 | 0.05 μM | 0.95 |
| Agent A | N/A | 0.29 μM | 0.95 |
| Cisplatin | N/A | 3.37 μM | 0.96 |

Example 83

Combination of c-Met Inhibitors and Various Chemotherapeutic Agents for the Treatment of Gastric Cancer The effects of (−)-trans-3-(5,6-dihydro-4H-pyrrolo[3,2,1-ij]quinolin-1-yl)-4-(1H-indol-3-yl) pyrrolidine-2,5,-dione with 5-FU, TS-1, Capecitabine, and cisplatin (CDDP) were tested in MKN-45 human gastric tumor xenograft model (FIG. 11-14). (−)-trans-3-(5,6-dihydro-4H-pyrrolo[3,2,1-ij]quinolin-1-yl)-4-(1H-indol-3-yl) pyrrolidine-2,5,-dione was administered daily at 300 mg/kg orally, five days a week for two weeks (qd×5×2). 5-FU was administered daily at 10 mg/kg intravenously, five days a week for two weeks. TS-1 was administered daily at 10 mg/kg orally, five days a week for two weeks. Capecitabine was administered daily at 360 mg/kg orally, five days a week for two weeks. CDDP was administered weekly at 5 mg/kg intravenously for two weeks. As shown in Table 10, in all studies, the combination of (−)-trans-3-(5,6-dihydro-4H-pyrrolo[3,2,1-ij]quinolin-1-yl)-4-(1H-indol-3-yl) pyrrolidine-2,5,-dione with these compounds showed improved anti-proliferative effects over monotherapy treatment and the data demonstrates at least and additive anti-proliferative effect of (−)-trans-3-(5,6-dihydro-4H-pyrrolo[3,2,1-ij]quinolin-1-yl)-4-(1H-indol-3-yl) pyrrolidine-2,5,-dione with 5-FU, TS-1, Capecitabine, and cisplatin in gastric cancer.

TABLE 10

| | Dosage (mg/kg) | Route | Schedule | T/C Min (on day) | BW loss (g) | Mortality |
|---|---|---|---|---|---|---|
| Non-Treatment | — | — | — | 1.00 | −2.3 (21) | — |
| Agent A | 300 | p.o. | qd × 5 × 2 | 0.50 (4) | −1.7 (21) | 0/5 |
| 5-FU | 10 | i.v. | qd × 5 × 2 | 0.63 (14) | −3.4 (21) | 0/5 |
| TS-1 | 10 | p.o. | qd × 5 × 2 | 0.45 (10) | −3.6 (14) | 1/5 |

TABLE 10-continued

|  | Dosage (mg/kg) | Route | Schedule | T/C Min (on day) | BW loss (g) | Mortality |
|---|---|---|---|---|---|---|
| Capecitabine | 360 | p.o. | qd × 5 × 2 | 0.42 (14) | −1.4 (21) | 0/5 |
| Cisplatin (CDDP) | 5 | i.v. | Weekly × 2 | 0.55 (10) | −2.0 (14) | 0/5 |
| Agent A + | 300 | p.o. | qd × 5 × 2 | 0.31 (14) | −0.9 (10) | 0/5 |
| 5-FU | 10 | i.v. | qd × 5 × 2 | | | |
| Agent A + | 300 | p.o. | qd × 5 × 2 | 0.29 (14) | −1.3 (21) | 0/5 |
| TS-1 | 10 | p.o | qd × 5 × 2 | | | |
| Agent A + | 300 | p.o. | qd × 5 × 2 | 0.29 (14) | −1.2 (4) | 0/5 |
| Capecitabine | 360 | p.o. | qd × 5 × 2 | | | |
| Agent A + | 300 | p.o. | qd × 5 × 2 | 0.43 (14) | −2.0 (10) | 0/5 |
| Cisplatin | 5 | i.v. | weekly × 2 | | | |

Example 84

Combination of c-Met Inhibitors and Imatinib for the Treatment of Colon Cancer

The effects of (−)-trans-3-(5,6-dihydro-4H-pyrrolo[3,2,1-ij]quinolin-1-yl)-4-(1H-indol-3-yl) pyrrolidine-2,5,-dione with imatinib (Gleevec) were tested in HT29 colon cancer cells. Imatinib is an inhibitor of the the Abelson proto-oncogene, c-kit, and PDGF-R (platelet-derived growth factor receptor) and is indicated for the treatment of chronic myelogenous leukemia (CML), gastrointestinal stromal tumors (GISTs) and a number of other malignancies. The $IC_{50}$ of imatinib was predicted to be approximately 10 μM, while the $IC_{50}$ of (−)-trans-3-(5,6-dihydro-4H-pyrrolo[3,2,1-ij]quinolin-1-yl)-4-(1H-indol-3-yl) pyrrolidine-2,5,-dione was predicted to be 150 nM for HT29 cells, therefore an (−)-trans-3-(5,6-dihydro-4H-pyrrolo[3,2,1-ij]quinolin-1-yl)-4-(1H-indol-3-yl) pyrrolidine-2,5,-dione:imatinib ratio of 1:66 was used. The CI was 1.22 at the $ED_{50}$ (Table 11). The compound (−)-trans-3-(5,6-dihydro-4H-pyrrolo[3,2,1-ij]quinolin-1-yl)-4-(1H-indol-3-yl) pyrrolidine-2,5,-dione is identified as "Agent A" is this table. Median effect plots and isobolograms were performed for each experiment. This data demonstrates a nearly additive anti-proliferative effect (a CI of 1.22 nearly meeting the criterion of a CI=1.2) of (−)-trans-3-(5,6-dihydro-4H-pyrrolo[3,2,1-ij]quinolin-1-yl)-4-(1H-indol-3-yl) pyrrolidine-2,5,-dione and imatinib in colon cancer cells.

TABLE 11

| Agent(s) | Combination Parameters | | |
|---|---|---|---|
| | CI at $ED_{50}$ | $IC_{50}$ | r |
| Agent A & Imatinib (1:66) | 1.22 | 70 nM | 0.98 |
| Agent A | N/A | 118 nM | 0.96 |
| Imatinib | N/A | 7374 nM | 0.99 |

Example 85

Combination of c-Met Inhibitors and Gemcitabine for the Treatment of Pancreatic Cancer c-Met was first discovered in the 1980s as an activated oncogene (Cooper, C. S. et al. (1984). Nature 311, 29-33) and is the prototype member of a sub-family of RTKs, including Ron, that are structurally distinct from other RTK families. c-Met is the only known high-affinity receptor for hepatocyte growth factor (HGF), also known as scatter factor (Birchmeier, C. et al. (2003). Nat Rev Mol Cell Biol 4, 915-925). In vitro and in vivo experiments have shown that this receptor-growth factor pair is involved in multiple physiologic cellular responses including embryogenesis, cell proliferation, survival, differentiation, motility, and invasion (Birchmeier, C. et al. (2003). Nat Rev Mol Cell Biol 4, 915-925). Subsequently, HGF and/or c-Met have been found to be frequently over-expressed in many types of human solid tumors, including sarcomas and carcinomas, and in their associated metastases where the degree of c-Met expression often correlates with poor patient prognosis (Birchmeier, C. et al. (2003). Nat Rev Mol Cell Biol 4, 915-925). Activating c-Met mutations have been described in both sporadic and inherited forms of human renal papillary carcinomas (Danilkovitch-Miagkova, A., and Zbar, B. (2002). J Clin Invest 109, 863-867), while genomic amplification of met has been found associated with gastric carcinoma (Nakajima, M. et al. Cancer 85, 1894-1902). Ectopic HGF and/or c-Met overexpression can drive tumorigenesis and metastasis in both human xenograft tumor bearing mice and transgenic mouse models (Takayama, H. et al. (1997). Proc Natl Acad Sci USA 94, 701-706). Taken together, these data provide compelling evidence for the functional relevance of c-Met activated networks in tumorigenesis and metastatic progression, thus c-Met is an attractive cancer therapeutic target.

(−)-trans-3-(5,6-dihydro-4H-pyrrolo[3,2,1-ij]quinolin-1-yl)-4-(1H-indol-3-yl) pyrrolidine-2,5,-dione has been shown to inhibit c-Met activity in biochemical assays and in a number of cell-based assays. (−)-trans-3-(5,6-dihydro-4H-pyrrolo[3,2,1-ij]quinolin-1-yl)-4-(1H-indol-3-yl) pyrrolidine-2,5,-dione was advanced into clinical trials and was well-tolerated, exhibiting signs of tumor response in late stage cancer patients with metastatic disease (Rosen, L. et al. (2006) 18th EORTC-NCI-AACR Symposium on Molecular Targets and Cancer Therapeutics (7-10 Nov. 2006, Prague, Czech Republic). Eur J Cancer Suppl 4, 196).

To potentially inform phase II clinical trials, in vitro combination studies were performed using (−)-trans-3-(5,6-dihydro-4H-pyrrolo[3,2,1-ij]quinolin-1-yl)-4-(1H-indol-3-yl) pyrrolidine-2,5,-dione with gemcitabine, the current drug standard of care used for pancreatic cancer treatment. The purpose of this study was to independently recapitulate the effects of (−)-trans-3-(5,6-dihydro-4H-pyrrolo[3,2,1-ij]quinolin-1-yl)-4-(1H-indol-3-yl) pyrrolidine-2,5,-dione and gemcitabine combination on human pancreatic cancer cell lines using a different method of calculation and comparing with the data obtained by the CalcuSyn™ software (Biosoft).

Figure 8:
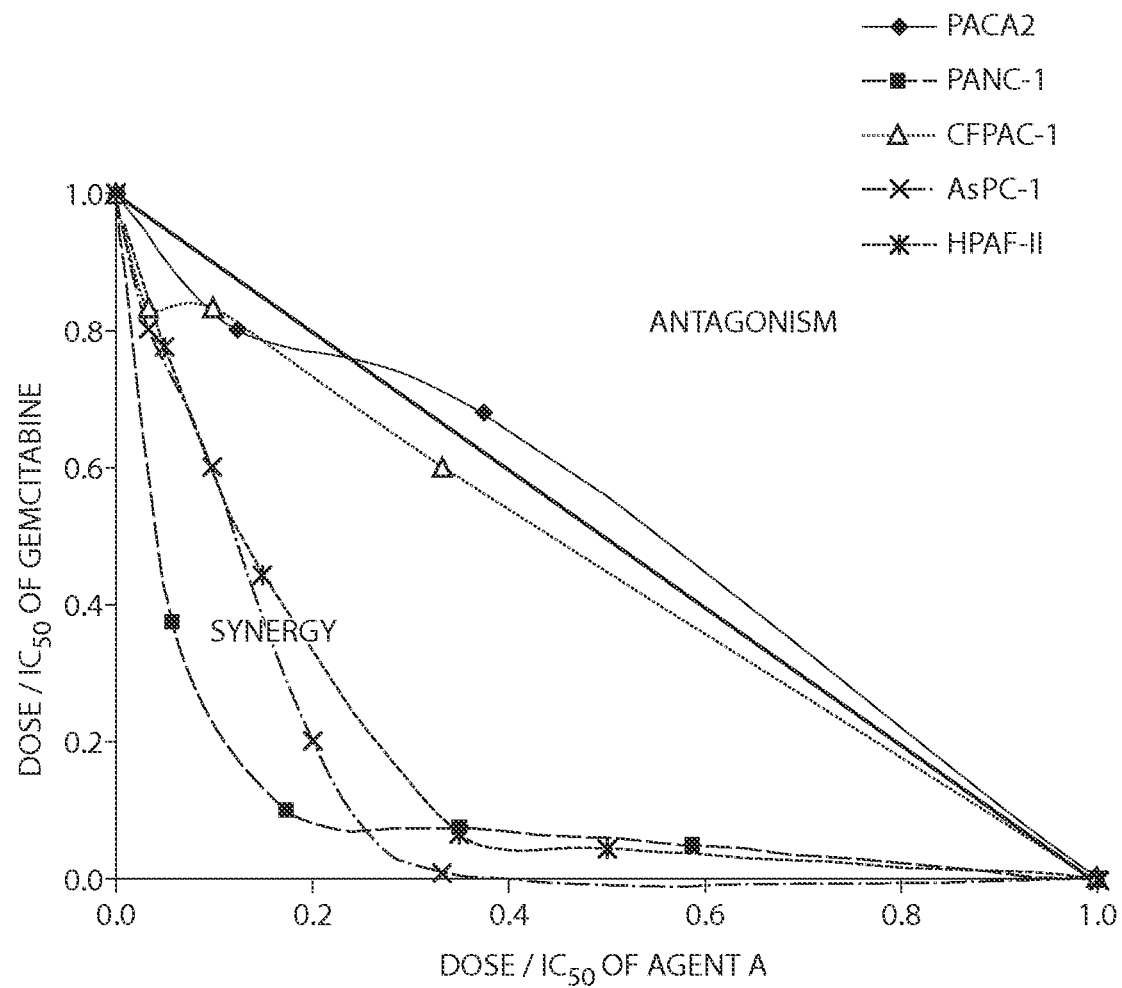
FIG. 8 is a graph showing the dose response curves for the combinatinorial treatment of (−)-trans-3-(5,6-dihydro-4H-pyrrolo[3,2,1-ij]quinolin-1-yl)-4-(1H-indol-3-yl) pyrrolidine-2,5-dione and gemcitabine in pancreatic cell lines.

MIA PaCa-2 (also referred to as PACA2), PANC-1, CFPAC-1, and Hs766T human pancreatic cell lines were maintained in DMEM supplemented with 10% fetal bovine serum (FBS), penicillin, streptomycin, and fungizone. AsPC-1 cells were maintained in RPMI supplemented with 10% FBS, penicillin, streptomycin, and fungizone. HPAF-II cells were maintained in MEM supplemented with 10% FBS, penicillin, streptomycin, and fungizone. For the MTS cytotoxicity assay, cells were plated in 96-well plates at 2,000 cells per well and incubated with increasing concentrations of (−)-trans-3-(5,6-dihydro-4H-pyrrolo[3,2,1-ij]quinolin-1-yl)-4-(1H-indol-3-yl) pyrrolidine-2,5,-dione and gemcitabine in combination for 72 hr. MTS reagent (Promega, Madison, Wis.) was added to each well and plates were incubated for 4 hr at 37° C. The absorbance of each well was measured at 492 nm using a microplate reader. A preliminary experiment with (−)-trans-3-(5,6-dihydro-4H-pyrrolo[3,2,1-ij]quinolin-1-yl)-4-(1H-indol-3-yl) pyrrolidine-2,5,-dione or gemcitabine (GEM) alone was performed to determine the $IC_{50}$ of each individual compound on each cell line and a concentration range was also determined. The layout of dose range of (−)-trans-3-(5,6-dihydro-4H-pyrrolo[3,2,1-ij]quinolin-1-yl)-4-(1H-indol-3-yl) pyrrolidine-2,5,-dione (shown as Agent A in FIG. 8) and gemcitabine for drug combination analysis was further determined. The $IC_{50}$ calculation and $IC_{50}$ value determinations are shown in Table 12 and FIG. 8.

The results of these studies show that the combination of (−)-trans-3-(5,6-dihydro-4H-pyrrolo[3,2,1-ij]quinolin-1-yl)-4-(1H-indol-3-yl) pyrrolidine-2,5,-dione and gemcitabine provides a synergistic anti-proliferative effect in PANC-1, HPAF-II and AsPC-1 human pancreatic cancer cell lines. All three pancreatic cell lines were sensitive to the combinatorial treatment of (−)-trans-3-(5,6-dihydro-4H-pyrrolo[3,2,1-ij]quinolin-1-yl)-4-(1H-indol-3-yl) pyrrolidine-2, 5,-dione and gemcitabine. The results of this study recapitulate previous work and confirm that the combination of (−)-trans-3-(5,6-dihydro-4H-pyrrolo[3,2,1-ij]quinolin-1-yl)-4-(1H-indol-3-yl) pyrrolidine-2,5,-dione and gemcitabine is synergistic in 3 out of the 6 pancreatic cell lines tested.

TABLE 12

| Cell Line | Tissue Origin | Chemotherapeutic Agent | Combination Index Values at $ED_{50}$ | Combination Conclusion |
|---|---|---|---|---|
| AsPC-1 | Pancreatic | Gemcitabine | 0.6 | Synergism |
| HPAF-II | Pancreatic | Gemcitabine | 0.2 | Synergism |
| PANC-1 | Pancreatic | Gemcitabine | 0.7 | Synergism |

Example 86

Combination of c-Met Inhibitors and Taxotere for the Treatment of Pancreatic Cancer, Colon Cancer and Prostate Cancer The effects of (−)-trans-3-(5,6-dihydro-4H-pyrrolo[3,2,1-ij]quinolin-1-yl)-4-(1H-indol-3-yl) pyrrolidine-2,5,-dione with taxotere were tested in MIA PaCa-2 pancreatic tumor cells, PC-3 prostate tumor. For each cell line, the $IC_{50}$ value of taxotere was predicted to be approximately 5 nM, while the $IC_{50}$ of (−)-trans-3-(5,6-dihydro-4H-pyrrolo[3,2,1-ij]quinolin-1-yl)-4-(1H-indol-3-yl) pyrrolidine-2,5,-dione was predicted to be 150 nM for MIA PaCa-2 cells, and 1 M for PC-3 cells. For these cell lines (−)-trans-3-(5,6-dihydro-4H-pyrrolo[3,2,1-ij]quinolin-1-yl)-4-(1H-indol-3-yl) pyrrolidine-2,5,-dione:taxotere ratios of 200-1000:1 were used, depending on predicted $IC_{50}$ values. For MIA PaCa-2 cells the CI was 0.99 at the $ED_{50}$, (Table 15) and therefore the effects of the combination were additive. The compound (−)-trans-3-(5,6-dihydro-4H-pyrrolo[3,2,1-ij]quinolin-1-yl)-4-(1H-indol-3-yl) pyrrolidine-2,5,-dione is identified as "Agent A" is this table. Median effect plots and isobolograms were performed for each experiment.

TABLE 15

| | Combination Parameters | | |
|---|---|---|---|
| Agent(s) | CI at $ED_{50}$ | $IC_{50}$ | R |
| Agent A & Taxotere (200:1) | 0.99 | 149 nM | 0.94 |
| Agent A | N/A | 177 nM | 0.95 |
| Taxotere | N/A | 5.1 nM | 0.99 |

This combination was also tested in PC-3 cells, where the combination index ranged between 0.68 and 1.51 at $ED_{50}$ (Table 16). The compound (−)-trans-3-(5,6-dihydro-4H-pyrrolo[3,2,1-ij]quinolin-1-yl)-4-(1H-indol-3-yl) pyrrolidine-2, 5,-dione is identified as "Agent A" is this table.

TABLE 16

| | Combination Parameters | | |
|---|---|---|---|
| Agent(s) | CI at $ED_{50}$ | $IC_{50}$ | R |
| Agent A & Taxotere (200:1) | 1.51 | 590 nM | 0.98 |
| Agent A | N/A | 875 nM | 0.98 |
| Taxotere | N/A | 3.5 nM | 0.97 |
| Agent A & Taxotere (200:1) | 0.68 | 259 nM | 0.93 |
| Agent A | N/A | 553 nM | 0.96 |
| Taxotere | N/A | 6 nM | 0.96 |

It has been demonstrated that (−)-trans-3-(5,6-dihydro-4H-pyrrolo[3,2,1-ij]quinolin-1-yl)-4-(1H-indol-3-yl) pyrrolidine-2,5,-dione and taxotere has a beneficial effect when dosed in combination in xenograft studies. While the 72 hour MTT data suggested that the combination of (−)-trans-3-(5,6-dihydro-4H-pyrrolo[3,2,1-ij]quinolin-1-yl)-4-(1H-indol-3-yl) pyrrolidine-2,5,-dione and taxotere was additive, the MTT assay may be the most accurate assay of cell death due to taxotere's mechanism of action of cell death. Therefore, additional combination cell death assays using colony formation were performed in order to capture the long term effects of (−)-trans-3-(5,6-dihydro-4H-pyrrolo[3,2,1-ij]quinolin-1-yl)-4-(1H-indol-3-yl) pyrrolidine-2,5,-dione and taxotere on cell death. Colony formation assays were performed in PC-3, HT29, and MIA PaCa-2 cells to determine whether the effects of this combination were synergistic. By colony formation assay the CI for MIA PaCa-2 cells was 0.43, which indicates synergism. Slight synergism to additivity was also observed for HT-29 cells, whereas the (−)-trans-3-(5,6-dihydro-4H-pyrrolo[3,2,1-ij]quinolin-1-yl)-4-(1H-indol-3-yl) pyrrolidine-2,5,-dione:taxotere mixture was additive for PC-3 cells.

These data combined with the shorter-term MTT assays demonstrates a synergistic anti-proliferative effect of (−)-trans-3-(5,6-dihydro-4H-pyrrolo[3,2,1-ij]quinolin-1-yl)-4-(1H-indol-3-yl) pyrrolidine-2,5,-dione with taxotere pancreatic cancer cells, prostate cancer cells and colon cancer cells.

Example 87

Combination of c-Met Inhibitors and Chemotherapeutic Agents In Vitro for the Treatment of Cancer c-Met is a high affinity receptor for hepatocyte growth factor (HGF) (Weidner K. M. et al. J Cell Biol. 1993 April; 121(1):145-54). Interaction of c-Met with HGF results in autophosphorylation at multiple tyrosines, which provide binding sites for and activate several downstream signaling components, including Gab 1, c-Cbl and PI3 kinase (Bardelli A. et al. Oncogene. 1997 Dec. 18; 15(25):3103-11). Altered c-Met levels and hyperactivated c-Met have been documented in a variety of human tumors, including renal, colon and breast cancers and thus c-Met is an attractive cancer therapeutic target (Traxler P. et al. Med Res Rev. 2001 November; 21(6):499-512). (−)-trans-3-(5,6-dihydro-4H-pyrrolo[3,2,1-ij]quinolin-1-yl)-4-(1H-indol-3-yl) pyrrolidine-2,5,-dione has been shown to inhibit c-Met activity in biochemical assays and in a number of cell-based assays. (−)-trans-3-(5,6-dihydro-4H-pyrrolo[3,2,1-ij]quinolin-1-yl)-4-(1H-indol-3-yl) pyrrolidine-2,5,-dione was advanced into clinical trials and was well-tolerated, exhibiting signs of tumor response in late stage cancer patients with metastatic disease.

To potentially inform phase II clinical trials, an in vitro combination study was initiated using (−)-trans-3-(5,6-dihydro-4H-pyrrolo[3,2,1-ij]quinolin-1-yl)-4-(1H-indol-3-yl) pyrrolidine-2,5,-dione with a number of chemotherapeutic agents (gemcitabine, docetaxel and carboplatin) that are currently in clinical use.

MIA PaCa-2 (also referred to as PACA2), PANC-1, CFPAC-1, Hs766T, DU-145, PC-3 and SK-OV-3 cells were maintained in DMEM supplemented with 10% fetal bovine serum (FBS), penicillin, streptomycin, and fungizone. AsPC-1 and 22Rv-1 cells were maintained in RPMI 1640 supplemented with 10% fetal bovine serum (FBS), penicillin, streptomycin, and fungizone. HPAF-II cells were maintained in MEM supplemented with 10% fetal bovine serum (FBS), penicillin, streptomycin, and fungizone. For the MTS assay, cells were plated in 96-well plates at 2,000 cells per well and incubated with various doses of (−)-trans-3-(5,6-dihydro-4H-pyrrolo[3,2,1-ij]quinolin-1-yl)-4-(1H-indol-3-yl) pyrrolidine-2,5,-dione in combination with gemcitibine, docetaxel or carboplatin for 72 hr. The layout of dose range of (−)-trans-3-(5,6-dihydro-4H-pyrrolo[3,2,1-ij]quinolin-1-yl)-4-(1H-indol-3-yl) pyrrolidine-2,5,-dione, gemcitibine, docetaxel and carboplatin for drug combination analysis was determined. MTS was added to each well and plates were incubated for 4 hr at 37° C. The absorbance of each well was measured at 492 nm using a microplate reader. Combination indexes of (−)-trans-3-(5,6-dihydro-4H-pyrrolo[3,2,1-ij]quinolin-1-yl)-4-(1H-indol-3-yl) pyrrolidine-2,5,-dione with gemcitibine, docetaxel or carboplatin among the various cell lines was determined by CalcuSyn™ (Biosoft).

Combination indices of (−)-trans-3-(5,6-dihydro-4H-pyrrolo[3,2,1-ij]quinolin-1-yl)-4-(1H-indol-3-yl) pyrrolidine-2,5,-dione with gemcitabine, Docetaxel, and carboplatin in various cell lines were analyzed.

As described in Example 85, the combination of (−)-trans-3-(5,6-dihydro-4H-pyrrolo[3,2,1-ij]quinolin-1-yl)-4-(1H-indol-3-yl) pyrrolidine-2,5,-dione and gemcitabine shows a range of synergistic anti-proliferative effects in three of five human pancreatic cancer lines.

The combination of (−)-trans-3-(5,6-dihydro-4H-pyrrolo[3,2,1-ij]quinolin-1-yl)-4-(1H-indol-3-yl) pyrrolidine-2,5,-dione and Docetaxel demonstrates a range of synergistic anti-proliferative effects in two of three human prostate cancer lines, i.e. 22RV1 and DU145 as shown in Table 17.

The combination of (−)-trans-3-(5,6-dihydro-4H-pyrrolo[3,2,1-ij]quinolin-1-yl)-4-(1H-indol-3-yl) pyrrolidine-2,5,-dione and carboplatin demonstrates a slightly antagonistic effect in the SK-OV-3 ovarian carcinoma cell line.

TABLE 17

| Cell Line | Tissue Origin | Chemotherapeutic Agent | Combination Index Values at $ED_{50}$ | Combination Conclusion |
|---|---|---|---|---|
| 22RV1 | Prostate | Docetaxel | 0.7 | Synergism |
| DU-145 | Prostate | Docetaxel | 0.7 | Synergism |

Example 88

Figure 9:
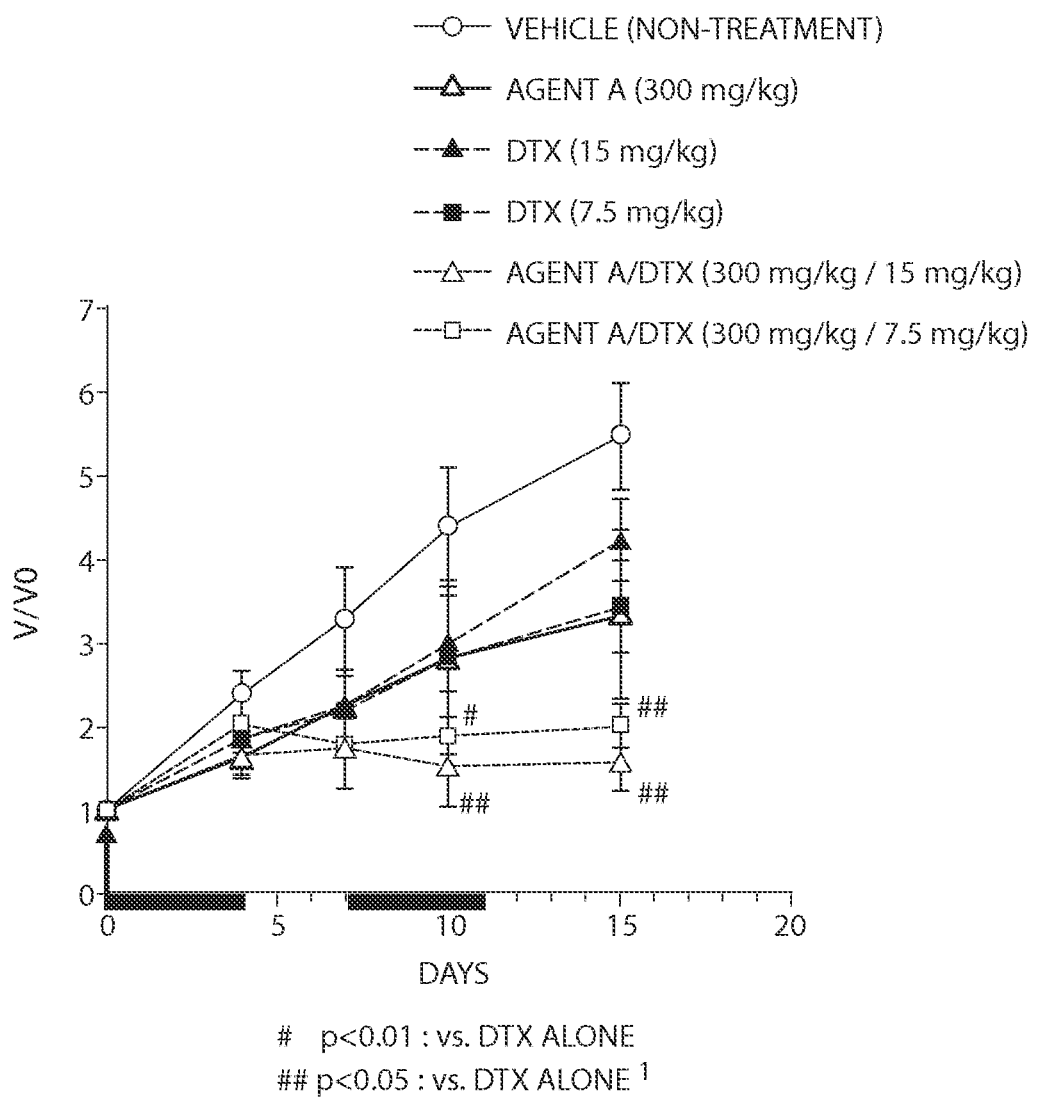
FIG. 9 is a graph depicting the volume of a MKN-45 human gastric tumor in a xenograft model as a proportion of its initial volume (V/Vo) following treatment with various doses of vehicle (control), (−)-trans-3-(5,6-dihydro-4H-pyrrolo[3,2,1-ij]quinolin-1-yl)-4-(1H-indol-3-yl) pyrrolidine-2,5-dione (Agent A), Docetaxel (DTX), or a combination thereof. # indicates p<0.05 vs. DTX treatment alone by a student's t-test. ## indicates p<0.01 vs. DTX treatment alone by a student's t-test.
Figure 10:
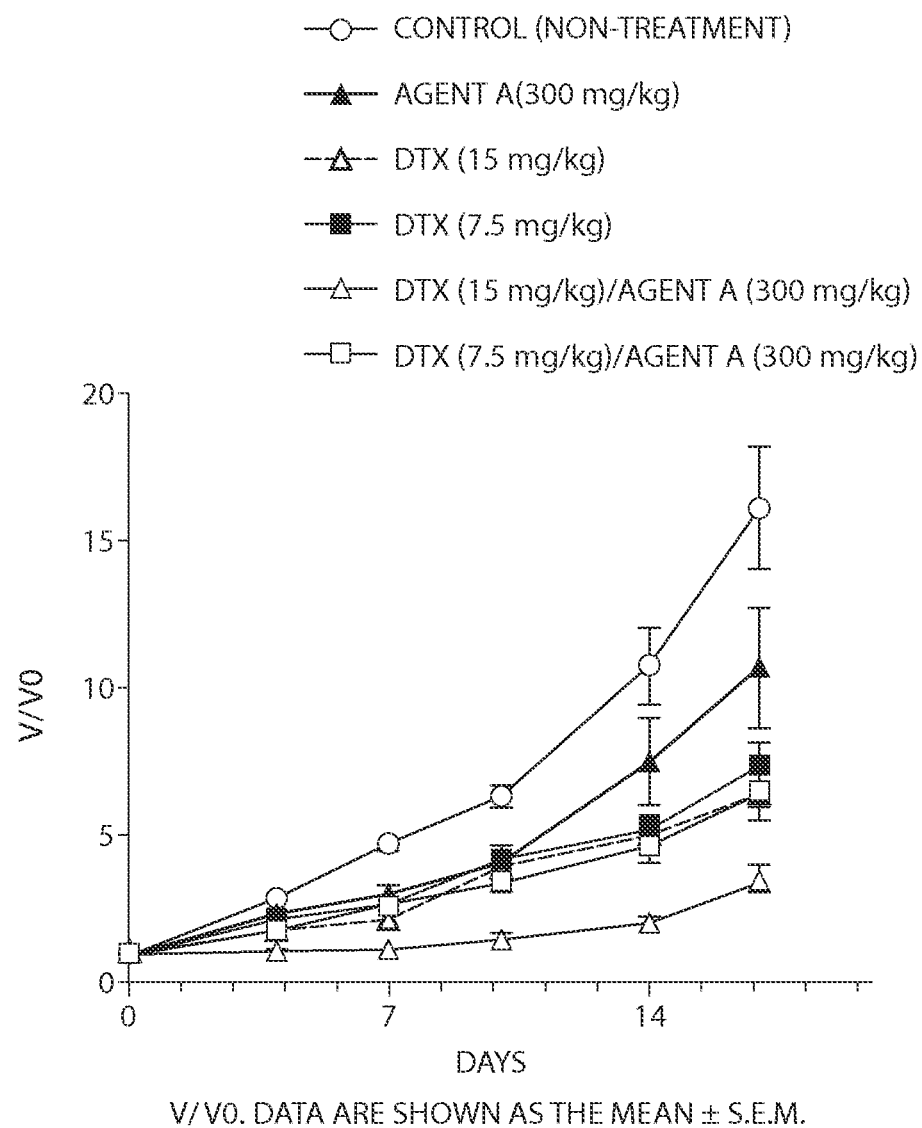
FIG. 10 is a graph depicting the volume of a Hsc-39 human gastric tumor in a xenograft model as a proportion of its initial volume (V/Vo) following treatment with various doses of vehicle, (−)-trans-3-(5,6-dihydro-4H-pyrrolo[3,2,1-ij]quinolin-1-yl)-4-(1H-indol-3-yl) pyrrolidine-2,5-dione (Agent A), Docetaxel (DTX), or a combination thereof. # indicates p<0.05 vs. DTX treatment alone by a stuendent's t-test. ## indicates p<0.01 vs. DTX treatment alone by a student's t-test.
Figure 11:
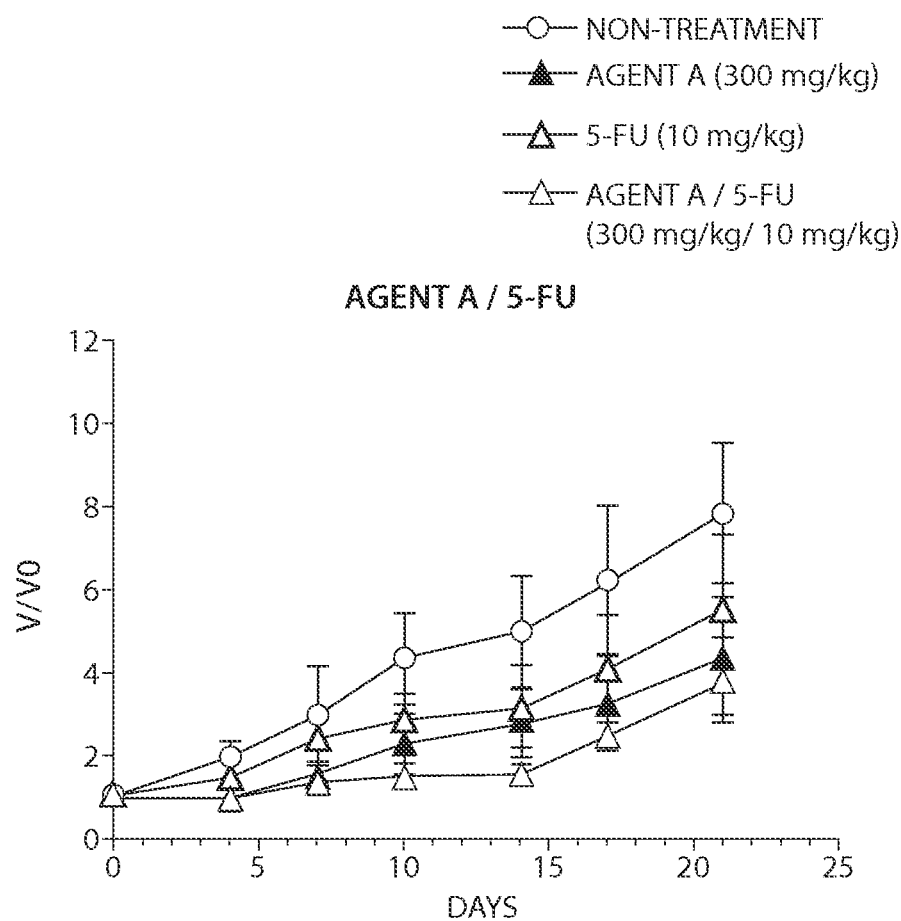
FIG. 11 is a graph depicting the volume of a MKN-45 human gastric tumor in a xenograft model as a proportion of its initial volume (V/Vo) following treatment with various doses of vehicle, (−)-trans-3-(5,6-dihydro-4H-pyrrolo[3,2,1-ij]quinolin-1-yl)-4-(1H-indol-3-yl) pyrrolidine-2,5-dione (Agent A), 5FU, or a combination thereof. # indicates p<0.05 vs. 5-FU treatment alone. * indicates p<0.05 vs. Agent A treatment alone by a student's t-test.
Figure 12:
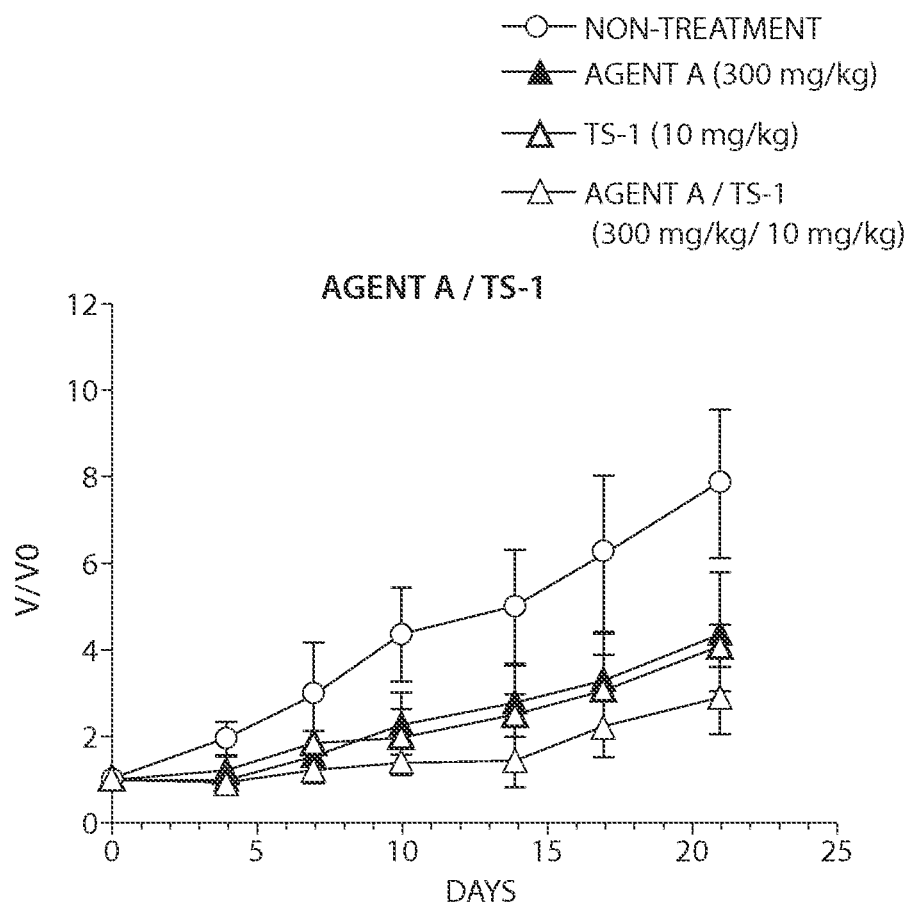
FIG. 12 is a graph depicting the volume of a MKN-45 human gastric tumor in a xenograft model as a proportion of its initial volume (V/Vo) following treatment with various doses of vehicle, (−)-trans-3-(5,6-dihydro-4H-pyrrolo[3,2,1-ij]quinolin-1-yl)-4-(1H-indol-3-yl) pyrrolidine-2,5-dione (Agent A), TS-1, or a combination thereof. # indicates p<0.05 vs. TS-1 treatment alone. * indicates p<0.05 vs. Agent A treatment alone by a student's t-test.
Figure 13:
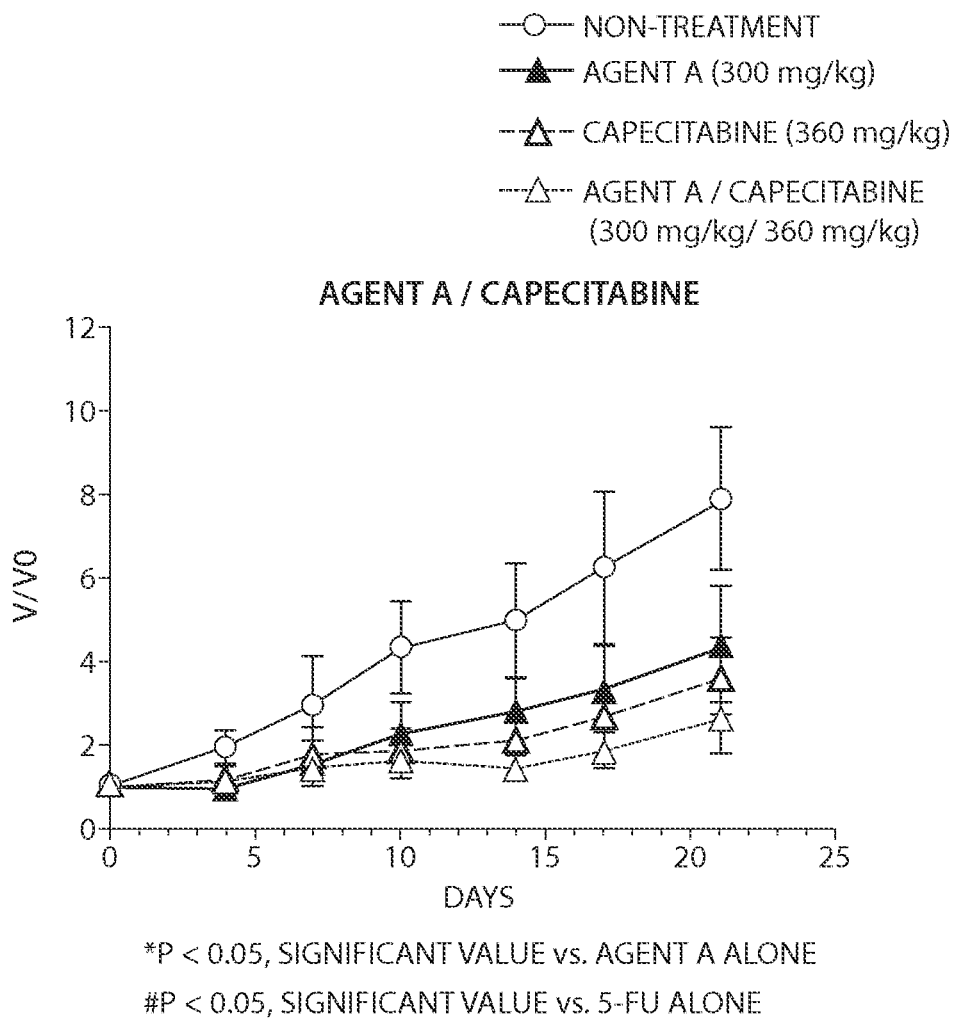
FIG. 13 is a graph depicting the volume of a MKN-45 human gastric tumor in a xenograft model as a proportion of its initial volume (V/Vo) following treatment with various doses of vehicle, (−)-trans-3-(5,6-dihydro-4H-pyrrolo[3,2,1-ij]quinolin-1-yl)-4-(1H-indol-3-yl) pyrrolidine-2,5-dione (Agent A), Capecitabine, or a combination thereof. # indicates p<0.05 vs. Capecitabine treatment alone. * indicates p<0.05 vs. Agent A treatment alone by a student's t-test.
Figure 14:
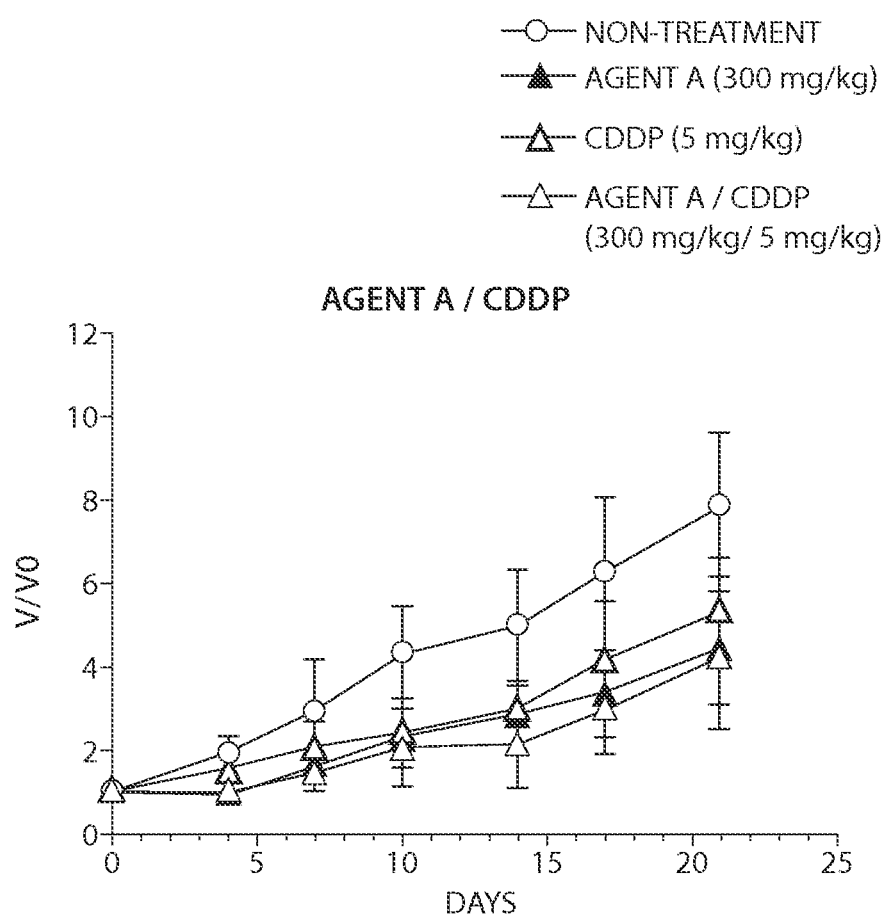
FIG. 14 is a graph depicting the volume of a MKN-45 human gastric tumor in a xenograft model as a proportion of its initial volume (V/Vo) following treatment with various doses of vehicle, (−)-trans-3-(5,6-dihydro-4H-pyrrolo[3,2,1-ij]quinolin-1-yl)-4-(1H-indol-3-yl) pyrrolidine-2,5-dione (Agent A), CDDP, or a combination thereof.

Combination of c-Met Inhibitors and Docetaxel In Vivo for the Treatment of Gastric Cancer A xenograft model was used to study the effects of a combinatorial therapy including (−)-trans-3-(5,6-dihydro-4H-pyrrolo[3,2,1-ij]quinolin-1-yl)-4-(1H-indol-3-yl) pyrrolidine-2,5,-dione and Docetaxel (DTX) on gastric cancer cells. Specifically, gastric cancer cell lines MKN-45 and Hsc-39 were tested. Evidence of the synergistic anti-proliferative effects of (−)-trans-3-(5,6-dihydro-4H-pyrrolo[3,2,1-ij]quinolin-1-yl)-4-(1H-indol-3-yl) pyrrolidine-2,5,-dione (Agent A) and Docetaxel (DTX) in a MKN-45 human gastric tumor xenograft model are provided in Table 18 and FIG. 9. Similarly, evidence of the synergistic anti-proliferative effects of (−)-trans-3-(5,6-dihydro-4H-pyrrolo[3,2,1-ij]quinolin-1-yl)-4-(1H-indol-3-yl) pyrrolidine-2,5,-dione (Agent A) and Docetaxel (DTX) in a Hsc-39 human gastric tumor xenograft model are provided in Table 19 and FIG. 10.

TABLE 18

| | Dosage (mg/kg) | Route | Schedule | T/C Min (on day) | BW loss (g) | Mortality |
|---|---|---|---|---|---|---|
| Non-Treatment | — | — | qd × 5 × 2 | 1.00 | −1.8 (10) | — |
| Agent A | 300 | p.o. | qd × 5 × 2 | 0.61 (15) | −1.3 (10) | 0/5 |
| Docetaxel | 15 | i.v. | single | 0.68 (7) | −3.8 (10) | 0/5 |
| Docetaxel | 7.5 | i.v. | single | 0.63 (15) | −3.0 (4) | 0/5 |
| Agent A + Docetaxel | 300 / 15 | p.o. / i.v. | qd × 5 × 2 / single | 0.29 (15) | −3.9 (10) | 0/5 |
| Agent A + Docetaxel | 300 / 7.5 | p.o. / i.v. | qd × 5 × 2 / single | 0.37 (15) | −2.7 (4) | 0/5 |

TABLE 19

| | Dosage (mg/kg) | Route | Schedule | T/C Min (on day) |
|---|---|---|---|---|
| Non-Treatment | — | — | — | 1.00 |
| Agent A | 300 | p.o. | qd × 5 × 2 | 0.63 (10) |
| Docetaxel | 15 | i.v. | single | 0.40 (17) |
| Docetaxel | 7.5 | i.v. | single | 0.46 (17) |
| Agent A + Docetaxel | 300 / 15 | p.o. / i.v. | qd × 5 × 2 / single | 0.19 (14) |

TABLE 19-continued

| | Dosage (mg/kg) | Route | Schedule | T/C Min (on day) |
|---|---|---|---|---|
| Agent A + Docetaxel | 300 7.5 | p.o. i.v. | qd × 5 × 2 single | 0.40 (17) |

What is claimed is:

1. A method of treating non-small cell lung cancer or colon cancer, said method comprising administering, to a subject in need thereof, a therapeutically effective amount of a composition comprising 360 mg of (−)-trans-3-(5,6-dihydro-4H-pyrrolo [3,2,1-ij] quinolin-1-yl)-4-(1H-indol-3-yl) pyrrolidine-2, 5-dione, or a pharmaceutically acceptable salt thereof, in combination with a therapeutically effective amount of erlotinib, wherein said non-small cell lung cancer or colon cancer cell is treated.

2. A pharmaceutical composition comprising 360 mg of (−)-trans-3-(5,6-dihydro-4H-pyrrolo [3,2,1-ij] quinolin-1-yl)-4-(1H-indol-3-yl) pyrrolidine-2, 5-dione, or a pharmaceutically acceptable salt thereof, and a therapeutically effective amount of erlotinib.

3. A kit for the treatment of non-small cell lung cancer or colon cancer in a subject comprising at least two vials, wherein a first vial contains a composition comprising 360 mg of (−)-trans-3-(5,6-dihydro-4H-pyrrolo [3,2,1-ij] quinolin-1-yl)-4-(1H-indol-3-yl) pyrrolidine-2, 5-dione, or a pharmaceutically acceptable salt thereof, and wherein at least a second vial contains a therapeutically effective amount of erlotinib, said kid further comprising instructions for administering said composition and erlotinib.

4. The method of claim 1 wherein the 360 mg of (−)-trans-3-(5,6-dihydro-4H-pyrrolo [3,2,1-ij] quinolin-1-yl)-4-(1H-indol-3-yl) pyrrolidine-2, 5-dione, or a pharmaceutically acceptable salt thereof, is administered twice daily for a total daily dose of 720 mg/day.

5. A method of treating non-small cell lung cancer or colon cancer, said method comprising administering, to a subject in need thereof, a therapeutically effective amount of a composition comprising (−)-trans-3-(5,6-dihydro-4H-pyrrolo [3,2,1-ij] quinolin-1-yl)-4-(1H-indol-3-yl) pyrrolidine-2, 5-dione, or a pharmaceutically acceptable salt thereof, in combination with a therapeutically effective amount of erlotinib, wherein the therapeutically effective amount of said composition comprising (−)-trans-3-(5,6-dihydro-4H-pyrrolo [3,2,1-ij] quinolin-1-yl)-4-(1H-indol-3-yl) pyrrolidine-2, 5-dione, or a pharmaceutically acceptable salt thereof, is 720 mg/day and, wherein said non-small cell lung cancer or colon cancer cell is treated.

* * * * *